(12) United States Patent
Parhami et al.

(10) Patent No.: US 9,683,009 B2
(45) Date of Patent: Jun. 20, 2017

(54) BONE-SELECTIVE OSTEOGENIC OXYSTEROL-BONE TARGETING AGENTS

(71) Applicants: The Regents of the University of California, Oakland, CA (US); University of Louisville Research Foundation, Inc., Louisville, KY (US)

(72) Inventors: Farhad Parhami, Los Angeles, CA (US); Frank Stappenbeck, Los Angeles, CA (US); Michael E. Jung, Los Angeles, CA (US); William M. Pierce, Jr., Louisville, KY (US); Kevyn Merten, Louisville, KY (US); K. Grant Taylor, Louisville, KY (US)

(73) Assignees: THE REGENTS OF THE UNIVERSITY OF CALIFORNIA, Oakland, CA (US); UNIVERSITY OF LOUISVILLE RESEARCH FOUNDATION, INC., Louisville, KY (US)

( * ) Notice: Subject to any disclaimer, the term of this patent is extended or adjusted under 35 U.S.C. 154(b) by 0 days.

(21) Appl. No.: 14/888,668

(22) PCT Filed: May 2, 2014

(86) PCT No.: PCT/US2014/036680
§ 371 (c)(1),
(2) Date: Nov. 2, 2015

(87) PCT Pub. No.: WO2014/179756
PCT Pub. Date: Nov. 6, 2014

(65) Prior Publication Data
US 2016/0159850 A1    Jun. 9, 2016

Related U.S. Application Data

(60) Provisional application No. 61/818,825, filed on May 2, 2013.

(51) Int. Cl.
*A61K 31/575* (2006.01)
*C07J 41/00* (2006.01)
*A61K 35/32* (2015.01)
*C07J 9/00* (2006.01)

(52) U.S. Cl.
CPC ......... *C07J 41/0055* (2013.01); *A61K 31/575* (2013.01); *A61K 35/32* (2013.01); *C07J 9/00* (2013.01)

(58) Field of Classification Search
USPC ................. 514/9.7, 169, 171, 456
See application file for complete search history.

(56) References Cited

U.S. PATENT DOCUMENTS

| | | |
|---|---|---|
| 3,309,387 A | 3/1967 | Furst et al. |
| 3,887,545 A | 6/1975 | Iacobelli et al. |
| 4,183,852 A | 1/1980 | Kaiser |
| 4,264,512 A | 4/1981 | Okamura et al. |
| 4,559,157 A | 12/1985 | Smith et al. |
| 4,608,392 A | 8/1986 | Jacquet et al. |
| 4,743,597 A | 5/1988 | Javitt et al. |
| 4,820,508 A | 4/1989 | Wortzman |
| 4,938,949 A | 7/1990 | Borch et al. |
| 4,961,922 A | 10/1990 | Shroot et al. |
| 4,992,478 A | 2/1991 | Geria |
| 5,166,320 A | 11/1992 | Wu et al. |
| 5,183,815 A | 2/1993 | Saari et al. |
| 5,219,740 A | 6/1993 | Miller et al. |
| 5,288,641 A | 2/1994 | Roizman |
| 5,723,455 A | 3/1998 | Tanabe et al. |
| 5,840,752 A | 11/1998 | Henry et al. |
| 5,929,062 A | 7/1999 | Haines |
| 6,017,904 A | 1/2000 | Reed et al. |
| 6,080,779 A | 6/2000 | Gasper et al. |
| 6,177,420 B1 | 1/2001 | Leemhuis et al. |
| 6,184,215 B1 | 2/2001 | Elias et al. |
| 6,316,503 B1 | 11/2001 | Li et al. |
| 6,420,353 B1 | 7/2002 | Lathe et al. |
| 6,436,917 B1 | 8/2002 | Droescher et al. |
| 6,518,262 B1 | 2/2003 | Leysen et al. |
| 6,586,189 B2 | 7/2003 | Forman |
| 6,863,900 B2 | 3/2005 | Kadiyala et al. |
| 6,893,830 B1 | 5/2005 | Janowski et al. |
| 6,906,069 B1 | 6/2005 | Li et al. |
| 7,060,450 B1 | 6/2006 | Tabin et al. |
| 7,196,220 B2 | 3/2007 | Pierce, Jr. et al. |
| 7,427,610 B2 | 9/2008 | Hillisch et al. |
| 8,071,575 B2 * | 12/2011 | Pierce, Jr. .............. A61K 31/70 514/169 |

(Continued)

FOREIGN PATENT DOCUMENTS

| | | |
|---|---|---|
| DE | 10204042822 | 3/2006 |
| EP | 337890 A1 | 10/1989 |
| EP | 0 415 731 A2 | 3/1991 |
| GB | 869007 A | 5/1961 |
| GB | 2 320 190 A | 6/1998 |

(Continued)

OTHER PUBLICATIONS

Abe et al., "Effects of bisphosphonates on osteoclastogenesis in RAW264.7 cells," 2012, *International Journal of Molecular Medicine* 29.6: 1007-1015.

Acsadi et al., "Human dystrophin expression in mdx mice after intramuscular injection of DNA constructs," 1991, *Nature* 352: 815-818.

Aghaloo et al. "Oxysterols enhance osteoblast differentiation in vitro and bone healing in vivo," 2005, *Journal of Bone & Mineral Research* American Society for Bone and Mineral Research (27th Annual Meeting). 20:9, sup. 1.: S361 (Abstract M203).

(Continued)

*Primary Examiner* — Pancham Bakshi
(74) *Attorney, Agent, or Firm* — Mintz Levin Cohn Ferris Glovsky and Popeo, P.C.

(57) ABSTRACT

Compounds and compositions for the treatment of bone disorders are presented.

12 Claims, 10 Drawing Sheets

(56) References Cited

U.S. PATENT DOCUMENTS

| | | |
|---|---|---|
| 9,526,737 B2 | 12/2016 | Parhami et al. |
| 9,532,994 B2 | 1/2017 | Parhami |
| 2003/0153541 A1 | 8/2003 | Dudley et al. |
| 2004/0072806 A1 | 4/2004 | Yao et al. |
| 2004/0077613 A1 | 4/2004 | Bamberg et al. |
| 2004/0176423 A1 | 9/2004 | Paralkar |
| 2004/0235739 A1 | 11/2004 | Mahanthappa |
| 2005/0095677 A1 | 5/2005 | Liu et al. |
| 2006/0251735 A1 | 11/2006 | Parhami |
| 2006/0270645 A1 | 11/2006 | Parhami |
| 2008/0070883 A1 | 3/2008 | Nagpal |
| 2009/0202660 A1 | 8/2009 | Parhami et al. |
| 2009/0202661 A1 | 8/2009 | Kirkpatrick |
| 2009/0220562 A1 | 9/2009 | Parhami |
| 2010/0012030 A1 | 1/2010 | Todd et al. |
| 2010/0034781 A1 | 2/2010 | Parhami et al. |
| 2010/0048944 A1 | 2/2010 | Parhami |
| 2010/0105645 A1 | 4/2010 | Parhami et al. |
| 2011/0008297 A1 | 1/2011 | Parhami et al. |
| 2012/0309730 A1 | 12/2012 | Parhami et al. |
| 2015/0118277 A1 | 4/2015 | Parhami et al. |
| 2015/0140059 A1 | 5/2015 | Parhami et al. |
| 2016/0206631 A1 | 7/2016 | Parhami et al. |

FOREIGN PATENT DOCUMENTS

| | | |
|---|---|---|
| JP | S51-11114 B1 | 4/1976 |
| JP | 2000-508911 A | 7/2000 |
| JP | 2000-511404 A | 9/2000 |
| JP | 2002-506030 A | 2/2002 |
| JP | 2002-506817 A | 3/2002 |
| WO | WO-90/07936 A1 | 7/1990 |
| WO | WO-91/02805 A2 | 3/1991 |
| WO | WO-93/09191 A1 | 5/1993 |
| WO | WO-93/10218 A1 | 5/1993 |
| WO | WO-93/11230 A1 | 6/1993 |
| WO | WO-93/25234 A1 | 12/1993 |
| WO | WO-93/25698 A1 | 12/1993 |
| WO | WO-94/03622 A1 | 2/1994 |
| WO | WO-94/26914 A1 | 11/1994 |
| WO | WO-95/13365 A1 | 5/1995 |
| WO | WO-97/40137 A1 | 10/1997 |
| WO | WO-99/45923 A1 | 9/1999 |
| WO | WO-99/47136 A1 | 9/1999 |
| WO | WO-00/54759 A2 | 9/2000 |
| WO | WO-01/15676 A2 | 3/2001 |
| WO | WO-01/94379 A2 | 12/2001 |
| WO | WO-02/080952 A2 | 10/2002 |
| WO | WO-2004/019884 A2 | 3/2004 |
| WO | WO-2005/005453 A2 | 1/2005 |
| WO | WO-2005/005453 A3 | 1/2005 |
| WO | WO-2005/020928 A2 | 3/2005 |
| WO | WO-2005/028616 A2 | 3/2005 |
| WO | WO-2005/123757 A1 | 12/2005 |
| WO | WO-2006/012902 A2 | 2/2006 |
| WO | WO-2006/110490 A2 | 10/2006 |
| WO | WO-2006/113667 A1 | 10/2006 |
| WO | WO-2007/028101 A2 | 3/2007 |
| WO | WO-2007/098281 A2 | 8/2007 |
| WO | WO-2008/011071 A2 | 1/2008 |
| WO | WO-2008/041003 A2 | 4/2008 |
| WO | WO-2008/082520 A2 | 7/2008 |
| WO | WO-2008/103951 A1 | 8/2008 |
| WO | WO-2008/109780 A1 | 9/2008 |
| WO | WO-2008/115469 A2 | 9/2008 |
| WO | WO-2009/073186 A1 | 6/2009 |
| WO | WO-2011/006087 A1 | 1/2011 |
| WO | WO-2011/103175 A2 | 8/2011 |
| WO | WO-2012/024581 A2 | 2/2012 |
| WO | WO-2012/024583 A2 | 2/2012 |
| WO | WO-2012/024584 A2 | 2/2012 |
| WO | WO2012024584 A2 * | 2/2012 ............ A61K 31/58 |
| WO | WO-2013/169397 A1 | 11/2013 |
| WO | WO-2013/169399 A1 | 11/2013 |
| WO | WO-2014/179756 A1 | 11/2014 |
| WO | WO-2015/168636 A1 | 11/2015 |
| ZA | 6808005 | 6/1969 |

OTHER PUBLICATIONS

Aghaloo et al., "Oxysterols enhance osteoblast differentiation in vitro and bone healing in vivo," 2007, Journal of Orthopaedic Research 25(11):1488-1497 (also known as Aghaloo 2006 in press).

Akazawa et al., "The upregulated expression of sonic hedgehog in motor neurons after rat facial nerve axotomy," 2004, Journal of Neuroscience, 24(36):7923-7930.

Albers M. et al., "A novel principle for partial agonism of liver X receptor ligands," 2006, Journal of Biological Chemistry 281(8):4920-4930.

Albrektsson et al., "Osteoinduction, osteoconduction and osseointegration," 2001, European Spine Journal, 10:S96-S101.

Almeida et al., "Wnt proteins prevent apoptosis of both uncommitted osteoblast progenitors and differentiated osteoblasts by beta-catenin-dependent and -independent signaling cascades involving Src/ERK and phosphatidylinositol 3-kinase/AKT," 2005, Journal of Biological Chemistry 280(50):41342-41351.

Amantea et al. "Oxysterols are novel activators of hedgehog and Wnt signaling," 2006, Journal of Bone and Mineral Research 21:S157-S157.

Amantea et al., "Oxysterol-induced osteogenic differentiation of marrow stromal cells is regulated by Dkk-1 inhibitable and P13-Kinase mediated signaling," 2008, Journal of Cellular Biochemistry 105(2): 424-436.

Antonio et al. "Oxysterol and 9-cis-retinoic acid stimulate the group IIA secretory phospholipase A2 gene in rat smooth-muscle cells," 2003, Biochemical Journal, 376(2): 351-360.

Arns et al., "Design and synthesis of novel bone-targeting dual-action pro-drugs for the teament and reversal of osteoporosis," 2012, Bioorganic and Medicinal Chemistry. 20(6):2131-2140.

Arnsdorf et al., "The periosteum as a cellular source for functional tissue engineering," 2009, Tissue Engineering 15(9):2637-2642.

Aspray et al., "Treatment of osteoporosis in women intolerant of oral bisphosphonates," 2012, Maturitas, 71:76-78.

Ayukawa et al., "Local application of statin promotes bone repair through the suppression of osteoclasts and the enhancement of osteoblasts at bone-healing sites in rats," 2009, Oral Surgary, Oral Medicine, Oral Pathology, Oral Radiology, and Endodontics 107(3): 336-342.

Bailey et al., "Sonic Hedgehog paracrine signaling regulates metastasis and lymphangiogenesis in pancreatic cancer," 2009, Oncogene 28(40): 3513-3525.

Banerjee et al., "Runt homology domain proteins in osteoblast differentiation: AML3/CBFA1 is a major component of a bone-specific complex," 1997, Journal of Cellular Biochemistry 66(1):1-8.

Bannai et al., "Studies on steroids. Part 37. Synthesis of the four stereoisomers of 20,22-epoxycholesterol," 1976, Journal of the Chemical Society, Perkin Transactions 1 (19): 2116-2120.

Barginear et al., "The hedgehog pathway as a therapeutic target for treatment of breast cancer," 2009, Breast cancer research and treatment 116(2):239-246.

Basu et al., "Association between oxidative stress and bone mineral density," 2001, Biochemical and Biophysical Research Communications 288(1):275-9.

Bauss et al., "Effect of 17B-estradiol-biphosphonate conjugates, potentiial bone-seeking estrogen pro-drugs, on 17B-estradiol serum kinetics and bone mass in rats," 1996, Calcified Tissue International 59: 168-173.

Beckers et al., "Disruption of hedgehog signalling in ApoE -/- mice reduces plasma lipid levels, but increases atherosclerosis due to enhanced lipid uptake by macrophages," 2007, Journal of Pathology 212(4):420-428.

Bennett et al., "Regulation of Wnt signaling during adipogenesis," 2002, Journal of Biological Chemistry 277(34): 30998-31004.

(56) References Cited

OTHER PUBLICATIONS

Bennett et al., "Regulation of osteoblastogenesis and bone mass by Wnt10b," 2005, *Proceedings of the National Academy of Sciences of the United States of America* 102(9):3324-3329.

Bergman et al., "Age-related changes in osteogenic stem cells in mice," 1996, *Journal of Bone and Mineral Research* 11:568-577.

Bestmann et al., "Synthesis and reaction of diazoacetyl chloride-Detection of Diazoketene," 1979, *Angewandte Chemie International Edition in English* 18(12):947-948.

Bijlsma et al., "Hedgehog: an unusual signal transducer," 2004, *Bioessays* 26(4):387-394.

Bijlsma et al., "Hedgehog morphogen in cardiovascular disease," 2006, *Circulation* 114(18):1985-1991.

Bilezikian et al., "Therapy of male osteoporosis with parathyroid hormone," 2001, *Calcified Tissue International* 69(4):248-251.

Bjorkhem et al., "On the possible use of the serum level of 7a-hydroxycholesterol as a marker for incrased activity of the cholesterol 7a-hydroxylase in humans," 1987, *jJournal of Lipid Research* 28(8): 889-894.

Bjorkhem et al., "Oxysterols in human circulation: which role do they have?," 2002, *Current opinions in lipidology* 13(3):247-253.

Bjorkhem et al., "Oxysterols: friends, foes, or just fellow passengers?," 2002, *Arteriosclerosis, thrombosis, and vascular biology* 22(5):734-742.

Black et al., "Continuing bisphosphonate treatment for osteoporosis—for whom and for how long?" 2012, *New England Journal of Medicine* 366(22), 2051-2053.

Boguslawski et al., "Activation of osteocalcin transcription involves interaction of protein kinase A- and protein kinase C-dependent pathways," 2000, *The Journal of Biological Chemistry.* 275(2):999-1006.

Boland et al., "Wnt 3a promotes proliferation and suppresses osteogenic differentiation of adult human mesenchymal stem cells," 2004, *Journal of Cellular Biochemistry.* 93(6):1210-30.

Braunersreuther et al., "Leukocyte recruitment in atherosclerosis: potential targets for therapeutic approaches?" 2006, *Cellular and Molecular Life Sciences* 63(18): 2079-2088.

Brewer et al., "Current and future treatment options in osteoporosis," 2011, *European Journal of Clinical Pharmacology* 67(4): 321-331.

Bruice T. C. et al. *Bioorganic Mechanisms*, vol. 1, W. A. Benjamin, New York, 1966, 1-258.

Bunta, et al., "Stereoselective synthesis of (22R)- and (22S)-castasterone/ponasterone A hybrid compounds and evaluation of their molting hormone activity," 2004, *Steroids* 69: 483-493.

Burger et al., "Acetylenic cholesteryl derivatives as irreversible inhibitors of ecdysone biosynthesis," 1988, *Tetrahedron* 44(4): 1141-1152.

Burstein et al., "A Preliminary Report on the Intermediates in the Conversion in Vitro of Cholesterol to Pregnenolone in Adrenal Preparations," 1969, *Steroids* 14;(2):207-217.

Burstein et al., "Reactions of 20-Hydroxylated Steroids with Bovine Adrenal Tissue Preparations," 1969, *Steroids* 13(3):399-412.

Byon et al., "Stereospecific synthesis of the four 20,22-epoxycholesterols and of (Z)-20(22)-Dehydrocholesterol," 1976, *The Journal of Organic Chemistry* 41:3716-3722.

Byrd et al., "Hedgehog signaling in murine vasculogenesis and angiogenesis," 2004, *Trends in cardiovascular medicine* 14(8):308-313.

Cadot et al., "First synthesis of a steroid containing an unstable 19-nor-androsta-1,5-dien-3-one system," 2006, *Tetrahedron* 62: 4384-4392.

Canalis et al. "Update in new anabolic therapies for osteoporosis," 2010, *The Journal of Clinical Endocrinology and Metabolism* 95(4), 1496-1504.

Caplan et al. "The mesengenic process," 2004, *Bone Repair and Regeneration* 21(3):429-435.

Caplan et al., "Mesenchymal stem cells: building blocks for molecular medicine in the 21st century," 2001, *Trends in Molecular Medicine* 7(6):259-64. Review.

Chan et al. "Age-related bone loss: old bone, new facts," 2002, *Gerontology* 48(2):62-71.

Chaudhuri et al., "Stereochemistry of the addition reactions of Grignard reagents to 20-keto steroids. Syntheses of 17alpha,20alpha-dihydroxycholesterol," 1969, *The Journal of Organice Chemistry* 34(12):3759-3766.

Chen et al., "Inhibition of hedgehog signaling by direct binding of cyclopamine to Smoothened," 2002, *Genes & Development* 16(21):2743-2748.

Chen et al., "Age-related osteoporosis in biglycan-deficient mice is related to defects in bone marrow stromal cells," 2002, *Journal of Bone and Mineral Research* 17(2):331-340.

Chen et al., "Bone morphogenetic proteins." 2004, *Growth Factors* 22(4):233-41.

Chen et al., "Small molecule modulation of Smoothened activity," 2002, *Proceedings of the National Academy of Sciences*, 99(22), 14071-14076.

Cheng et al., Chemistry and Biochemistry of Chinese Drugs. Part 1. Sterol Derivatives Cytotoxic to Hepatoma Cells, Isolated from the Drug Bombyx cum Botryte, 1977, *Journal of Chemical Research* (M) v. 9 pp. 2501-2521.

Cheng et al., "Chemistry and Biochemistry of Chinese Drugs. Part 1. Sterol Derivatives Cytotoxic to Hepatoma Cells, Isolated from the Drug Bombyx cum Botryte," 1977, *Journal of Chemical Research* (S), v. 9 p. 217.

Chisholm et al., "The LXR ligand T0901317 induces severe lipogenesis in the db/db diabetic mouse," 2003, *Journal of Lipid Research* 44(11):2039-2048; 2003.

Choo et al., "Cytochrome P-450 inhibition blocks bone resorption in vitro and in vivo," 1999, *Otolaryngology-Head and Neck Surgery*, 120(1): 84-91.

Chuu et al., "The liver X receptor agonist T0901317 acts as androgen receptor antagonist in human prostate cancer cells," 2007, *Biochemical and biophysical research communications* 357(2):341-346.

Chuu et al., "Inhibition of tumor growth and progression of LNCaP prostate cancer cells in athymic mice by androgen and liver X receptor agonist," 2006, *Cancer Research* 66(13):6482-6486.

Ciobanu et al., "Synthesis and steroid sulphatase inhibitory activity of C19- and C21-steroidal derivatives bearing a benzyl-inhibiting group," 2001, *European Journal of Medicinal Chemistry* 36(7), pp. 659-671.

Clément-Lacroix et al., "Lrp5-independent activation of Wnt signaling by lithium chloride increases bone formation and bone mass in mice," 2005, *Proceedings of the National Academy of Sciences of the United States of America* 102(48):17406-17411.

Clevers H., "Wnt/beta-catenin signaling in development and disease," 2006, *Cell* 127(3):469-80.

Cline et al., "Perspectives for gene therapy: inserting new genetic information into mammalian cells by physical techniques and viral vectors," 1985, *Pharmacology and therapeutics* 29(1):69-92.

Cohen, "The hedgehog signaling network," 2003, *American Journal of Medical Genetics* 123A:5-28.

Corcoran et al., "Oxysterols stimulate sonic hedgehog and proliferation of medulloblastoma cells," 2006, *Proceedings of the National Academy of Sciences* 103(22): 8408-8413.

Cosman et al. "Anabolic and Atiresorptive Therapy for Osteoporosis: Combination and Sequential Approaches," 2014, *Current osteoporosis reports* 12(4):385-395.

Cummings et al., "Epidemiology and outcomes of osteoporotic fractures," 2002, *The Lancet* 359(9319):1761-1767.

Day et al., "Wnt/beta-catenin signaling in mesenchymal progenitors controls osteoblast and chondrocyte differentiation during vertebrate skeletogenesis," 2005,*Developmental Cell.* 8(5):739-50.

De La Rosa et al., "Cross-coupling reactions of monosubstituted acetylenes and aryl halides catalyzed by palladium on charcoal," 1990, *Synthetic Communications* 20(13): 2059-2064.

Debiais et al., "Fibroblast growth factor-2 induces osteoblast survival through a phosphatidylinositol 3-kinase-dependent, -beta-catenin-independent signaling pathway," 2004, *Experimental Cell Research* 297(1):235-46.

(56) References Cited

OTHER PUBLICATIONS

Devos et al., "Syntheseis of acyl halides under very mild conditions," 1979, *Journal of the Chemical Society, Chemical Communications* 24:1180-1181.
Dimitriou et al., "Bone regeneration: current concepts and future directions," 2011, *BMC Medicine* 9(1):1-10.
Dimmeler et al. "HMG-CoA reductase inhibitors (statins) increase endothelial progenitor cells via the PI 3-kinase/Akt pathway," 2001, Journal of Clin Invest. 108(3): 391-397.
Dlugosz et al., "Following the Hedgehog to new cancer therapies," 2009, *New England Journal of Medicine* 361(12):1202-1205.
Drew et al., "Synthesis of Pregnenolone of Flourescent Cholesterol Analogue Probes with Conjugated Unsaturation in the Side Chain," 1987, *Journal of Organic Chemistry* 52(18):4047-4052.
Ducy et al., "Osf2/Cbfa1: A transcriptional activator of osteoblast differentiation," 1997, *Cell* 89(5):747-754.
Ducy, "Cbfa1: a molecular switch in osteoblast biology," 2000, *Developmental Dynamics* 219(4):461-71.
Dwyer et al., "Oxysterols are novel activators of the Hedgehog signaling pathway in pluripotent mesenchymal cells," 2007, *The Journal of Biological Chemistry* 282(12):8959-8968.
Eastell, "Treatment of postmenopausal osteoporosis," 1998, *The New England Journal of Medicine* 338(11):736-746.
Ebetino et al., "The relationship between the chemistry and biological activity of the bisphosphonates," 2011, *Bone* 49(1):20-33.
Edwards et al., "Sterols and isoprenoids: signaling molecules derived from the cholesterol biosynthetic pathway," 1999, *Annual review of biochemistry* 68(1):157-185.
Edwards et al., "BAREing it all: the adoption of LXR and FXR and their roles in lipid metabolism," 2002, *Journal of lipid research* 43(1):2-12.
Ettinger, "Aging bone and osteoporosis: strategies for preventing fractures in the elderly," 2003, *Archives of Internal Medicine* 163(18):2237-2246.
Fajas et al., "Regulation of peroxisome proliferator-activated receptor gamma expression by adipocyte differentiation and determination factor 1/sterol regulatory element binding protein 1: implications for adipocyte differentiation and metabolism," 1999, *Molecular and Cellular Biology* 19(8):5495-5503.
Feldmann et al., "Blockade of Hedgehog signaling inhibits pancreatic cancer invasion and metastasis: A new paradigm for combination therapy in solid tumors," 2007, *Cancer Research* 67(5):2187-2196.
Fievet et al., "Liver X receptor modulators: Effects on lipid metabolism and potential use in the treatment of atherosclerosis," 2009, *Biochemical Pharmacology* 77(8):1316-1327.
Forman et al., "The orphan nuclear receptor LXRa is positively and negatively regulated by distinct products of mevalonate metabolism," 1997, *Proceedings of the National Academy of Sciences of the United States of America* 94(20), pp. 10588-10593.
Franceschi et al., "Gene Therapy for Bone Formation: In Vitro and In Vivo Osteogenic Activity of an Adenovirus Expressing BMP7," 2000, *Journal of Cellular Biochemistry* 78:476-486.
Franceschi et al., "Regulation of the Osteoblast-Specific Transcription Factor, Runx2: Responsiveness to Multiple Signal Transduction Pathways," 2003, *Journal of Cellular Biochemistry* 88(3):446-454.
Friedmann et al., "Progress toward human gene therapy," 1989, *Science* 244(4910):1275-1281.
Fujita et al., "Runx2 induces osteoblast and chondrocyte differentiation and enchances their migration by coupling with PI3K-Akt signaling," *The Journal of Cell Biology* 166(1):85-95.
Fukuchi et al., "Antiproliferative effect of liver x receptor agonists on LNCaP prostate cancer cells," 2004, *Cancer Research* 64(21): 7686-7689.
Galus et al., "Fluvastatin does not elevate periosteal osteogenesis induced by Moloney sarcoma virus (MSV) in mice," 2006, *Pharmacological Reports* 58(1):60-66.
Garrett et al., "The role of statins as potential targets for bone formation," 2003, Arthritis Res., 4(4): 237-240.

Garrett et al., "Selective inhibitors of the osteoblast protease stimulate bone formation in vivo and in vitro," 2003, *The journal of clinical investigation* 111(11):1771-1782.
Gaur et al., "Canonical WNT signaling promotes osteogenesis by directly stimulating *Runx2* gene expression," 2005, *The Journal of Biological Chemistry* 280(39): 33132-33140.
Gen et al., "Nonenzymic biogenetic-like olefinic cyclizations. Stereospecific cyclization of dienic acetals," 1973, *Journal of the American Chemical Society* 95(8):2656-2663.
Geyeregger et al., "Liver x receptors interfere with cytokine-induced proliferation and cell survival in normal and leukemic lymphocytes," 2009, *Journal of Leukocyte Biology* 86:1039-1048.
Ghosh-Choudhury et al., "Requirement of BMP-2-induced phosphatidylinositol 3-kinase serine/threonine kinase in osteoblast differentiation and Smad-dependent *BMP-2* gene transcription," 2002, *Journal of Biological Chemistry* 277(36):33361-33368.
Ghosh-Choudhury et al., "Statin-induced Ras activation integrates the phosphatidylinositol 3-kinase signal to akt and mapk for bone morphogenetic protein-2 expression in osteoblast differentiaiton," 2007, *The Journal of Biological Chemstry* 282(7):4983-4993.
Gill et al., "Sterol regulators of cholesterol homeostasis and beyond: The oxysterol hypothesis revisited and revised," 2008, *Progress in Lipid Research* 47(6):391-404.
Gimble et al., "Peroxisome proliferator-activated receptor-? activation by thiazolidinediones induces adipogenesis in bone marrow stromal cells," 1996, *Molecular Pharmacology* 50(5):1087-1094.
Goltzman et al., "Discoveries, drugs and skeletal disorders," 2002, *Nature Reviews Drug Discovery* 1(10):784-796.
Gordon et al., "Wnt signaling: multiple pathways, multiple receptors, and multiple transcription factors," 2006, *Journal of Biological Chemisty* 281(32):22429-22433.
Gori et al., "Differentiation of human marrow stromal precursor cells: bone morphogenetic protein-2 increases OSF2/CBFA1, enhances osteoblast commitment, and inhibits late adipocyte maturation," 1999, *Journal of Bone and Mineral Research* 14(9):1522-1535.
Gregorio-King et al., "Effect of oxysterols on hematopoietic progentior cells," 2002, *Experimental Hematology* 30(7): 670-678.
Hanada et al., "Stimulatory effects of basic fibroblast growth factor and bone morphogenetic protein-2 osteogenic differentiation of rat bone marrow-derived mesenchymal stem cells," 1997 *Journal of Bone and Mineral Research* 12(10): 1606-1614.
Hanley et al., "Oxysterols induce differentiation in human keratinocytes and increase AP-1-dependent involucrin transcription," 2000, *Journal of Investigative Dermatology* 114(3):545-553.
Hayden et al., "Induction of moncyte differentiation and foam cell formation in vitro by 7-ketocholesterol," 2002, *Journal of Lipid Research* 43(1):26-35.
Hicok et al., "Development and characterization of conditionally immortalized osteoblast precursor cell lines from human bone marrow stroma," 1998, *Journal of Bone and Mineral Research* 13(2):205-217.
Hill et al., "Canonical Wnt/beta-catenin signaling prevents osteoblasts from differentiating into chondrocytes," 2005, *Developmental Cell* 8(5):727-738.
Hilton M. et al., "Ihh controls cartilage development by antagonizing Gli3, but requires additional effectors to regulate osteoblast and vascular development," 2005, *Development* 132(19):4339-4351.
Hirotsu et al., "Smoothened as a new therapeutic target for human osteosarcoma," 2010, *Molecular Cancer* 9(1):1-14.
Hochman E. et al., "Molecular pathways regulating pro-migratory effects of hedgehog signaling," 2006, *Journal of Biological Chemistry* 281(45):33860-33870.
Hokugo et al., "A novel oxysterol promotes bone regenration in rabbit cranial bone defects," 2013, *Journal of Tissue Engingeering and Regenerative Medicine*.
Honda et al., "Structures of thornasterols A and B (Biologically active glycosides from Asteroidia, XI)," 1986, *Tetrahedron Letters* 27(29):3369-3372.
Honda et al., "Stereoselective synthesis of petrosterol and a formal synthesis of aragusterols," 1996, *Journal of the Chemical Society, Perkin Transactions 1* 18: 2291-2296.

(56) References Cited

OTHER PUBLICATIONS

Hosack et al., "Identifying biological themes within lists of genes with EASE," 2003, *Genome Biology* 4(10):R70.
Hu et al., "Sequential roles of hedgehog and Wnt signaling in osteoblast development," 2004, *Development* 132(1):49-60.
Hummasti et al., "Liver X receptors are regulators of adipocyte gene expression but not differentiation: identification of apoD as a direct target," 2004, *Journal of Lipid Research* 45(4):616-625.
Ichioka et al., Prevention of senile osteoporosis in SAMP6 mice by intrabone marrow injection of allogeneic bone marrow cells, 2002, *Stem Cells* 20(6):542-51.
International Search Report and Written Opinion issued in PCT/US2015/028917 dated Jul. 27, 2015.
International Search Report and Written Opinion issued in PCT/US2013/032693 dated Jul. 18, 2013.
International Search Report and Written Opinion issued in PCT/US2014/036680 dated Sep. 10, 2014.
International Search Report and Written Opinion issued in PCT/US2008/003493 dated Oct. 12, 2009.
International Search Report and Written Opinion issued in PCT/US2010/041560 dated Aug. 31, 2010.
International Search Report and Written Opinion issued in PCT/US2013/032650 dated Jul. 18, 2013.
International Search Report and Written Opinion issued in PCT/US2013/039748 dated Sep. 25, 2013.
International Search Report issued in PCT/US2003/027105 mailed May 5, 2004.
International Search Report and Written Opinion issued in PCT/US2004/028162 mailed Feb. 22, 2005.
International Search Report and Written Opinion issued in PCT/US2005/019870 mailed Oct. 14, 2005.
International Search Report and Written Opinion issued in PCT/US2006/012902 mailed Jul. 7, 2008.
International Search Report and Written Opinion issued in PCT/US2006/034374 mailed Jun. 16, 2008.
International Search Report and Written Opinion issued in PCT/US2007/016309 mailed Sep. 16, 2008.
International Search Report and Written Opinion issued in PCT/US2007/005073 mailed Oct. 29, 2007.
International Search Report and Written Opinion issued in PCT/US2007/025833 mailed Sep. 11, 2008.
International Search Report and Written Opinion issued in PCT/US2008/013319 mailed Apr. 8, 2009.
International Search Report and Written Opinion issued in PCT/US2011/025064 mailed Nov. 9, 2011.
Iwata et al., "Demineralized bone matrix and native bone morphogenetic protein in orthopaedic surgery," 2002, *Clinical Orthopaedics and Related Research* 395:99-109.
Izumo et al., "Lipophilic statins can be osteogenic by promoting osteoblastic calcification in a Cbfa1- and BMP-2-independent manner," 2001, *Methods and Findings in Experimental and Clinical Pharmacology* 23(7): 389-394.
Jahnke et al., "An in vitro Assay to Measure Targeted Drug Delivery to Bone Mineral," 2010, *ChemMedChem* 5(5):770-776.
Jiang et al., "Hedgehog signaling in development and cancer". 2008, *Developmental Cell* 15(6):801-812.
Johnson et al., "Novel oxysteols have pro-osteogenic and anti-adipogenic effects in vitro and induce spinal fusion in vivo," 2011, *Journal of Cellular Biochemistry* 112(6): 1673-1684.
Johnson et al., "LRP5 and Wnt signaling: a union made for bone," 2004, *Journal of Bone and Mineral Research* 19(11):1749-57.
Johnson et al., "Human bone morphogenetic protein allografting for reconstruction of femoral nonunion," 2000, *Clinical Orthopaedics and Related Research* 371:61-74.
Joseph S., et al., "Synthetic LXR ligand inhibits the development of atherosclerosis in mice," 2002, *Proceedings of the National Academy of Sciences* 99(11):7604-7609.
Jung et al., "First total synthesis of Zestobergesterol A and active structural analogues of the Xestobergesterols1," 1999, *Organic Letters* 1(10):1671-1674.

Juvet et al., "On the role of liver X receptors in lipid accumulation in adipocytes," 2003, *Molecular Endocrinology* 17(2):172-82.
Kadiyala et al., "Culture expanded canine mesenchymal stem cells possess osteochondrogenic potential in vivo and in vitro," 1997, *Cell Transplantation*, 6(2):125-134.
Kametani et al., "Stereocontrolled synthesis of 2-deoxycrustecdysone and related compounds," 1986, *The Journal of Organic Chemistry* 51(15):2932-2939.
Kaneko et al., "Induction of Intestinal ATP-binding cassette transporters by a phytosterol-derived liver x receptor agonist," 2003, *The Journal of Biological Chemistry* 278(38)36091-36098.
Kennell et al., "Wnt signaling inhibits adipogenesis through beta-catenin-dependent and -independent mechanisms," 2005, *Journal of Biological Chemistry* 280(25):24004-24010.
Kha et al., "Oxysterols regulate differentiation of mesenchymal stem cells: pro-bone and anti-fat," 2004, *Journal of Bone and Mineral Research* 19(5):830-840.
Kim et al., "Hedgehog signaling and osteogenic differentiation in multioptent bone marrow stromal cells are inhibited by oxidative stress," 2010, *Journal of Biological Chemistry* 111(5):1199-1209.
Kim et al., "ADD1/SREBP1 activates PPARgamma through the production of endogenous ligand," 1998, *Proceedings of the National Academy of Sciences* 95(8):4333-4337.
Kim et al., "Osteogenic oxysterol, 20(S)-Hydroxycholesterol, inhibits PPAR gamma expression and adipogenic differentiation of bone marrow stromal cells through a hedgehog-, wnt-, and MAPK-Dependent Mechanism," 2006, *Journal of Bone and Mineral Research* 21(1):S394.
Kim et al., "20(5)-hydroxycholesterol inhibits PPARgamma expression and adipogenic differentiation of bone marrow stromal cells through a Hedgehog-dependent mechanism," 2007, *Journal of Bone and Mineral Research* 22(11):1711-9.
Kim et al., "Identification of Two Brassinosteroids from the Cambial Region of Scots Pine (*Pinus silverstris*) by Gas Chromatography-Mass Spectometry, after Detection Using a Dwarf Rice Lamina Incilnation Bioassay," 1990, *Plant Physiology* 94(4):1709-1713.
Kim et al., "Osteogenic oxysterol, 20(S)-hydroxycholesterol, induces Notch target gene expression in bone marrow stromal cells," 2010, *Journal of Bone and Mineral Research* 25(4):782-795.
Komori et al., "Regulation of skeletal development by the Runx family of transcription factors," 2005, *Journal of Cellular Biochemistry* 95(3):445-453.
Koreeda et al., "Chirality transfer in stereoselective synthesis. A highly stereocontrolled synthesis of 22-hydroxylated steroid side chains via the [2,3]-Wittig rearrangmeent," 1986, *Journal of Organic Chemistry* 51(21):4090-4092.
Kurland et al., "Parathyroid hormone as a therapy for idiopathic osteoporosis in men: effects on bone mineral density and bone markers" 2000, *Journal of Clinical Endocrinology and Metabolism* 85(9):3069-3076.
Larsson et al. "Kinetics of GI progression in 3T6 and SV-3T3 cells following treatment by 25-hydroxycholesterol." 1986, *Cancer Research* 46(3):1233-1238.
Lefevre et al., "Adrenal cholesterol-binding protein: properties and partial purification," 1978, *FEBS Letters* 89(2): 287-292.
Lehmann et al., "Activation of the nuclear receptor LXR by oxysterols defines a new hormone response pathway," 1997, *Journal of Biological Chemistry* 272(6):3137-3140.
Li et al., "Delivering on the promise of bone morphogenetic proteins," 2001, *Trends in Biotechnology* 19(7):255-65.
Liao X. et al., "Aberrant activation of hedgehog signaling pathway in ovarian cancers: effect on prognosis, cell invasion and differentiation," 2009, *Carcinogenesis* 30(1):131-140.
Libby et al., "Inflammation in atherosclerosis," 2002, *Nature* 420:868-874.
Lieberman et al., "The role of growth factors in the repair of bone," 2002, *Journal of Bone and Joint Surgery* 84A(6):1032-1044.
Lin, "Bisphosphonates: A review of their pharmacokinetic properties," 1996, *Bone* 18(2):75-85.
Lin et al., "Pharmacokinetics of alendronate: an overview," 1999, *International journal of clinical practice. Supplement* 101:18-26.

(56) References Cited

OTHER PUBLICATIONS

Liu et al., "Interferon-inducible cholesterol-25-hydroxylase broadly inhibits viral entry by production of 25-hydroxycholesterol," 2013, *Immunity* vol. 38, pp. 92-105.
Liu et al., "The effect of simvastatin on the differentiation of marrow stromal cells from aging rats," 2009, *Die Pharmazie—An International Journal of Pharmaceutical Sciences* 64(1), pp. 43-48.
Long et al., "Genetic manipulation of hedgehog signaling in the endochondral skeleton reveals a direct role in the regulation of chondrocyte proliferation," 2001, *Development* 128(24):5099-5108.
Luhmann et al., "Bone targeting for the treatment of osteoporosis," 2012, *Journal of Controlled Release* 161(2):198-213.
Lum et al., "The hedgehog response network: sensors, switches, and routers," 2004, *Science* 304(5678):1755-1759.
Lyritis et al., "Bone anabolic versus bone anticatabolic treatment of postmenopausl osteoporosis," 2010, Annals of the New York Academy of Sciences 1205:277-283.
Maeda et al., "Simvastatin promotes osteoblast differentiation and mineralization in MC3T3-E1 cells," 2001, *Biochemical and Biophysical Research Communications* 280(3):874-877.
Maggio et al., "Marked decrease in plasma antioxidants in aged osteoporotic women: results of a cross-sectional study," 2003, *Journal of Clinical Endocrinology and Metabolism* 88(4):1523-1527.
Majors et al., "Characterization of human bone marrow stromal cells with respect to osteoblastic differentiation," 1997, *Journal of Bone and Joint Surgery* 15(4):546-557.
Makino et al., "Steroid conformations in solid and solution: stereoselectivity of Grignard addition to 20-keto steroids," 1978, *Journal of Organic Chemistry* 43(2): 276-280.
Manolagas et al., "Birth and death of bone cells: basic regulatory mechanisms and implications for the pathogenesis and treatment of osteoporosis," 2000, *Endocrine Reviews* 21(2):115-137.
Manolagas et al., "Cellular and molecular mechanisms of osteoporosis," 1998, *Aging Clinical and Experimental Research* 10(3):182-190.
Mazzocchi et al., "Photochemical additions of alkenes to phthalimides. Mechanistic investigation on the stereochemistry of alkene additions and the effect of aryl substituents on the regiochemistry of alkene additions," 1983, *Journal of Organic Chemistry* 48(18): 2981-2989.
Mbalaviele et al., "Beta-catenin and BMP-2 synergize to promote osteoblast differentiation and new bone formation," 2005, *Journal of Cellular Biochemistry* 94(2):403-418.
Meaney et al., "Evidence that the major oxysterols in human circulation originate from distinct pools of cholesterol: a stable isotope study," 2001, *Journal of Lipid Research* 42(1):70-78.
Melton et al., "How many women have osteoporosis now?," 1995, *Journal of Bone and Mineral Research* 10(2):175-177.
Meunier et al., "Osteoporosis and the replacement of cell populations of the marrow by adipose tissue: A quantitative study of 84 iliac bone biopsies," 1971, *Clinical Orthopedics and Related Research* 80:147-154.
Mezey et al. "Dispersed donor salivary gland cells are widely distributed in the recipient gland when infused up the ductal tree," 2009, *Biotechnic and Histochemistry* 84(6):253-260.
Mimaki et al., "Lipid and steroidal constituents of *Lilium auratum* var. platyphyllum and *L. tenuifolium*," 1989, *Phytochemistry* 28(12), 3453-3458.
Mitsunobu O., "The use of diethyl azodicarboxylate and triphenylphosphine in syntheses and transformation of natural products," 1981, *Synthesis* 01:1-28.
Miyamoto et al., "Prostaglandin E2-mediated anabolic effect of a novel inhibitor of phosphodiesterase 4, XT-611, in the in vitro bone marrow culture," 2003, *Journal of Bone and Mineral Research* 18(8):1471-1477.
Mody et al., "Oxidative stress modulates osteoblastic differentiation of vascular and bone cells," 2001, *Free Radical Biology and Medicine* 31(4):509-519.

Moerman et al., "Aging activates adipogenic and suppresses osteogenic programs in mesenchymal marrow stroma/stem cells: the role of PPAR-gamma2 transcription factor and TGF-beta/BMP signaling pathways," 2004, *Aging Cell* 3(6):379-89.
Montgomery et al., "A Novel Osteogenic Oxysterol Compound for Therapeutic Development to Promote Bone Growth: Activation of Hedgehog Signaling and Osteogenesis through Smoothened Binding," 2014, *Journal of Bone and Mineral Research* 29(8):1872-1885).
Morioka et al., "Design, synthesis and biological evaluation of novel estradio-biphosphonate conjugates as bone-specific estrogens," 2010, *Bioorganic and Medicinal Chemistry* 18(3):1143-1148.
Morisaki et al., "Studies on steroids. XLV. Synthesis of the four stereoisomers of 20,22-dihydroxycholesterol," 1977, *Chemical andPharmaceutical Bulletin* 25(10):2576-2583.
Morisaki et al., "Stereochemical specificity at carbon-20 and -22 of hydroxylated cholsterals for side-chain cleavage by adrenocortical cytochrome P-450sec," 1976, *FEBS Letters* 72(2):337-40.
Mullor et al., "Wnt signals are targets and mediators of Gli function," 2001, *Current Biology* 11(10):769-73.
Mullor et al., "Pathways and consequences: hedgehog signaling in human disease," 2002, *Trends in Cell Biology* 12(12):562-569.
Mundy et al., "Stimulation of bone formation in vitro and in rodents by statins," 1999, *Science* 286(5446):1946-1949.
Mundy et al., "Directions of drug discovery in osteoporosis," 2002, *Annual Review of Medicine* 53(1):337-354.
Muschitz et al., "Antiesorptives overlapping ongoing teriparatide treatment result in additional increases in bone mineral density," 2013, *Journal of Bone and Mineral Research* 28(1):196-205.
Myers et al., "Hedgehog pathway modulation by multiple lipid binding sites on the smoothened effector of signal response," 2013, *Development Cell* 26(4):346-357.
Nachtergaele et al., "Oxysterols are allosteric activators of the oncoprotein Smoothened," 2012, *Nature Chemical Biology* 8(2):211-220.
Nachtergaele et al., "Structure and function of the Smoothened extracellular domain in vertebrate Hedgehog signaling," 2013, *eLife* 2:e01340.
Nagahisa et al., "Acetylenic mechanism-based inhibitors of cholesterol side chain cleavage by cytochrome P-450scc," 1983, *Journal of Biological Chemistry* 258(11):6721-6723.
Nagano et al., "Chemistry and biochemistry of Chinese drugs, Part II—Hydroxylated sterols, cytotoxic towards cancerous cells: synthesis and testing," 1977, *Journal of Chemical Research* (M) 2522-2571.
Nagano et al., "Chemistry and biochemistry of Chinese drugs, Part II—Hydroxylated sterols, cytotoxic towards cancerous cells: synthesis and testing," 1977, *Journal of Chemical Research (Suppl.)* 218.
Nakamura et al., "Stimulation of bone formation by intraosseous application of recombinant basic fibroblast growth factor in normal and ovariectomized rabbits," 1997, *Journal of Orthopaedic Research* 15(2):307-313.
Nasim et al., "3-O-Phosphate ester conjugates of 17-beta-O-1,3,5(10)-estratriene as novel bone-targeting agents," 2010, *Bioorganic and Medicinal Chemistry Letters* 20:7450-7453.
Nedelcu et al., "Oxysterol binding to the extracellular domain of Smoothened in Hedgehod signaling," 2013, *Nature chemical biology* 9(9):557-564.
Nelson et al., "The oxysterol, 27-hydroxycholesterol, links cholesterol metabolism to bone homeostasis through its actions on the estrogen and liver x receptors," 2011, *Endocrinology* 152(12):4691-4705.
Nickolson et al., "Stereospecific synthesis of (20S,22R)-17α,20,22-trihydroxycholesterol and (20S,22S)-17a,20,22-trihydroxycholesterol," 1972, *Journal of Organic Chemistry* 37(13), 2119-2127.
Nishio et al., "3-hydroxy-3-methylglutaryl coenzyme A reductase inhibitor impairs cell differentiation in cultured adipogenic cells (3T3-L1)." 1996, *European Journal of Pharmacology* 301(1):203-206.

(56) References Cited

OTHER PUBLICATIONS

Olkkonen et al., "Oxysterols and oxysterol binding proteins: role in lipid metabolism and atherosclerosis," 2004, *Annals of Medicine* 36(8):562-572.
Otto et al., "Cbfa1, a candidate gene for cleidocranial dysplasia syndrome, is essential for osteoblast differentiation and bone development," 1997, *Cell* 89(5):765-771.
Panakova et al., "Lipoprotein particles are required for hedgehog and wingless signaling," 2005, *Nature* 435:58-65.
Parhami et al., "Lipid oxidation products have opposite effects on calcifying vascular cell and bone cell differentiation. A possible explanation for the paradox of arterial calcification in osteoporotic patients," 1997, *Arteriosclerosis, thrombosis, and vascular biology* 17(4):680-687.
Parhami et al., "Role of the cholesterol biosynthetic pathway in osteoblastic differentiation of marrow stromal cells," 2002, *Journal of Bone and Mineral Research* 17(11):1997-2003.
Parish et al., "Side-chain oxysterol regulation of 3-hydroxy-3-methylglutaryl coenzyme A reductase activity," 1995, *Lipids* 30:247-251.
Parish et al., "Regulation of 3-hydroxy-3-methylglutaryl coenzyme A reductase activity by side-chain oxysterols and their derivatives," 1999, *Critical Reviews in Biochemistry & Molecular Biology* 34(4):265-272.
Peacock C. et al., "Hedgehog signaling maintains a tumor stem cell compartment in multiple myeloma," 2007, *Proceedings of the National Academy of Sciences* 104(10):4048-4053.
Peet et al., "The LXRs: a new class of oxysterol receptors," 1998, *Current Opinion in Genetics & Development* 8(5):571-575.
Peng et al., "Antiatherosclerotic effects of a novel synthetic tissue-selective steroidal liver X receptor agonist in low-density lipoprotein receptor-deficient mice," 2008, *Journal of Pharmacology and Experimental Therapeutics* 327(2):332-342.
Pezacki et al., "Transcriptional profiling of the effects of 25-hydroxycholesterol on human hepatocyte metabolism and the antiviral state it conveys against the hepatitis C virus," 2009, *BMC Chemical Biology* 9(2):1-15.
Phelan C. et al., "Selective partial agonism of liver X receptor a is related to differential corepressor recruitement," 2008, *Molecular Endocrinology* 22(10): 2241-2249.
Pikuleva et al., "Putative Helix F Contributes to Regioselectivity of Hydroxylation in Mitochondrial Cytochrome P450 27A1," 2001, *Biochemistry* 40(25):7621-7629.
Pittenger et al., "Multilineage potential of adult human mesenchymal stem cells," 1999, *Science* 284(5411):143-147.
Porter J. et al., "Cholesterol modification of Hedgehog signaling proteins in animal development," 1996, *Science* 274:255-259.
Poza et al., "Synthesis and evaluation of new 6-hydroximinosteroid analogs as cytotoxic agents," 2007, *Bioorganic and Medicinal Chemistry* 15(14):4722-40.
Prockop DJ., "Marrow stromal cells as stem cells for nonhematopoietic tissues," 1997, *Science*, 276:71-74.
Quarto et al., "Bone progenitor cell deficits and the age-associated decline in bone repair capacity," 1995, *Calcified Tissue International* 56(2):123-129.
Rachner et al., "New Horizons in Osteoporosis," 2011, *Lancet* 377(9773):1276-1287.
Raghow et al., "SREBPs: the crossroads of physiological and pathological lipid homeostasis," 2008, *Trends in Endocrinology and Metabolism* 19(2):65-73.
Raisz LG., "The osteoporosis revolution," 1997, *Annals of Internal Medicine* 126(6):458-462.
Raisz et al., "Pathgenesis of osteoporosis: concepts, conflicts, and prospects," 2005, *Journal of Clinical Investigation* 115(12):3318-3325.
Rao AS., (1991) Addition reactions with formation of carbon-oxygen bones: (1) General methods of epoxidation. Comprehensive Organic Synthesis, Pergamon Press, Eds. Trost BM, Fleming I. 7 (chapter 3.1); 376-380.
Rao et al., "Lovastatin-mediated G1 arrest is through inhibition of the proteosome, independent of hydroxymethyl glutarl-CoA reductase," 1999, *Proc. Natl. Acad. Sci.* 96: 7797-7802.
Rawadi et al., "BMP-2 controls alkaline phosphatase expression and osteoblast mineralization by a Wnt autocrine loop," 2003, *Journal of Bone and Mineral Research* 18(10):1842-53.
Reeve et al., "Treatment with parathyroid peptides and estrogen replacement for severe postmenopausal vertebral osteoporosis: prediction of long-term responses in spine and femu," 2001, *Journal of Bone and Mineral Metabolism* 19:102-114.
Rehman et al., "Antiviral drugs against hepatitus C virus," 2011, *Genetic Vaccines and Therapy* 9(11): 1-10.
Reinholz et al., "Bisphosphonates directly regulate cell proliferation, differentiation, and gene expression in human osteoblasts," 2000, *Cancer Research* 60(21):6001-6007.
Reszka et al., "Mechanism of action of bisphosphonates," 2003, *Current Osteoporosis Reports* 1(2):45-52.
Richardson et al., "Oxysterol-induced osteoblastic differentiation of pluripotent mesenchymal cells is mediated through a PKC-and PKA-dependent pathway," 2007, *Journal of Cellular Biochemistry* 100(5):1131-45.
Richardson et al. "Characterization of osteogenic oxysterols and their molecular mechanism(s) of action," 2005, *Journal of Bone and Mineral Research* 20(9):S414.
Rickard et al., "Induction of rapid osteoblast differentiation in rat bone marrow stromal cell cultures by dexamethasone and BMP-2," 1994, *Developmental Biology* 161(1):218-28.
Riggs et al., "The prevention and treatment of osteoporosis," 1992, *New England Journal of Medicine* 327(9):620-7.
Riobó et al., "Phosphoinositide 3-kinase and Akt are essential for Sonic Hedgehog signaling," 2006, *Proceedings of the National Academy of Sciences* 103(12):4505-10.
Rodan et al., "Therapeutic approaches to bone diseases," 2000 *Science* 289(5484):1508-1514.
Rodda et al., "Distinct roles for Hedgehog and canonical Wnt signaling in specification, differentiation and maintenance of osteoblast progenitors," 2006, *Development* 133(16):3231-44.
Roodman et al., "Bone Building with bortezomib," 2008, *Journal of Clinical Investigation* 118(2):462-464.
Ruan et al., "An improved synthesis of (20R,22R)-cholest-5-ene-3?,20,22-triol, and intermediate in steroid hormone formation and an activator of nuclear orphan receptor LXR?," 1999, *Steroids* 64(6):385-395.
Rubin, "Southwestern Internal Medical Conference: Treatment considerations in the management of age-related osteoporosis," 1999, *The American Journal of the Medical Sciences*, 318(3):158-170.
Rubin et al., "Targeting the Hedgehog pathway in cancer," 2006, *Nature reviews Drug discovery* 5(12):1026-1033.
Rudin et al., Treatment of medulloblatoma with Hedgehog pathway inhibitor GDC-0449, 2009, *New England Journal of Medicine* 361(12):1173-1178.
Russell, "Oxysterol biosynthetic enzymes," 2000, *Biochimica et Biophysica Acta* 1529:126-135.
Sagan et al., "The influence of cholesterol and lipid metabolism on host cell structure and hepatitis C virus replication," 2006, *Biochemistry and Cell Biology* 84(1):67-79.
Sammons et al., "The role of BMP-6, IL-6, and BMP-4 in mesenchymal stem cell-dependent bone development: effects on osteoblastic differentiation induced by parathyroid hormone and vitamin D3," 2004, *Stem Cells and Development*, 13(3):273-280.
Sanchez et al., "Inhibition of prostate cancer proliferation by interference with SONIC HEDGEHOG-GLI1 signaling," 2004, *Proceedings of the National Academy of Sciences* 101(34):12561-12566.
Sang et al., "Ectopic overexpression of adipogenic transcription factors induces transdifferentiation of MC3T3-E1 osteoblasts," 2005, *Biochemical and Biophysical Research Communications* 327(3): 811-819.
Schaafsma et al. "Delay of natural bone loss by higher intake of specific minerals and vitamins," 2001, *Critical Reviews in Food Science and Nutrition* 41(3):225-249.

(56) References Cited

OTHER PUBLICATIONS

Schambony A. et al., "Wnt-5A/Ror2 regulate expression of XPAPC through an alternative noncanonical signaling pathway," 2007, *Developmental Cell* 12(5):779-92.
Schmidt et al., "A 15-ketosterol is a liver x receptor ligand that suppresses sterol-responsive element binding proteing-2 activity," 2006, *Journal of Lipid Research* 47:1037-1044.
Schroepfer, "Oxysterols: modulators of cholesterol metabolism and other processes," 2000, *Physiological Reviews* 80(1):361-554.
Scott et al., "Comparison of a novel oxsterol molecule and rhBMP2 fusion rates in a rabbit posterolateral lumbar spine model," 2015, *The Spine Journal* 15:733-742.
Semb, "Isozymes of bone esterases," 1970, *Calcified Tissue Research* 6(1):77-80.
Seo et al., "Activated liver X receptors stimulate adipocyte differentiation through induction of peroxisome proliferator-activated receptor gamma expression," 2004, *Molecular and Cellular Biology* 24(8):3430-44.
Shan et al., "Chromatographic behavior of oxygenated derivatives of cholesterol," *Steroids* 68(3):221-233.
Shaw et al., "The Sonic Hedgehog pathway stimulates prostate tumor growth by paracrine signaling and recapitulates embryonic gene expression in tumor myofibroblasts". 2009, *Oncogene* 28(50):4480-4490.
Shea et al., "BMP treatment of C3H10T1/2 mesenchymal stem cells induces both chondrogenesis and ostiogenesis," *Journal of Cellular Biochemistry* 90(6):1112-1127.
Sheikh et al., "Mass spectometry in structural and stereochemical problems. CCXXX Preparation of 5a, 20a and 5a, 17a, 20a-cholestane-3b, 6a-diol. Electron impact induced framentation of steroidal D 17(20), D 20(21) and D 20(22) olefins," 1973, *Journal of Organic Chemistry* 38(20):3545-3553.
Shimaoka et al., "Recombinant growth/differentiation factor-5 (GDF-5) stimulates osteogenic differentiation of marrow mesenchymal stem cells in porous hydroxyapatite ceramic," 2004, *Journal of Biomedical Materials Research Part A* 68(1):168-176.
Shimizu et al., "20?, 22-Dihydroxycholesterol, an Intermediate in the Biosynthesis of Pregnenolone (3?-Hydroxypregn-5-en-20-one) from Cholesterol," 1962, *Journal of Biological Chemistry* 237(3): 699-702.
Shinoda et al., "HMG-CoA Reductase Inhibitor, Acceleration of Bone Formation with Satin," 2000, *Pharmacia* 649-650.
Shouhed et al., "Osteogenic oxysterols inhibit the adverse effects of oxidative stress on osteogenic differentiation of marrow stromal cells," 2005, *Journal of Cellular Biochemistry* 95(6):1276-1283.
Silva et al., "New approaches to the treatment of osteoporosis," 2011, *Annual Review of Medicine* 62:307-322.
Silva-Vargas et al., "Beta-catenin and Hedgehog signal strength can specify number and location of hair follicles in adult epidermis without recruitment of bulge stem cells," 2005, *Developmental Cell* 9(1):121-31.
Sohal et al., "Mechanisms of aging: an appraisal of the oxidative stress hypothesis," 2002, *Free Radical Biology and Medicine* 33(5):575-586.
Song et al., "Effect of simvastatin on bone morphogenetic protein-2 expression and alkaline phosphatase activity of bone marrow stromal cell," 2002, *Chinese Journal of Reparative and Reconstructive Surgery*, 16(6):384-387. Abstract Provided Only.
Sottero et al., "Cholesterol oxidation products and disease: an emerging topic of interest in medicinal chemistry," 2009, *Current Medicinal Chemistry* 16(6):685-705.
Spinella-Jaegle et al., "Sonic hedgehog increases the commitment of pluripotent mesenchymal cells into the osteoblastic lineage and abolishes adipocytic differentiation," 2001, Journal of Cell Science 114(11):2085-2094.
Spiro et al., "Spinal fusion with recombinant human growth and differentiation factor-5 combined with a mineralized collagen matrix," 2001, *The Anatomical Record* 263(4):388-395.

Stappenbeck et al., "Novel oxysterols activate the Hedgehod pathway and induce osteogenesis," 2012, *Bioorganic & Medicinal Chemistry Letters*, 22(18): 5893-5897.
Stein et al., "Molecular mechanisms mediating proliferation/differentiation interrelationships during progressive development of the osteoblast phenotype," 1993, *Endocrine Reviews* 14(4):424-442.
Steitz et al., "Smooth Muscle Cell Phenotypic Transition Associated With Calcification: Upregulation of Cbfa1 and Downregulation of Smooth Muscle Lineage Markers," 2001, *Circulation Research* 89:1147-1154.
Stewart al., "Expression of the developmental Sonic hedgehog (Shh) signalling pathway is up-regulated in chronic lung fibrosis and the Shh receptor patched1 is present in circulating T lymphocytes," 2003, *Journal of Pathology* 199:488-495.
St-Jacques et al., "Indian hedgehog signaling regulates proliferation and differentiation of chondrocytes and is essential for bone formation," 1999, *Genes and Development* 13:2072-2086.
Sugano et al., "Identification of intermediates in the conversion of cholesterol to pregnenolone with a reconstituted cytochrome P-450sec system: accumulation of the intermediate modulated by the adrenodoxin level," 1996, *Journal of Biochemistry* 120(4), pp. 780-787.
Suh et al., "Hedgehog signaling plays a conserved role in inhibiting fat formation," 2006, *Cell Metabolism* 3(1):25-34.
Supplementary European Search Report issued in EP 03749213.9 dated May 14, 2009.
Supplementary European Search Report issued in EP 06824888.9 dated Jun. 24, 2009.
Swarthout et al., "Parathyroid hormone-dependent signaling pathways regulating genes in bone cells," 2002, *Gene* 282(1-2):1-17.
Sydykov et al., "Synthesis of (20S)-propargyl-5-pregnene-3β,20-diol and its use in the preparation of C27-steroids with an oxidized side chain," 1976, *Bioorganicheskaya Khimiya* 2(11):1531-1537. English Abstract Provided Only.
Sydykov et al, "Partial synthesis of 20(R),22(R)-D 5-cholestene-3b,20,22-triol," 1977, *Izvestiya Akademiii Nauk SSSR, Seriya Khimicheskaya* 1:191-194.
Szendi et al., "1,5-Hydride shift in Wolff-Kishner reduction of (20R)-3?,20, 26-trihydroxy-27-norcholest-5-en-22-one; synthetic, quantum chemical, and NMR studies," 2002, *Steroids* 67:31-38.
Ta et al., "Osteosarcoma treatment: state of the art," 2009, *Cancer Metastasis Reviews* 28(1-2):247-263.
Taipale et al., "The Hedgehog and Wnt signalling pathways in cancer," 2001, *Nature* 411(6835):349-354.
Taylor et al., "24,25-Epoxysterol metabolism in cultured mammalian cells and repression of 3-hydroxy-3-methylglutaryl-CoA reductase," 1986, *Journal of Biological Chemistry* 261(32):15039-15044.
Teplyuk et al., "The osteogenic transcription factor runx2 controls genes involved in sterol/steroid metabolism, including CYP11A1 in osteoblasts," 2009, *Molecular Endocrinology* 23(6):849-861.
Thayer et al., "Hedgehog is an early and late mediator of pancreatic cancer tumorigenesis," 2003, *Nature* 425(6960):851-856.
Thies et al., "Recombinant human bone morphogenetic protein-2 induces osteoblastic differentiation in W-20-17 stromal cells," 1992, *Endocrinology* 130(3):1318-1324.
Tintut et al., "Multilineage Potential of Cells From the Artery Wall," 2003, *Circulation* 108(20):2505-2510.
Väänänen HK., "Mesenchymal stem cells," 2005, *Annals of Medicine* 37(7):469-479.
Valentin-Opran et al., "Clinical evaluation of recombinant human bone morphogenetic protein-2," 2002, *Clinical Orthopaedics and Related Research* 395:110-120.
Vedin et al., "The oxysterol receptor LXR inhibits proliferation of human breast cancer cells," 2009, *Carcinogenesis* 30(4):575-579.
Velgova et al., "On steroids. CXXVI. Further compounds with antisclerotization effect on *Pyrrhocoris apterus* L. larvae: structure and activity correlations," 1969, *Collections of Czechoslovak chemical communications* 34(11): 3354-3376.
Vescini et al., "PTH 1-84: bone rebuilding as a target for the therapy of severe osteoporosis." 2012, *Clinical Cases in Mineral and Bone Metabolism* 9(1):31-36.

(56) References Cited

OTHER PUBLICATIONS

Viccica et al., "Role of the cholesterol biosynthetic pathway in osteoblastic differentiation," 2006, *Journal of Endocrinological Investigation* 30(6S): 8-12.

Vine et al., "Dietary oxysterols are incorporated in plasma triglyceride-rich lipoproteins, incrase their susceptibility to oxidation and increase aortic cholesterol concentrations in rabbits," 1998, *Journal of Lipid Research* 38:1995-2004.

Von Hoff et al., "Inhibition of the Hedgehog pathway in advanced basal-cell carcinoma," 2009, *New England Journal of Medicine* 361:1164-1172.

Wada et al., "Calcification of Vascular Smooth Muscle Cell Cultures : Inhibition by Osteopontin," 1999, *Circulation Research* 84:166-178.

Wada et al., "Lack of Positive Correlation Between Statin Ue and Bone Mineral Density in Japanese Subjects With Type 2 Diabetes," 2000, *Archives of Internal Medicine* 160(18):2865.

Wang et al., "Lipid Clearing Agents in Steroid-Induces Osteoporosis," 1995, *Journal of the Formosan Medical Association=Taiwan yi zhi* 94(10): 589-592.

Wang et al., "The pathogenesis and prevention of steroid-induced osteonecrosis," 2000, *Clinical Orthopaedics and Related Research* 370(2000):295-310.

Wang et al., "Structure of the human smoothened receptor 7TM bound to an antitumour agent," 2013, *Nature* 497(7449):338-343.

Watanabe et al., "Stereoselective synthesis of (22R)- and (22S)- castasterone/ponasterone A hybrid compounds and evaluation of their molting hormone activity," 2004, *Steroids* 69(7):483-493.

Watson et al., "TGF-beta1 and 25-hydroxycholesterol stimulate osteoblast-like vascular cells to calcify," 1994, *Journal of Clinical Investigation* 93(5):2106-2113.

Westendorf et al., "Wnt signaling in osteoblasts and bone diseases," 2004, *Gene* 341:19-39.

Wiersig et al., "Stereospecific synthesis of the side chain of the steroidal plant sex hormone oogoniol," 1979, *Journal of Organic Chemistry* 44(19):3374-3382.

Wolf et al., "A broad-spectrum antiviral targeting entry of enveloped viruses," 2010, *Proceedings of the National Academy of Sciences* 107(7):3157-3162.

Woo et al., "Enhancement of bone growth by sustained delivery of recombinant human bone morphogenetic protein-2 in a polymeric matrix," 2001, *Pharmaceutical Research* 18(12):1747-1753.

Yamaguchi et al., "Regulation of osteoblast differentiation mediated by bone morphogenetic proteins, hedgehogs, and Cbfa1," 2000, *Endocrine Reviews* 21(4):393-411.

Yamaguchi et al., "Osteoporosis and Vascular Calcfication," 2002, *Clinical Calcium* 39-43. English Abstract Provided Only.

Yang et al., "Transcription factors in bone: developmental and pathological aspects," 2002, *Trends in Molecular Medicine* 8(7):340-5.

Yang et al., "Parathyroid hormone activates PKC-delta and regulates osteoblastic differentiation via a PLC-independent pathway," 2006, *Bone* 38(4):485-96.

Yao et al., "22R-hydroxycholesterol induces differentiation of human nt2 precursor (Ntera2/d1 teratocarcinoma) cells." 2007, *Neuroscience* 148(2):441-453.

Yao et al., "22R-Hydroxycholesterol protects neuronal cells from b-amyloid-induced cytotoxicity by binding β-amyloid peptide," 2002, *Journal of Neurochemistry* 83(5):1110-1119.

Yauch et al., "A paracrine requirement for Hedgehog signaling in cancer," 2008, *Nature* 455(7211):406-410.

Yauch et al., "Hedgehog overexpression is associated with stromal interactions and predicts for poor outcome in breast cancer," 2011, *Cancer Research* 71(11): 4002-4015.

Yeh et al., "Osteogenic protein-1 (op-1, bmp-7) induces osteoblastic cell differentiation to the pluripotent mesenchymal cell line c2c12," 2002, *Journal of Cell Biochemistry* 87(3): 292-304.

Yoon et al., "Osteoinductive molecules in orthopaedics: basic science and preclinical studies," 2002, *Clinical orthapaedics and related research* 395:33-43.

Yoshida et al., "Core-binding factor beta interacts with Runx2 and is required for skeletal development," 2002, *Nature Genetics* 32(4):633-8.

Yoshida et al., "Stimulation of bone formation and prevention of bone loss by prostaglandin E EP4 receptor activation," 2002, *Proceedings of the National Academy of Sciences* 99(7):4580-5.

Zanchetta et al., "Systematic effects on bone healing of a new hyaluronic acid-like bacterial exopolysaccharide," 2003, *Calcified Tissue International* 73:232-236.

Zander et al., "Chemistry and Biochemistry of Chinese Drugs. Part III. Mechanism of Action of Hydroxylated Sterols on Cultured Hepatoma Cells," 1977, *Journal of Chemical Research* (M)9:2572-2584.

Zander et al., "Chemistry and Biochemistry of Chinese Drugs. Part III. Mechanism of Action of Hydroxylated Sterols on Cultured Hepatoma Cells," 1977, *Journal of Chemical Research* (S)9:219.

Zelcer et al., "Liver X receptors as integrators of metabolic and inflammatory signaling," 2006, *Journal of Clinical Investigation* 116:607-614.

Zhang et al., "Cyclooxygenase-2 regulates mesenchymal cell differentiation into the osteoblast lineage and is critically involved in bone repair," 2002, *Journal of Clinical Investigation* 109(11):1405-1415.

Zhao et al., "E3 ubiquitin ligase Smurf1 mediates core-binding factor alpha1/Runx2 degradation and plays a specific role in osteoblast differentiation," 2003, *Journal of Biological Chemistry* 278(30):27939-44.

Zhao et al., "The zinc finger transcription factor Gli2 mediates bone morphogenetic protein 2 expression in osteoblasts in response to hedgehog signaling," 2006, *Molecular and Cellular Biology* 26(16):6197-6208.

Zimmerman et al., "Stereochemical effects in cyclopropane ring openings: biomimetic ring openings of all isomers of 22, 23-methylenecholesterol acetate," 1984, *Journal of the American Chemical Society* 106(19):5602-5612.

Ziros et al., "The bone-specific transcriptional regulator Cbfa1 is a target of mechanical signals in osteoblastic cells," 2002, *Journal of Biological Chemistry* 277(26):23934-23941.

Correa, C. (Jan. 2007). "Guidelines for the Examination of Pharmaceutical Patents: Developing a Public Health Perspective," WHO-ICTSD, UNCTAD, 65 pages.

Guan, Y. et al. (Jul.-Aug. 2000). "Synthesis of compound libraries based on 3,4-diaminocyclopentanol scaffolds," *J Comb Chem* 2(4):297-300.

Neale, J.R. et al. (Feb. 1, 2009, e-published Dec. 24, 2008). "Bone selective effect of an estradiol conjugate with a novel tetracycline-derived bone-targeting agent," *Bioorg Med Chem Lett* 9(3):680-683.

Petrova, N.S. et al. (Mar. 2012, e-published Nov. 10, 2011). "Carrier-free cellular uptake and the gene-silencing activity of the lipophilic siRNAs is strongly affected by the length of the linker between siRNA and lipophilic group," *Nucleic Acid Res* 40(5):2330-2344.

* cited by examiner

BONE-SELECTIVE OSTEOGENIC OXYSTEROL-BONE TARGETING AGENTS

BACKGROUND OF THE INVENTION

The present invention is relevant to the field of treatment of bone disorders.

SUMMARY OF THE INVENTION

An embodiment of the present invention is a composition comprising an oxysterol-bone targeting agent compound, such as set forth herein, for example, an Oxy133-tetracycline derivative compound. An oxysterol-bone targeting agent compound can include a compound of the formula

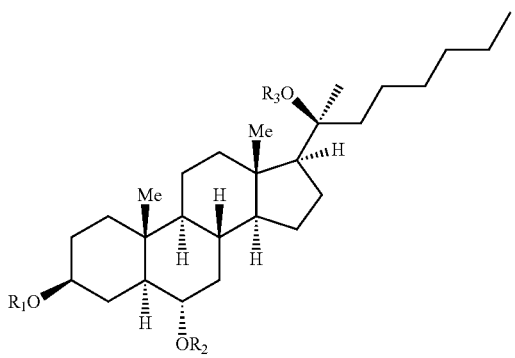

with $R_1$, $R_2$, and $R_3$ being independently hydrogen,

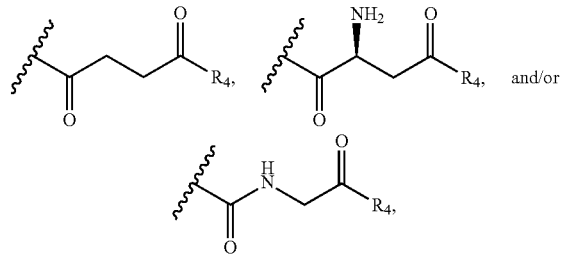

and with $R_4$ being

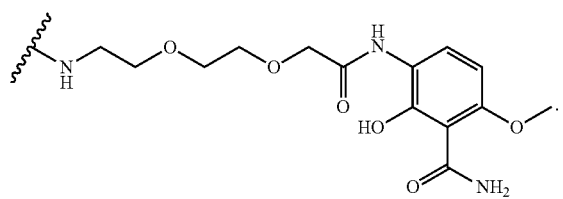 [SMILES: *NCCOCCOCC(=O)Nc1ccc(OC)c(C(N)=O)c1O]

At least one of $R_1$, $R_2$, and $R_3$ is not hydrogen, and when $R_1$ and $R_3$ are hydrogen, then $R_2$ is not

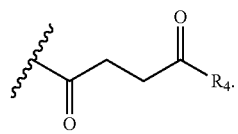

For example, $R_1$, $R_2$, and/or $R_3$ can be hydrogen. For example, $R_1$, $R_2$, and/or $R_3$ can be not hydrogen. $R_3$ can be hydrogen. $R_2$ can be hydrogen and $R_3$ can be hydrogen. $R_1$ can be hydrogen and $R_3$ can be hydrogen. $R_3$ can be hydrogen and $R_1$ can be not hydrogen and $R_2$ can be not hydrogen. $R_3$ can be hydrogen and $R_1$ and $R_2$ can each be

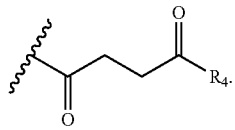

$R_3$ can be hydrogen and $R_1$ and $R_2$ can each be

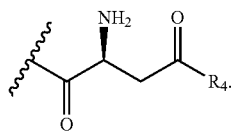

$R_3$ can be hydrogen and $R_1$ and $R_2$ can each be

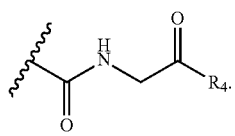

$R_1$, $R_2$, and $R_3$ can each be

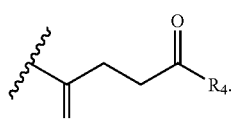

$R_1$, $R_2$, and $R_3$ can each be

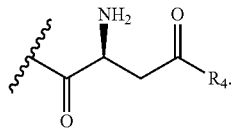

$R_1$, $R_2$, and $R_3$ can each be

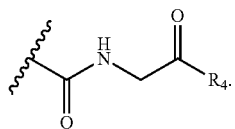

For example, the compound can be
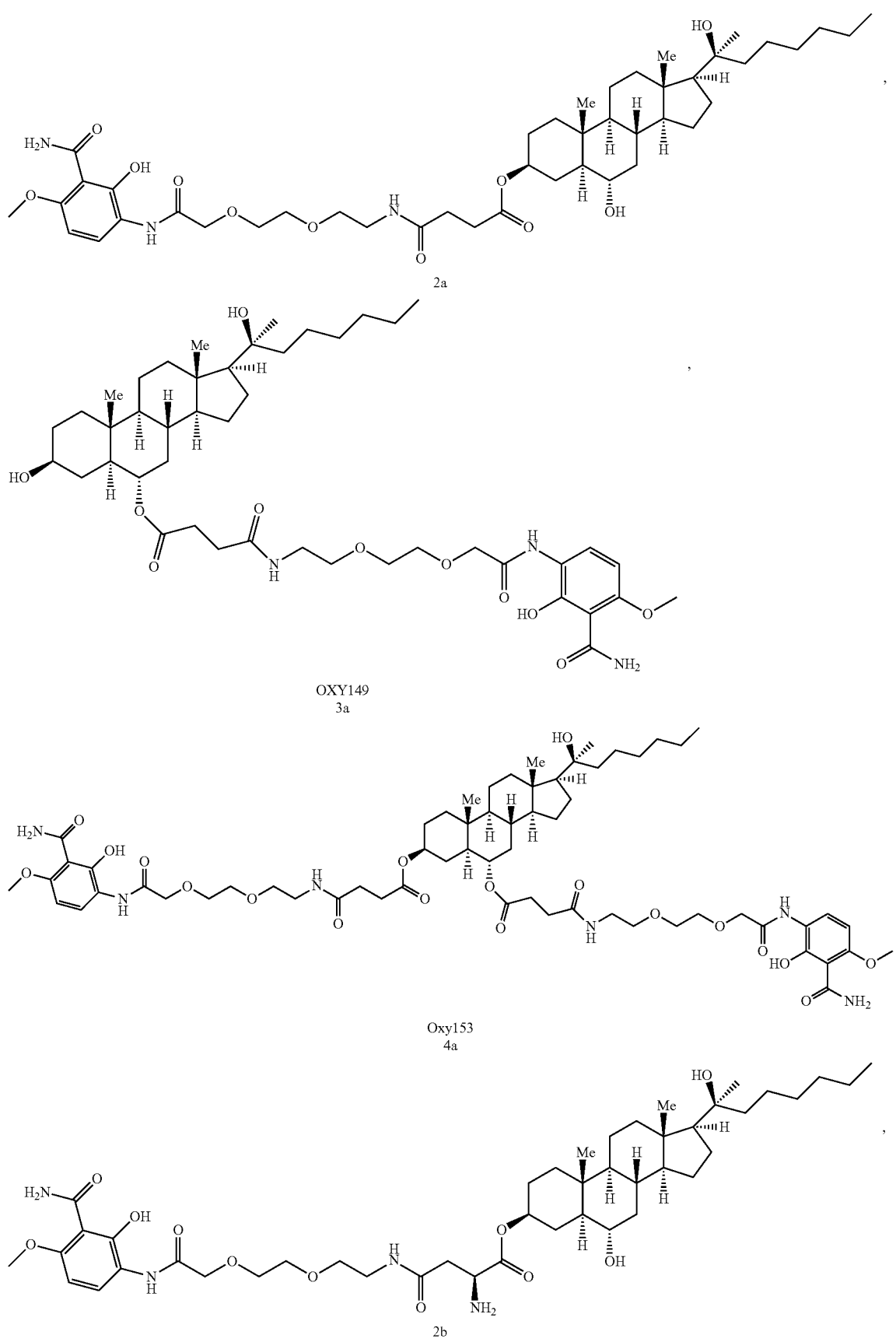

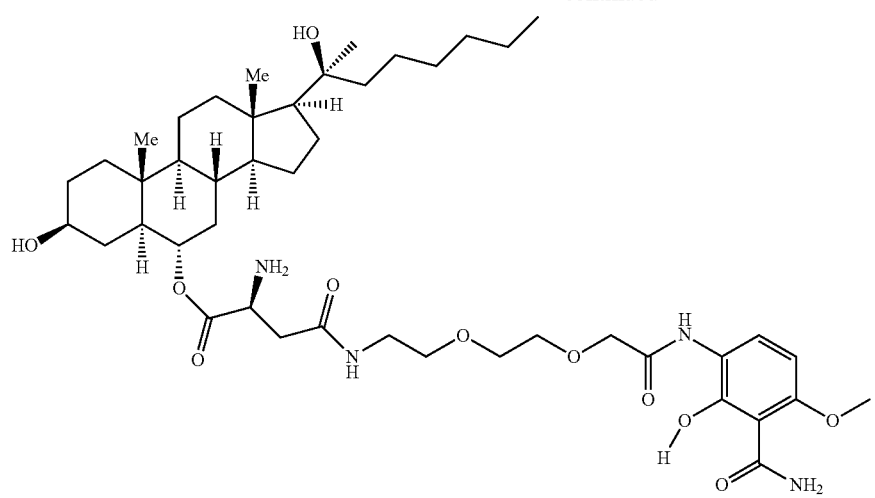
Oxy154
3b
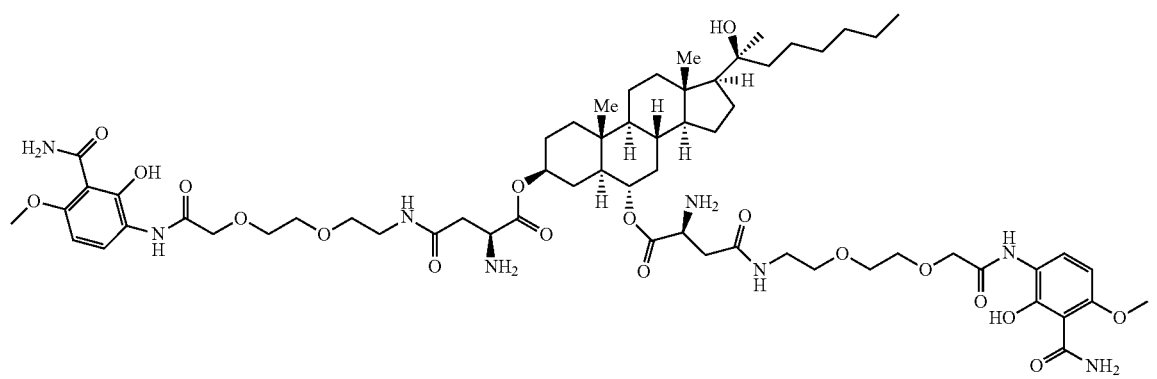
Oxy155
4b
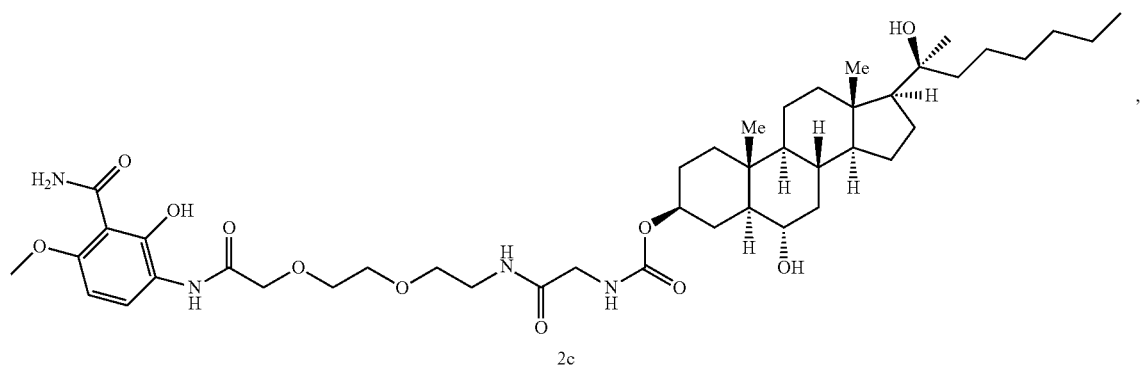
2c

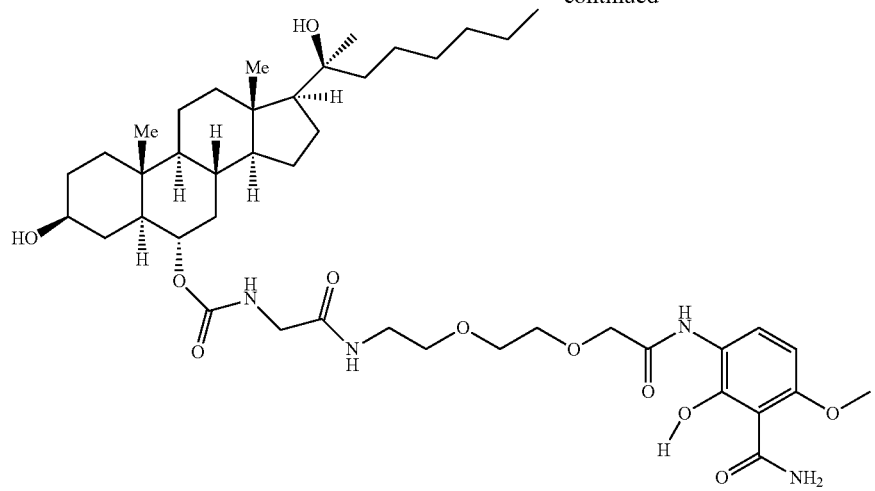
3c
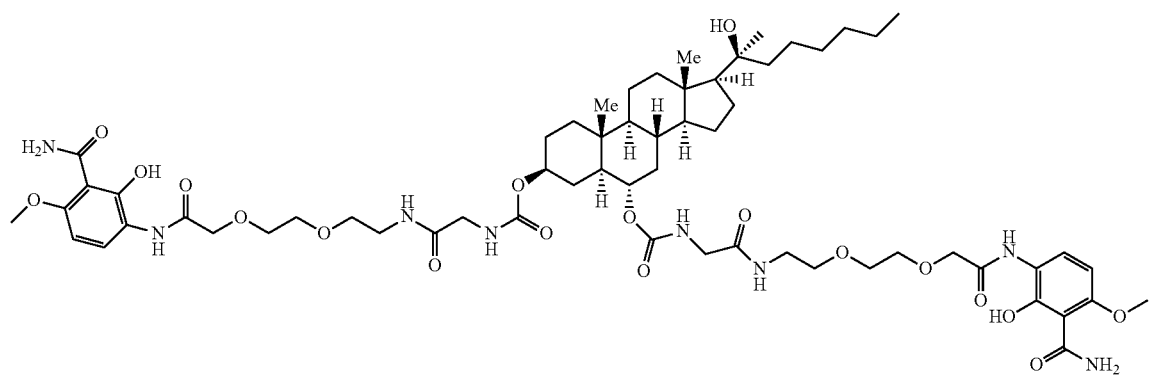
4c
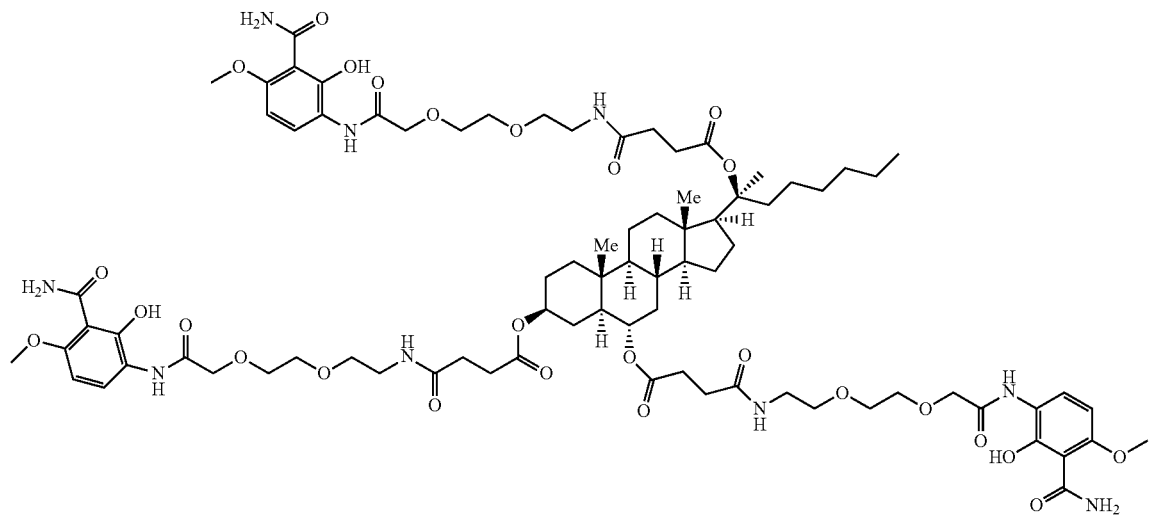
7a

-continued

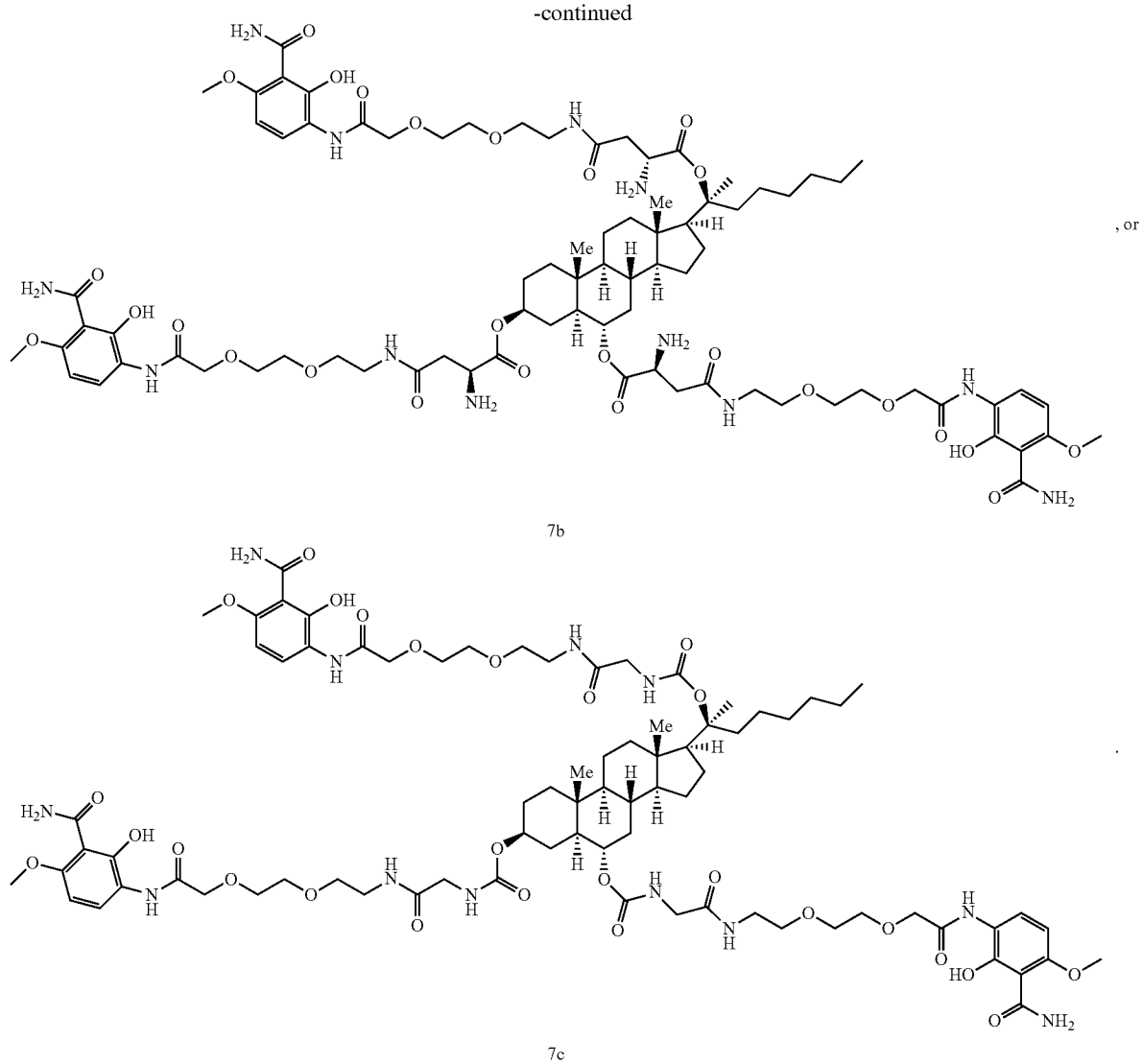

7b

7c

The composition can include a pharmaceutically acceptable carrier or diluent and can be a pharmaceutical formulation. A method of the present invention includes the administration and/or delivery, locally and/or systemically, of an oxysterol-bone targeting agent compound into a subject, which can be a person or an animal, for the treatment of a bone disorder including, but not limited to, a bone fracture, osteoporosis, and/or osteopenia. A method of the present invention includes in vitro treatment of osteoblast progenitor cells with an oxysterol-bone targeting agent compound, and their (the osteoblast progenitor cells) subsequent local and/or systemic administration and/or delivery into a subject, which can be a person or an animal, for the treatment of a bone disorder including, but not limited to, a bone fracture, osteoporosis, and/or osteopenia. A method of the present invention includes making and/or administering, such as locally and/or systemically, to a cell, an oxysterol-bone targeting agent compound, for example, so that a Hedgehog signaling pathway in the cell is stimulated. The cell can be part of a tissue or an organ, and the compound can be administered in vivo (locally or systemically). A method according to the present invention includes treating a subject, which can be a human or an animal, for example, that would benefit from therapeutic activation of a Hedgehog signaling pathway in a tissue or an organ, by treating a cell of the tissue or organ by administering an oxysterol-bone targeting agent to the cell, so that the Hedgehog signaling pathway of the tissue or organ is stimulated.

DETAILED DESCRIPTION

Figure 1:
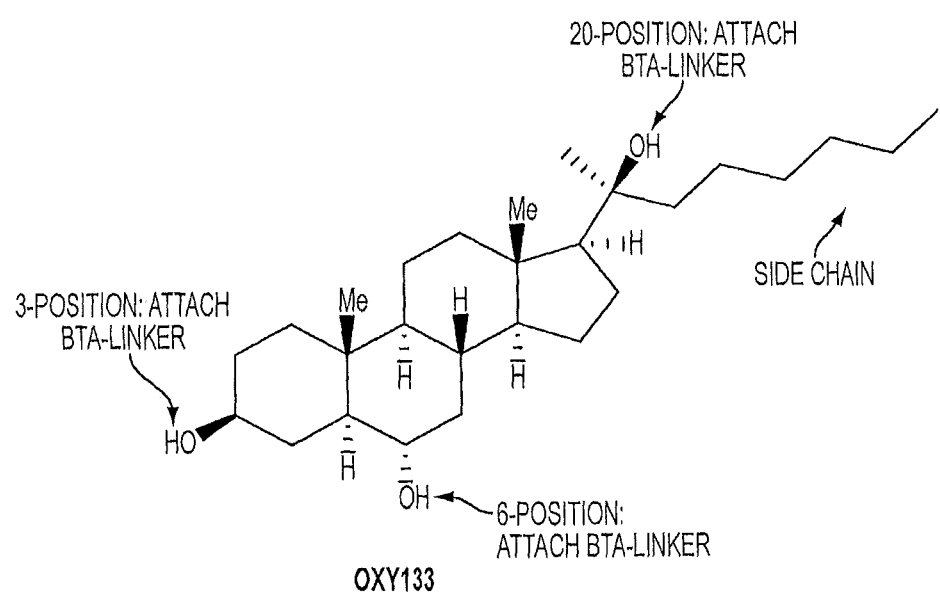
FIG. 1 shows the structure of the Oxy133 compound, with the sites of BTA-linker attachments.

Embodiments of the invention are discussed in detail below. In describing embodiments, specific terminology is employed for the sake of clarity. However, the invention is not intended to be limited to the specific terminology so selected. A person skilled in the relevant art will recognize that other equivalent parts can be employed and other methods developed without parting from the spirit and scope of the invention.

This application claims the benefit of U.S. Provisional Application No. 61/818,825, filed May 2, 2013, which is hereby incorporated by reference in its entirety.

Osteoporosis is a common metabolic bone disease affecting more than 10 million Americans, nearly 50% of the elderly female and more than 10% of the elderly male population (T. D. Rachner et al., *Lancet* 2011, 377, 1276-1287; B. C. Silva et al., *Annu. Rev. Med.* 2011, 62, 307-322; G. P. Lyritis et al., *Ann. N.Y. Acad. Sci.* 2010, 1205, 277-283; S. Khosla et al., *J. Clin. Endocrinol. Metab.* 2012, 97, 2272-2282; T. J. Aspray et al., *Maturitas* 2012, 71, 76-78; D. M. Black et al., *N. Engl. J. Med.* 2012, 366, 2051-2053). Osteopenia (reduced bone mass), a major risk factor for developing osteoporosis, is even more common, affecting 34 million Americans (Silva; Lyritis; Khosla; Aspray). Bone fractures are a widespread complication of osteoporosis and osteopenia resulting in significant socio-economic cost, such as hospitalization and disability, and very often they are the cause of deterioration and death of otherwise healthy and functioning elderly individuals (Lyritis). Age-related osteoporotic bone loss and its resulting complications cause significant morbidity and mortality in the aging population (Rachner; Silva; Lyritis; Khosla; Aspray; Black). Among two possible therapeutic strategies for osteoporosis, prevention of bone loss/resorption or stimulation of bone growth, anti-resorptive therapy with bisphosphonate drugs is more established (Khosla; M. Sharpe, et al., *Drugs,* 2001, 61, 999-1039). Nearly all current therapies for osteoporosis as well as the majority of potential new treatments under clinical investigation aim to reduce the level of bone resorption in osteoporotic patients (Khosla; Aspray; Black; L. Brewer et al., *Eur. J. Clin. Pharmacol.* 2011, 67, 321-331). Therapies on the market or in clinical trials that target mechanisms of bone resorption include bisphosphonates (e.g., Alendronate), Denosumab (Prolia), Zolendronic Acid (Reclast), Odanacatib, and Saracatinib (Brewer). Anti-resorptive drug therapy has been most effective in treating early and mild cases of the disease, unlike advanced osteoporosis where a massive loss of bone mineral density has already occurred (Khosla; Brewer).

Alternatively, bone anabolic agents can provide additional treatment options, particularly with advanced disease, and significantly improve osteoporosis management, in spite of a paucity of FDA approved drugs in this area (E. Canalis, *J. Clin. Endocrinol. Metab.* 2010, 95, 1496-1504). Currently, the only FDA approved bone anabolic agent available for treatment of severely osteoporotic patients is teriparatide (Forteo), a recombinant form of parathyroid hormone (PTH), which has to be administered intermittently, by daily injection (F. Vescini et al., *Clin. Cases Miner. Bone Metab.* 2012, 9, 31-36). Forteo can produce significant bone formation and reduce fracture risk, but its use is severely restricted due to safety concerns (Canalis; Vescini; R. Dimitriou et al., *BMC Medicine* 2011, 9, 1-10). Due to adverse side effects, such as an increased risk of osteosarcoma, drug labeling for Forteo is highly restricted with respect to patient population and duration of use (less than 24 months). Other anabolic agents under clinical investigation include calcilytic drugs that stimulate endogenous intermittent PTH secretion, and inhibitors of antagonists of Wnt signaling (Rachner; Dimitriou).

In patients with mild osteoporosis, bisphosphonate drugs (e.g., alendronic acid, Fosamax) can produce significant benefits such as improved bone density and reduced fracture risk (Khosla; Sharpe). However, bisphosphonate drugs, including alendronic acid, display low oral bioavailability, 0.6-0.7% on average, even when ingested under fasting conditions. Drug intake together with meals and beverages (other than water) further reduces the bioavailability, and intake under fasting conditions entails serious upper GI tract irritation in a majority of patients (Aspray). Hence, repeated, often daily, oral dosing under fasting conditions is necessary to maximize delivery of the bisphosphonate drugs to what is pharmacologically achievable while more than 99% of the dose cannot be absorbed and is ejected from the body unused. The fraction of bisphosphonate drug that can be absorbed, can rapidly partition in the human body, with about 50% of the drug binding to bone surface and the rest being excreted unchanged via the kidneys. The physicochemical basis of low oral absorption is thought to be associated with the negatively charged phosphonate moieties that are unavoidably part of all bisphosphonate drugs. To overcome this drawback, strategies have been investigated, including prodrug approaches with fatty acid and bile acid conjugation that aim to mask the phosphonate charge effect (P. Vachal et al., *J. Med. Chem,* 2006, 49, 3060-3063; O. Bortolini et al., *Euro, J. Med Chem.* 2012, 52, 221-229).

Biologics are commonly employed to promote bone growth in medical applications including fracture healing and surgical management of spinal disorders (E. E. Johnson et al., *Clin. Orthop. Relat. Res,* 2000, 371, 61-74; G. R. Mundy, *Annu. Rev. Med.* 2002, 53, 337-54; G. A. Rodan et al., *Science* 2000, 289, 1508-14; S. T. Yoon, *Clin. Orthop. Relat. Res.* 2002, 395, 33-43). Spine fusion is often performed by orthopedic surgeons and neurosurgeons alike to address degenerative disc disease and arthritis affecting the lumbar and cervical spine. Historically, autogenous bone graft, commonly taken from the iliac crest of the patient, has been used to augment fusion between vertebral levels. However, the associated donor site morbidity, increased operating time, and increased blood loss associated with harvesting autogenous bone graft (E. D. Arrington et al., *Clin. Orthop. Relat. Res.* 1996, 329, 300-9.; A. R. Vaccaro et al., *Spine J.* 2002, 2, 206-15; J. A. Rihn et al., *Spine* 2010, 35, 1629-39) has provided incentive to find a safe and effective alternative.

Recombinant human bone morphogenetic protein-2 (rh-BMP-2) is commonly used to promote spine fusion in humans. Its use was approved in 2002 by the US Food and Drug Administration (FDA) for single-level anterior lumbar interbody fusion (M. Mitka, *JAMA* 2011, 306, 1311-2.). The use of rhBMP-2 has increased significantly since this time and indications for its use have expanded to include posterior lumbar spinal fusion as well cervical spine fusion. Despite the efficacy of rhBMP-2, recent reports have called into question its safety when employed during spine fusion surgery. Reported complications have included seroma formation, soft tissue swelling, vertebral osteolysis, ectopic bone formation, retrograde ejaculation, and carcinogenicity (K.-U. Lewandrowski, *Spine J.* 2007, 7, 609-14; D. A. Wong, *Spine J.* 2008, 8, 1011-8; J. D. Smucker et al., *Spine*, 2006, 31, 2813-9; E. J. Carragee, *Spine J.*, 2011, 11, 471-91). Moreover, airway edema has been observed with its use in the cervical spine, prompting the FDA to issue a Public Health Notification warning for its use in cervical spine operations.

In an embodiment of the invention, novel molecules are synthesized that are combinations of an osteogenic oxysterol, Oxy133, with a bone targeting agent (BTA). When administered systemically these molecules may selectively home to bone tissue and enhance bone formation. These molecules can be used as bone anabolic agents for the treatment of osteoporosis. Bone targeted osteogenic oxysterols are not expected to have significant toxic or immunogenic effects when administered systemically.

The cellular differentiation of multipotent mesenchymal stem cells (MSCs) into bone forming osteoblasts can constitute a driver of anabolic bone growth. Certain naturally occurring oxysterols can induce osteogenic while preventing adipogenic differentiation of MSCs in vitro, and can stimulate localized bone formation in a rat calvarial defect model in vivo (T. L. Aghaloo et al., *J. Orthop. Res.* 2007, 25, 1488-1497). The synthesis and characterization of novel semi-synthetic oxysterols with greater osteogenic activity than the naturally occurring oxysterols when used in vitro or in a rat spine fusion model in vivo has been reported (J. S. Johnson et al., *J. Cell. Biochem.* 2011, 112, 1673-1684; S. R. Montgomery et al., *J. Bone Miner. Res.* 2014, accepted for publication). In an embodiment of the present invention, novel osteogenic oxysterols as bone anabolic agents in the context of systemic dosing (iv (intravenous), ip (intraparenteral), or oral), as required for the treatment of osteoporosis, are set forth.

Oxysterols, products of cholesterol oxidation, are formed in vivo, and have been implicated in various biologic processes including cellular differentiation and cholesterol metabolism (G. J. Schroepfer, *Physiol. Rev.* 2000, 80, 362-554; S. Gill et al., *Prog. Lipid Res.* 2008, 47, 391-404; B. Sottero et al., *Curr. Top. Med. Chem.* 2009, 16, 685-705). Naturally occurring oxysterols, which are found in human and animal circulation and in various tissues, can have bone-forming, osteogenic properties (J. R. Dwyer et al., *J. Biol. Chem*, 2007, 282, 8959-8968; W. K. Kim et al., *J. Bone Miner. Res*, 2010, 25, 782-795; H. T. Kha et al., *J. Bone Miner. Res*, 2004, 19, 830-840; J. A. Richardson et al., *J. Cell. Biochem.* 2007, 100, 1131-1145; C. M. Amantea et al., *J. Cell. Biochem.* 2008, 105, 424-436). The administration of these oxysterols to pluripotent mesenchymal osteoprogenitor cells, including bone marrow stromal cells (mesenchymal stem cells, MSC) and embryonic fibroblasts, can cause robust osteogenic differentiation and formation of an abundant mineralized bone matrix in vitro (Kim; Kha; Richardson). Without being bound by theory, these effects may be mediated in part through activation of the Hedgehog (Hh) signaling pathway independent of the classical Hh proteins (Dwyer). A family of more potent oxysterols can possess osteogenic and anti-adipogenic activity superior to the naturally occurring oxysterols from which they are derived (J. S. Johnson; Montgomery). Such molecules can display potent osteogenic activity in vitro and stimulate robust bone formation and spine fusion in vivo. They are not expected to elicit significant immunogenic responses (J. S. Johnson; Montgomery).

Bone health in adult life depends on a coordinated balance of anabolic and catabolic cellular activities of bone-forming osteoblasts and bone-resorbing osteoclasts, respectively. Multipotent mesenchymal stem cells (aka marrow stromal cells, MSCs) form the precursor population for a variety of cell types, including osteoblasts and adipocytes. Formation of new bone is driven by osteoblastic differentiation of MSCs, a process that can be disrupted by a number of factors. Aging, disease and lifestyle factors such as tobacco and alcohol abuse tend to push MSC populations toward adipogenesis at the expense of osteoblast differentiation, resulting in osteopenic disorders that often lead to full-fledged osteoporosis and impaired fracture repair (A. Sloan et al., *The Surgeon*, 2010, 8, 111-116; D. A. Chakkalakal, *Alcohol Clin. Exp. Res.* 2005, 12, 2077-2090). The mechanisms behind lineage-specific differentiation of MSC can be important. Factors can stimulate osteoblast formation while inhibiting adipogenesis.

Naturally-occurring oxysterols can act as drug-like molecules with an effect on MSCs and other multipotent mesenchymal cells (Aghaloo; Dwyer; Kim; Kha; Richardson; Amantea). Oxysterols that occur in human circulation and various tissues can be short-lived intermediates in metabolic transformations of cholesterol to form steroid hormones and bile acids (Schroepfer). Beyond their role as passive metabolites, however, natural oxysterols can function as signaling molecules, capable of modulating a range of physiological phenomena, among them homeostasis of lipids as well as control over cellular states such as differentiation, inflammation and apoptosis (Gill). That is, oxysterols can play a role as regulators of tissue specific signaling. Early research on oxysterols considered their pathological contributions and assumed that all oxysterols have similar properties, regardless of their distinct chemical composition (Sottero). Oxysterol chemotypes can have more individualized characteristics that depend on the cellular context and the exact chemical composition of the oxysterol (S. Nachtergaele et al., *Nat. Chem. Biol.* 2012, 8, 211-220). Some oxysterols can promote oxidative stress (Sottero). However, osteogenic oxysterols can inhibit the adverse effects of oxidative stress on osteogenic differentiation of progenitor cells (D. Shouhed, *J. Cell. Biochem.* 2005, 95, 1276-1283). Some oxysterols are thought to be endogenous ligands of LXR receptors. However, the osteogenic activity of oxysterols may not be a consequence of LXR activation, but can be mediated through the activation of Hh signaling (Dwyer). The oxysterol-induced activation of Hh signaling can occur independent of Hh proteins and result in the activation of non-canonical Wnt and Notch signaling (Kha; Amantea). Baseline PKA/cAMP, PKC, MAPK, and PI3-Kinase signaling can be involved in mediating various aspects of the cellular responses to these oxysterols (Kha; Richardson). In spite of reported cytotoxicity of some oxysterols (Schroepfer), no toxic effects were found with osteogenic oxysterols in vitro when dosed at 1-20 μM with osteoprogenitor cells or, in vivo, during local administration in the rat spine fusion model (40 mg), or, in mice, dosed ip at 50 mg/kg 3 times per week for a total of 8 weeks as determined by the absence of behavioral changes.

Naturally-occurring oxysterols, 20(S)-hydroxycholesterol, 22(S)-hydroxycholesterol and 22(R)-hydroxycholesterol can be used as potential osteogenic agents (Kha; Richardson; Amantea). A series of potent osteogenic oxysterol analogues was identified, which are efficacious both in vitro and in vivo. Members of this family of semi-synthetic oxysterols induce robust bone formation and spine fusion in rats when applied locally between transverse processes via a collagen sponge (T. S. Johnson). The compound OXY133 is an analog in the series with enhanced osteogenic activity (FIG. 1) (Montgomery). Oxy133 can induce osteogenesis in cultured human primary mesenchymal stem cells and induce spine fusion in rats in an accelerated manner compared to other analogues. Oxy133 can induce robust osteogenesis in non-rodent models of bone disease such as rabbit spine fusion and rabbit calvarial defect models. Oxy133 is a drug development candidate for local administration with potential application in spine fusion and repair of non-union fractures. However, when contemplating systemic administration of oxysterols like Oxy133 as a potential anabolic factor to stimulate bone formation in osteoporosis, one has to consider their short half-lives (<5 min) in human liver microsomes (HLM), and tissue distribution that does not necessarily favor deposition in bone tissue. Furthermore, due to the possible mechanism of osteogenesis, a transient activation of the Hh-pathway in MSCs, increasing selectivity for bone tissue while minimizing the exposure to other tissues may be prudent. This can be accomplished by linking a bone targeting agent (BTA) to the oxysterol molecule that selectively delivers it to bone.

Bone specific drug delivery is not only applicable to drugs marginally acceptable for bone disease (e.g., estradiol and diclofenac) to increase efficacy, minimize side effects and allow for appropriate dosing (S. Zhang et al., *Chem. Soc. Rev.* 2007, 36, 507-31). In an embodiment of the present invention, the concept of bone specific drug delivery is applied to osteogenic molecules not previously tested for systemic bone disease, to render them as effective treatments for osteoporosis. Oxysterol-based agonists of Hh signaling with osteogenic properties can fall into this category. Bone specific drug delivery agents can be attached to their drug molecules via hydrolysable linker bonds (M. W. Orme et al., *Bioorg. Med. Chem. Lett.* 1994, 4, 1375-1380; Zhang).

Figure 2:
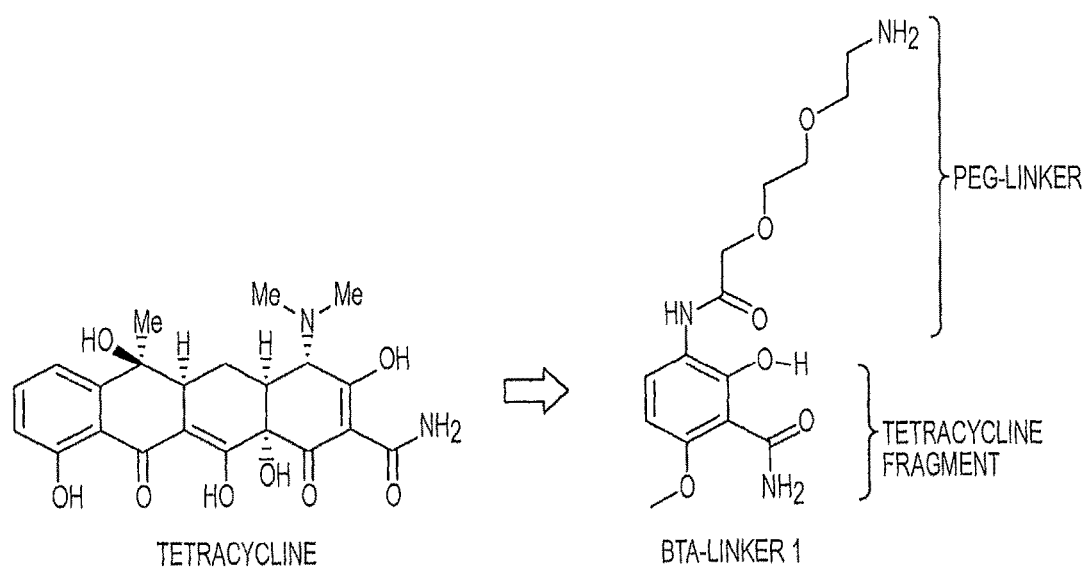
FIG. 2 shows the structure of tetracycline and the BTA linker 1 formed from a PEG (polyethylene glycol) linker and tetracycline fragment.

The compound Oxy133 (FIG. 1) can act as a potent osteogenic oxysterol, which induces osteogenic differentiation of osteoprogenitor cells in vitro and robust bone formation in vivo in rat and rabbit spine fusion models. An osteogenic oxysterol, Oxy149, is a combination of Oxy133 and a bone targeting agent (BTA) that is a derivative of tetracycline. As shown in FIG. 1, we have identified three sites for the attachment of BTA to Oxy133, i.e., at the hydroxyl groups of carbon 3, carbon 6, and carbon 20 through either succinic acid or aspartic acid linkers. Linker attachments of the tetracycline BTA fragments include, but are not limited to, succinate-based linkers and polyethylene glycol (PEG)-based linker units, such as those resulting in BTA-linker 1, depicted in FIG. 2. For example, an Oxy133-BTA analog can have BTA attached at the hydroxyl group of carbon 6. Also set forth herein are other analogues where BTA can be linked to carbon 3 or carbon 20, or to more than one carbon resulting in a total of 2 or 3 BTA units on Oxy133.

Bone specific drug delivery by bone specific drug delivery systems, for example, for orthopedic medicine, is not only applicable to drugs marginally acceptable for bone disease (e.g.: estradiol and diclofenac) to increase efficacy, minimize side effects and allow for appropriate dosing. This concept can be extended to osteogenic molecules not previously tested for systemic bone disease, potentially making them into effective treatments for osteoporosis. Oxysterol-based agonists of Hedgehog (Hh) signaling with osteogenic properties mostly fall into this category. Among known chemical entities with high bone affinity ranging from oligopeptides to various bisphosphonates, the antibiotic tetracycline is a relatively nontoxic, orally available and "human-experienced" bone targeting agent or moiety. However, its powerful antibiotic activity, chemical complexity, and lack of stability limit the clinical potential of unmodified tetracycline as a bone targeting agent (BTA). Therefore, tetracycline fragments are considered as BTA-units. The latter are devoid of antimicrobial activity and undue chemical complexity, while retaining most (80%) of the bone affinity compared to tetracycline in a hydroxyapatite binding assay. The linker attachments of tetracycline BTA fragments can include succinate-based linkers and polyethylene glycol (PEG)-based linker units, for example, for BTA-linker 1, depicted in FIG. 2. BTA agents can be attached to drug molecules via hydrolysable linker bonds. Non-hydrolysable bonds may be used in cases where the drug molecule after conjugation to the BTA unit retains pharmacological activity. Ester groups can be used, as they populate a favorable stability range relative to more labile thioesters and more stable amides (L. Gil et al., *Bioorg. Med. Chem.* 1999, 7, 901-919). The in vivo stability of ester groups can be further fine-tuned by substitutions placed adjacent to the ester group (T. C. Bruice et al., *Bioorganic Mechanisms*, Vol. 1, W. A. Benjamin, New York, 1966, 1-258). Hence, Oxy133-BTA ester conjugates can be suitable for systemic dosing (oral, ip, or iv) that entails selective deposition in bone tissue followed by enzymatic linker hydrolysis and release of the osteogenic agent, Oxy133, at controlled rates into the target tissue. Such attachment of BTA-linker 1 to the 6-position of Oxy133 to form the conjugate Oxy149 (3a) can be achieved by a straightforward coupling to succinic anhydride via ester linkage, as depicted below.

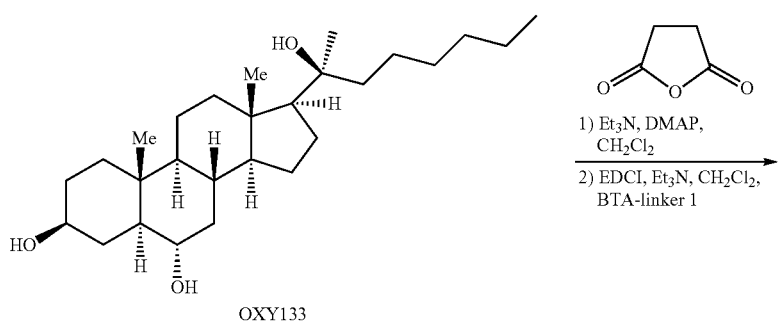

OXY133

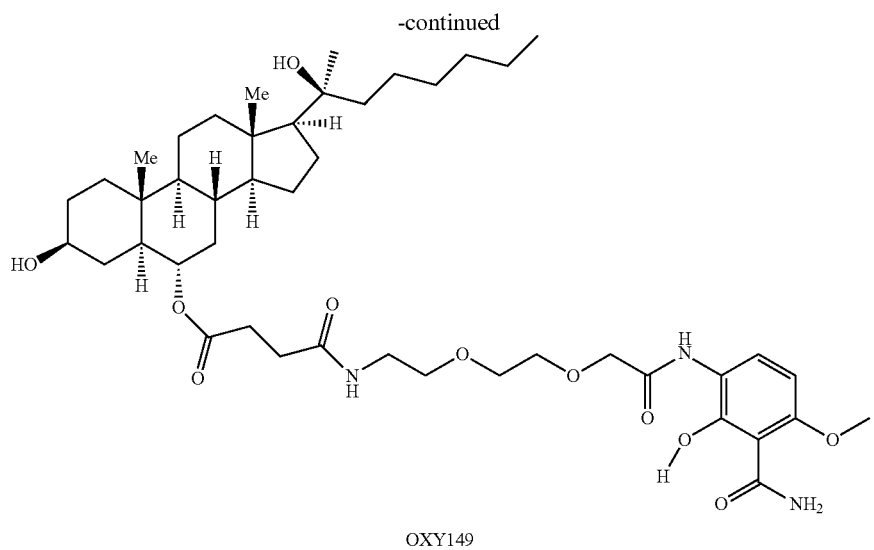

OXY149

(In Oxy133 the 6-hydroxyl group is more reactive toward succinic anhydride than the 3-hydroxyl.) The resulting conjugate, OXY149, retains most of the osteogenic activity of the parent Oxy133 in C3H10T1/2 cells determined by the level of induction of osteogenic differentiation marker, alkaline phosphatase activity after 4 days of treatment (Control: 2±1; Oxy133 (1 μM): 390±10; Oxy149 (1 μM): 100±12; Oxy149 (5 μM): 500±18; Oxy149 (10 μM); 480±12; Oxy149 (20 μM): 470±25). BTA-linker 1 can be attached via the 3- and/or 6-positions of OXY133 using tunable linker attachments.

Analogues 2, 3, and 4, in which Oxy133 is conjugated to the BTA via the 3- and/or 6-positions with ester linker units derived from succinic (a series) or aspartic acid (b series) and a carbamate linker unit (c series), that is, oxysterol-BTA conjugates with a tunable linker attachment, are depicted below.

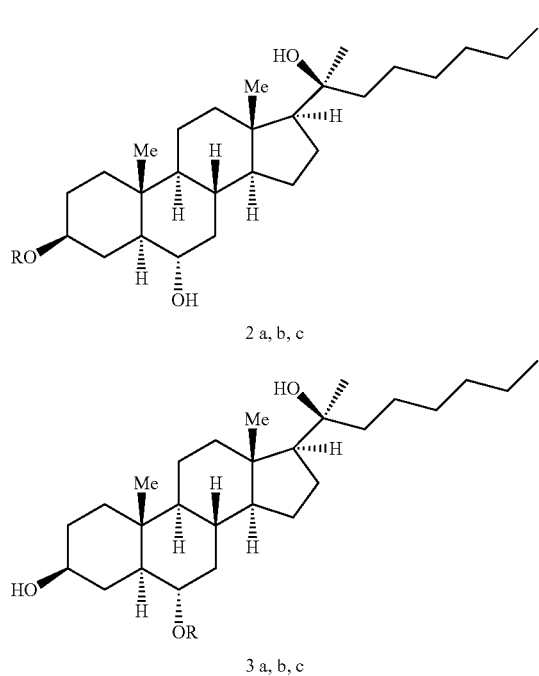

2 a, b, c 3 a, b, c

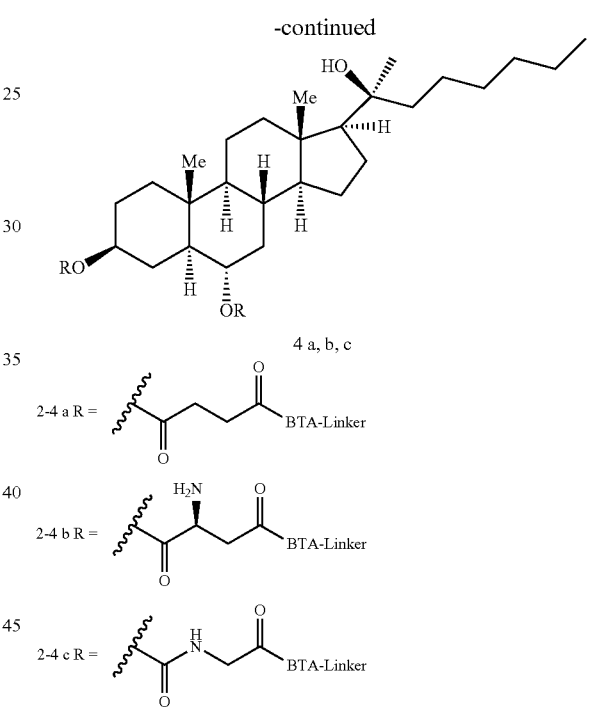

4 a, b, c 2-4 a R =
2-4 b R =
2-4 c R =

Figure 3:
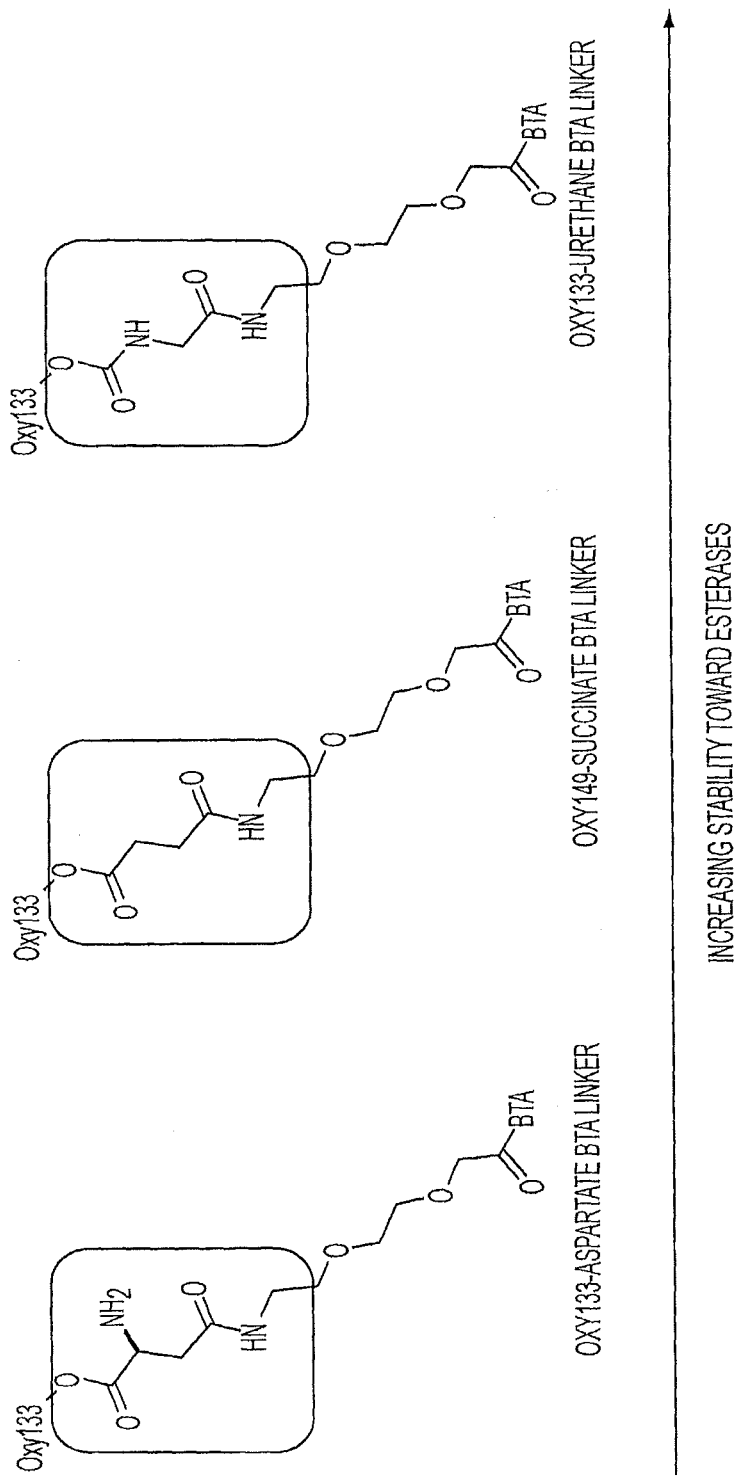
FIG. 3 illustrates the relative susceptibility of various linker units to cleavage by esterases.

The carbamate linker should be more stable toward esterase hydrolysis compared to ester linkers. The succinic acid-based linker should be more stable toward esterase hydrolysis compared to the aspartic acid-based linker, which may undergo enzymatic hydrolysis of the amino ester bond more readily. A difference in the rate of ester hydrolysis can be used to fine tune the release of Oxy133 in the target bone tissue. For example, Oxy 133 conjugated to ETA using a urethane unit should be more stable than when the conjugate is formed using an aspartate. This relative susceptibility of various linker units to cleavage by esterases is illustrated in FIG. 3.

The synthesis of the Oxy133-BTA conjugated analogues 2, 3, and 4 starting from pregnenolone (5) is shown below. The latter can be transformed by known methods to differentially protected Oxy133 derivatives, 6 a-c, by protection of the 3-hydroxyl, addition of the side chain, hydroboration-oxidation of the 5-alkene, and then, depending on the analogue desired, selective protection or deprotection of the hydroxyl groups. The coupling partners for these compounds can be prepared.

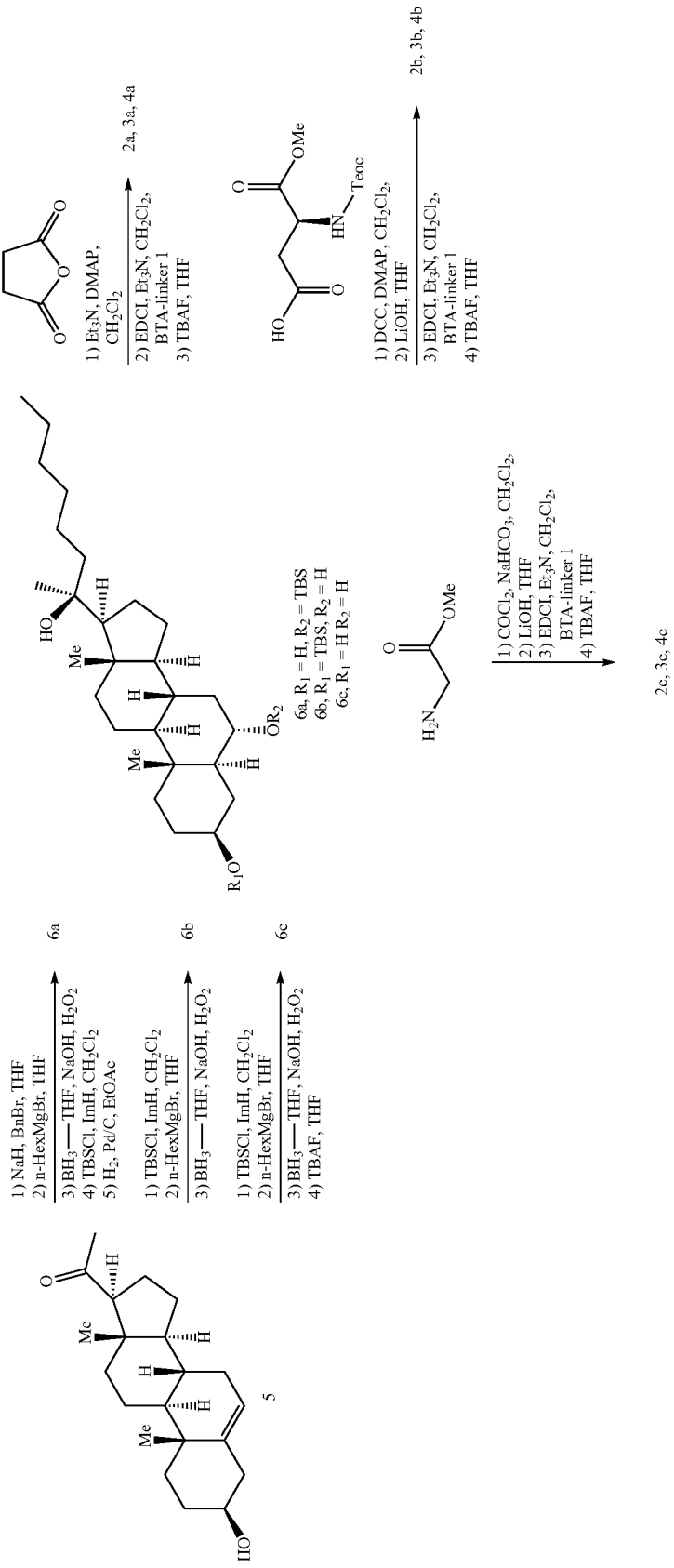

Figure 6:
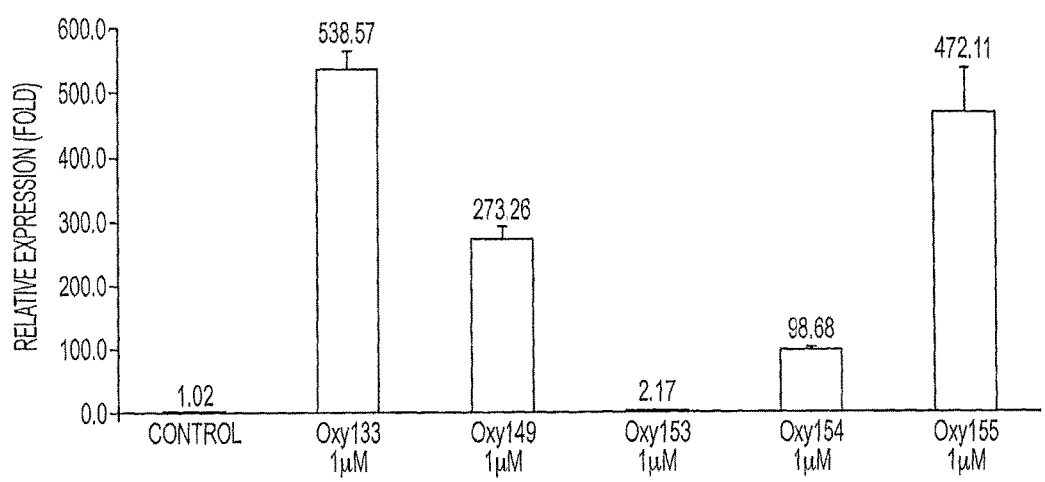
FIG. 6 shows the expression of bone sialoprotein (BSP) gene of M2-10B4 cells in vitro 4 days after initial contact with oxysterols.

First, differentially protected Oxy133 derivatives 6 a-c are acylated at the 3 and/or 6-hydroxyl with succinic anhydride or protected aspartic acid and the resulting carboxylic acids are then coupled to BTA-linker 1 to afford ester conjugates, 5 as depicted in FIG. 6. After the ester coupling reactions, the tert-butyldimethylsilyl ethers (TBS) and, in the case of 2-4b, the 2-trimethylsilylethyl carbamate (Teoc) unit can be cleaved with tetra-n-butylammonium fluoride (TBAF) to afford the final products incorporating the succinic acid linker (2-4a) and the aspartic acid linker (2-4b). Compound 3a corresponds to Oxy149, obtained in the preliminary study shown in FIG. 3. The carbamate linked analogues, 2-4c, are prepared by converting glycine methylester into the isocyanate to carbamylate Oxy133 derivatives 6a-c after which the synthesis proceeds in an analogous fashion.

A derivative of Oxy133-BTA may 1) have greater osteogenic activity in a C3H10T1/2 cell based assay screens than Oxy149, perhaps based on a more favorable cell-cleavable property, and 2) show optimized hydroxyapatite binding capacity.

Using exhaustive acylation conditions, the tertiary alcohol at C-20 can be acylated, to afford peracylated oxysterol-BTA conjugate analogs as depicted below.

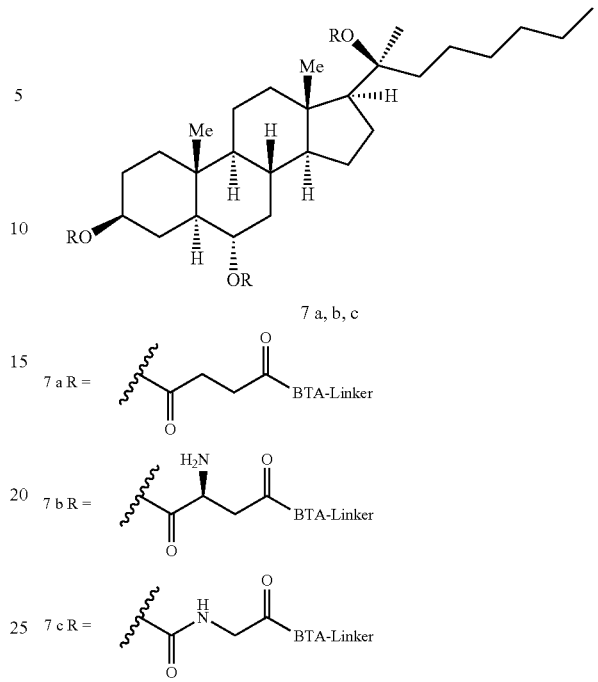

Synthetic routes to obtain compounds 3b (Oxy 154), 4a (Oxy 153), and 4b (Oxy 155) (shown in FIG. 4), starting from the Oxy 133 compound, are shown below.

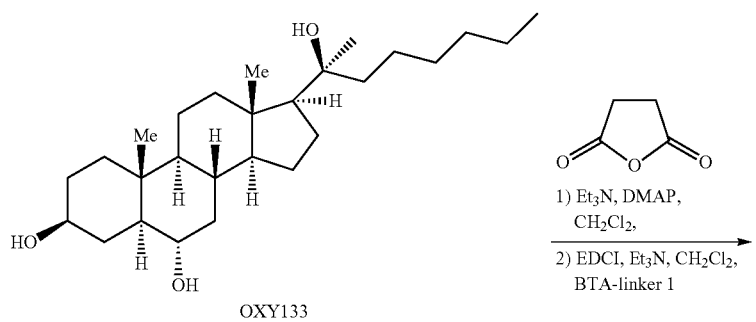

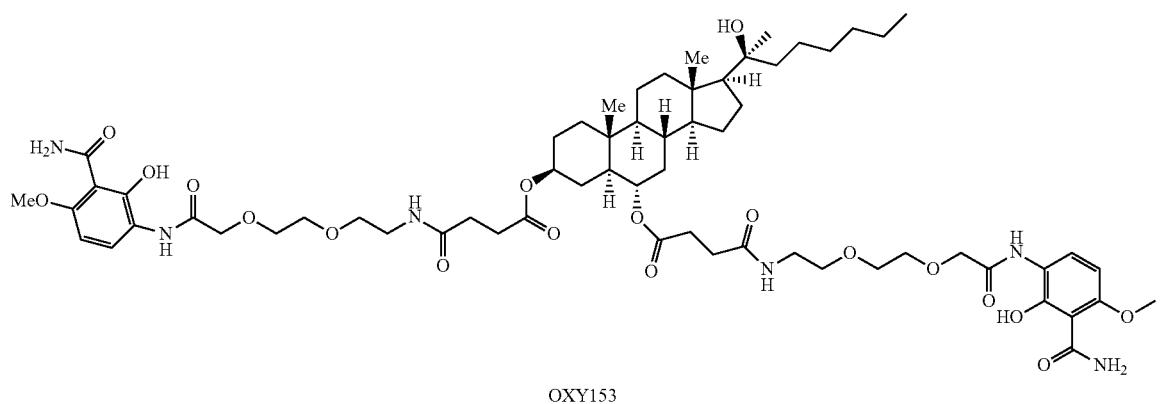

-continued
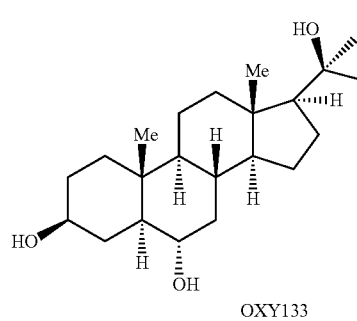 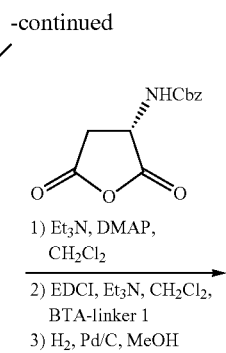
OXY133
1) Et₃N, DMAP, CH₂Cl₂
2) EDCI, Et₃N, CH₂Cl₂, BTA-linker 1
3) H₂, Pd/C, MeOH
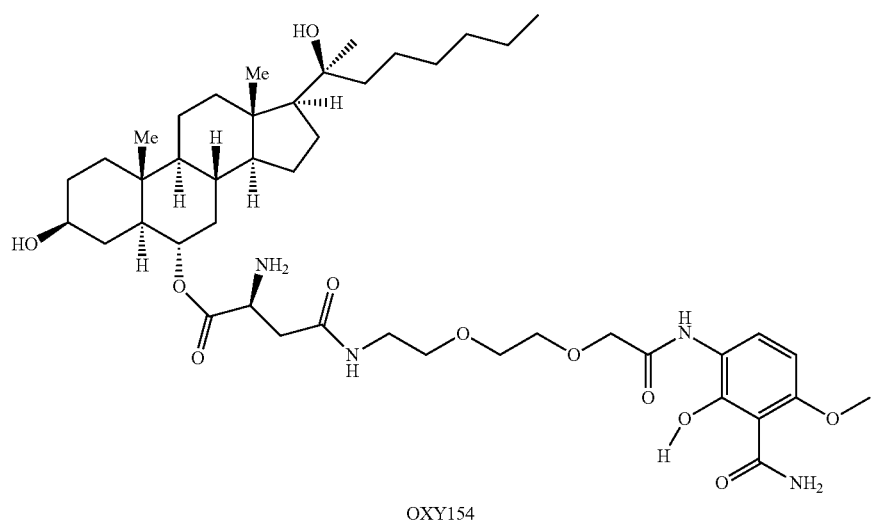
OXY154
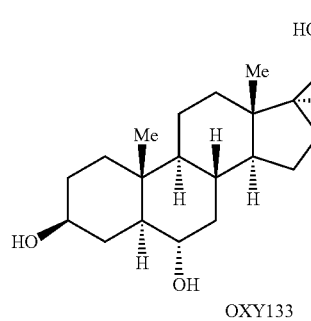 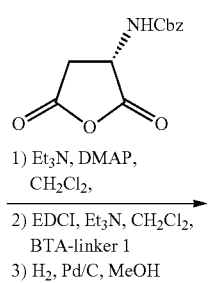
OXY133
1) Et₃N, DMAP, CH₂Cl₂,
2) EDCI, Et₃N, CH₂Cl₂, BTA-linker 1
3) H₂, Pd/C, MeOH
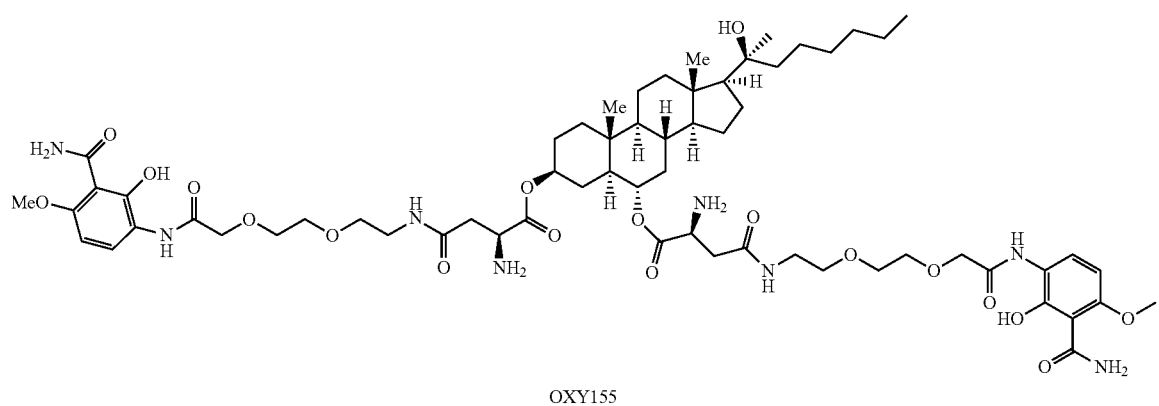
OXY155

A summary of several molecules of which the synthesis is described above is provided below.
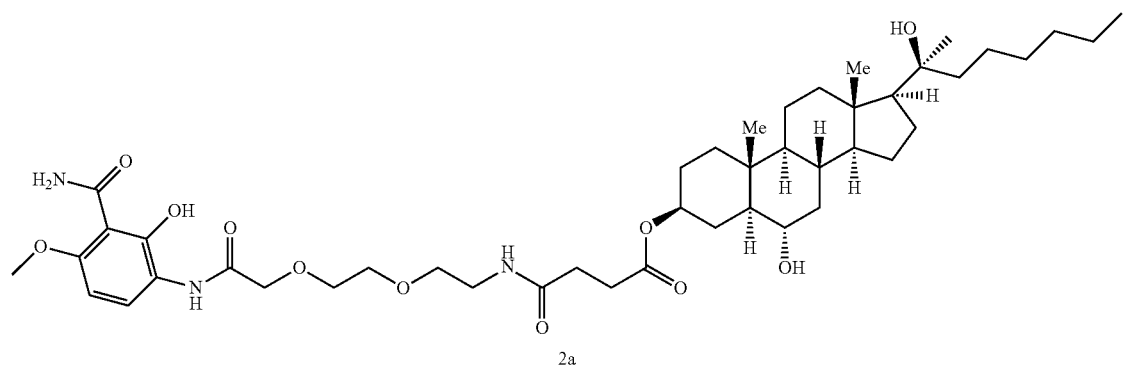
2a
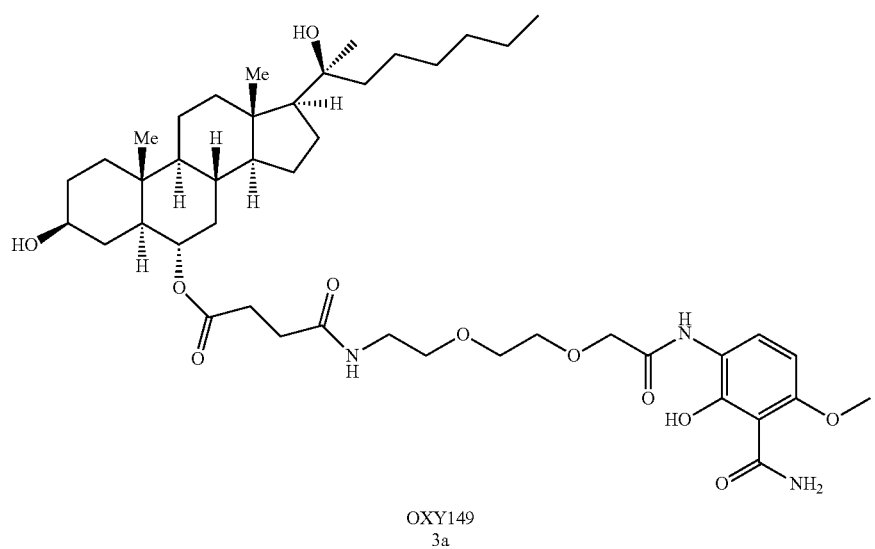
OXY149
3a
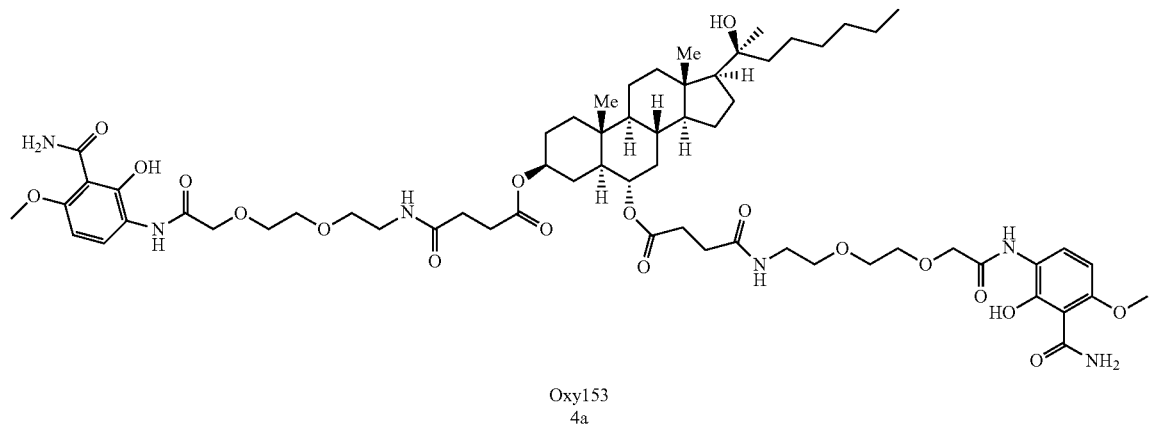
Oxy153
4a

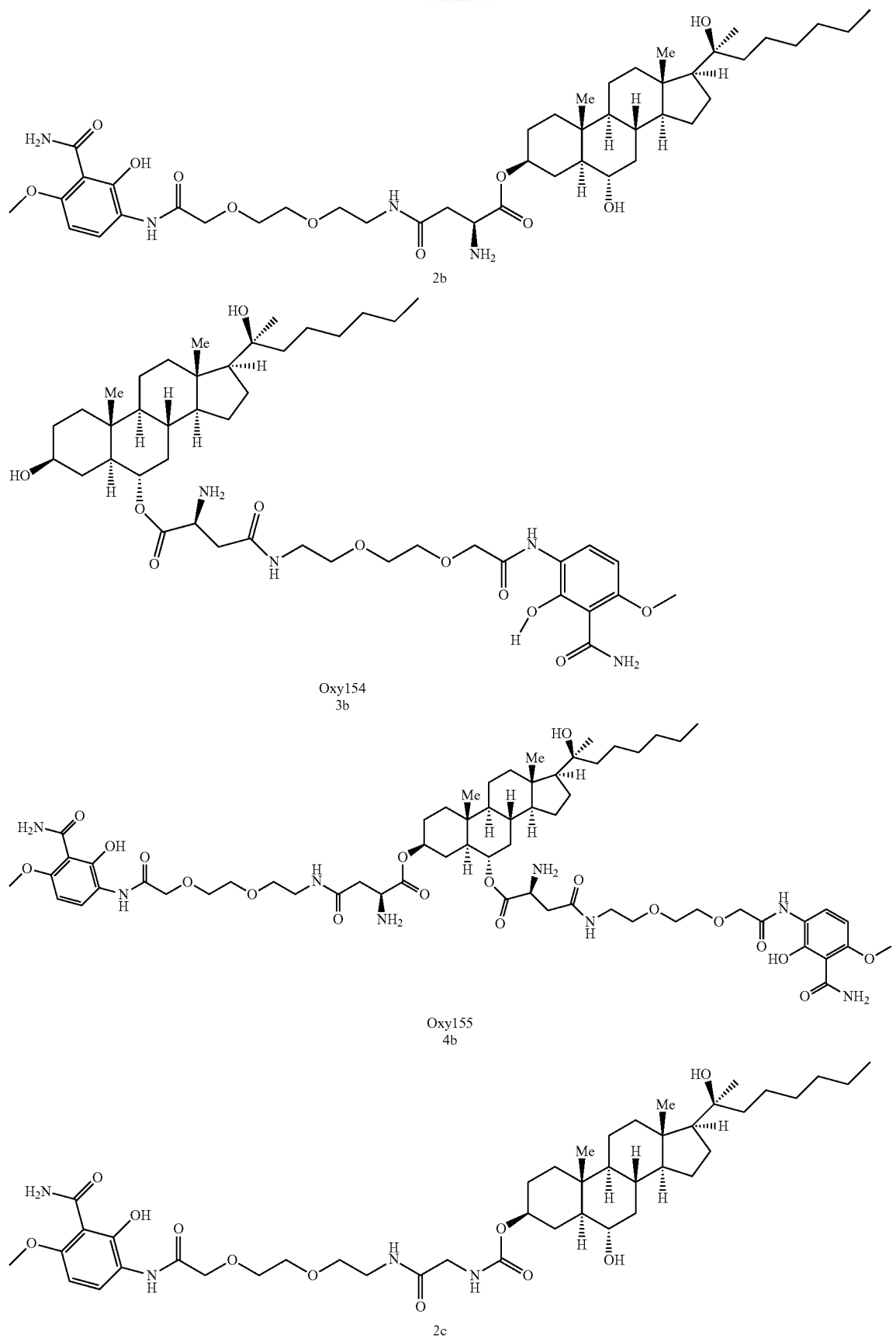

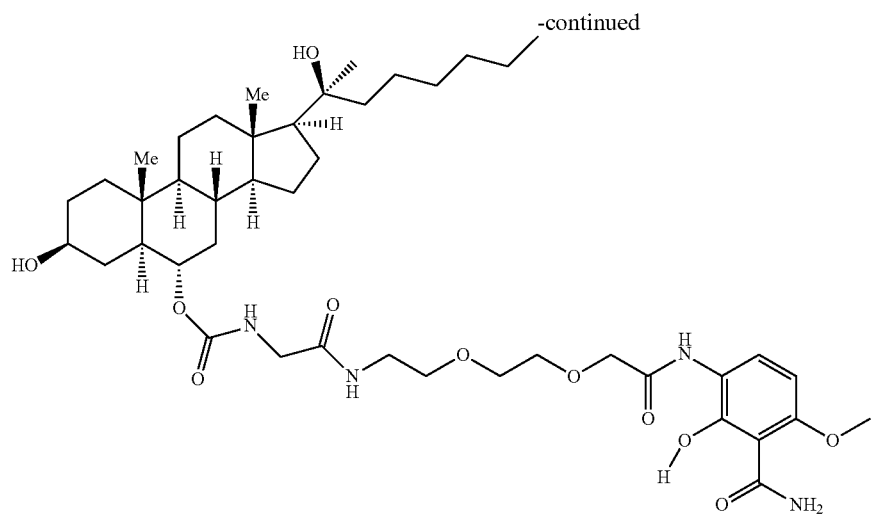
3c
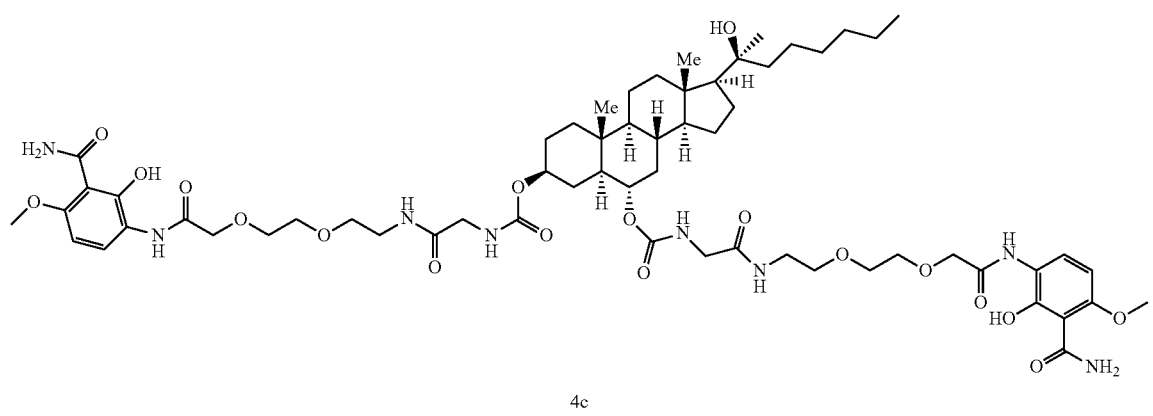
4c
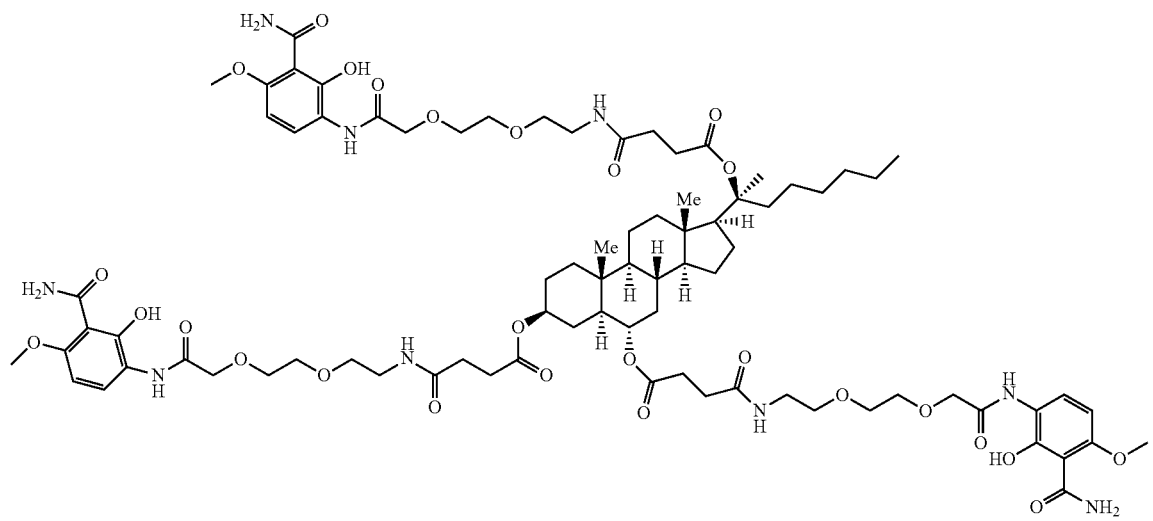
7a

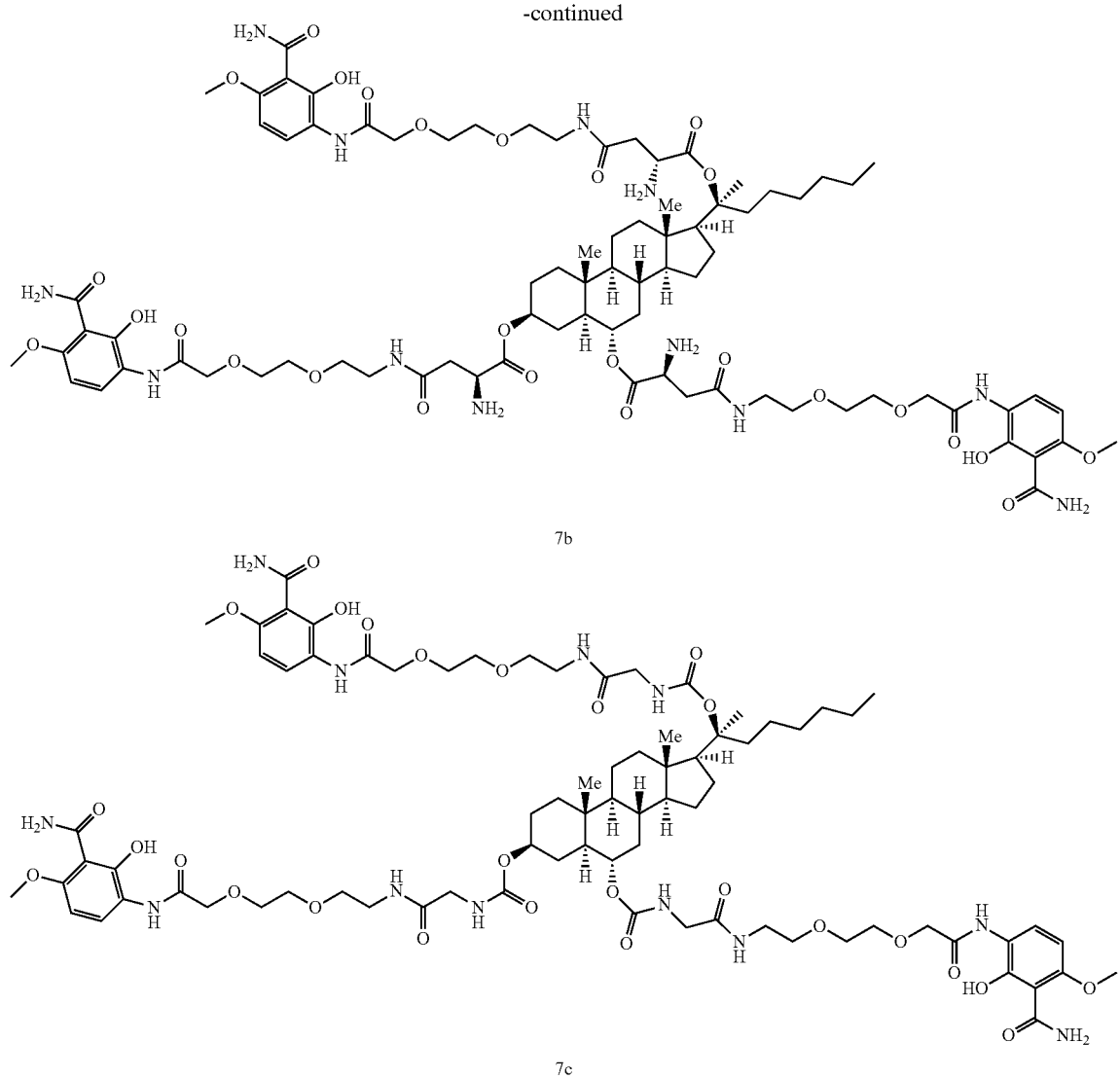

7b

7c

An embodiment of the invention relates to hybrid molecules comprising Oxy133 or other osteogenic oxysterols described previously by the some of the present inventors, wherein the oxysterols are linked to other versions of tetracycline-derived bone targeting moieties described by some of the present inventors. Some such moieties are described, e.g., in U.S. Pat. No. 7,196,220 and U.S. Pat. No. 7,196,220.

An osteogenic oxysterol molecule can be linked (conjugated) to such a tetracycline derivative and used as described herein. Representative such oxysterols include Oxy8, Oxy34, Oxy40, and Oxy49, or other suitable oxysterols previously described by the present inventors or by others. Some such hybrid molecules include the following.

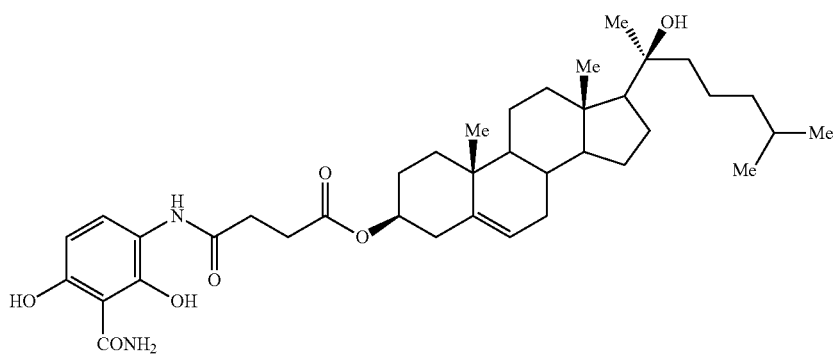

1 (Oxy8-3-Tet)

33 34
-continued
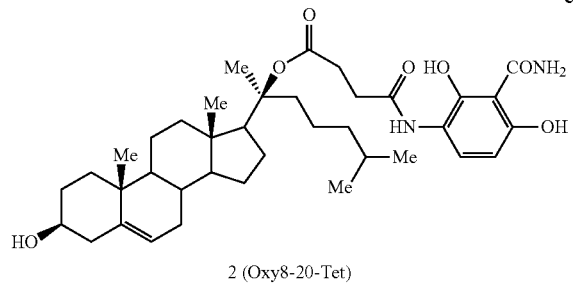
2 (Oxy8-20-Tet)
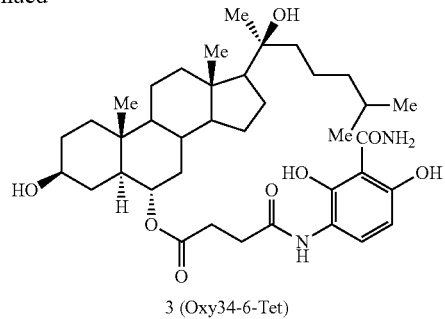
3 (Oxy34-6-Tet)
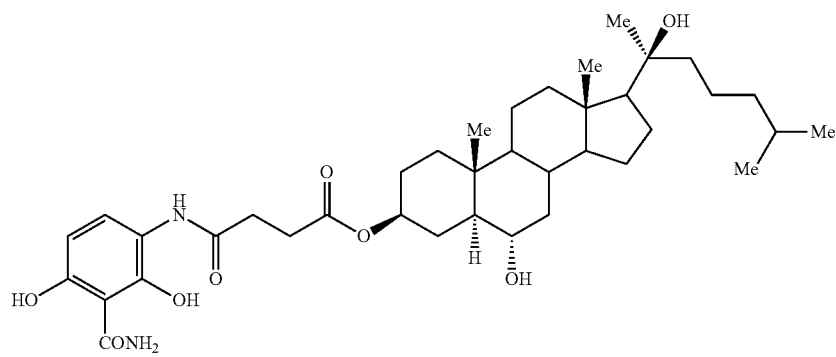
4 (Oxy34-3-Tet)
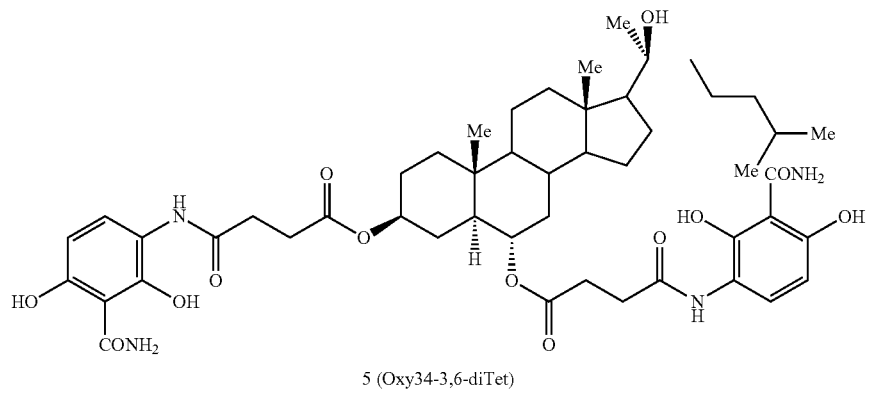
5 (Oxy34-3,6-diTet)
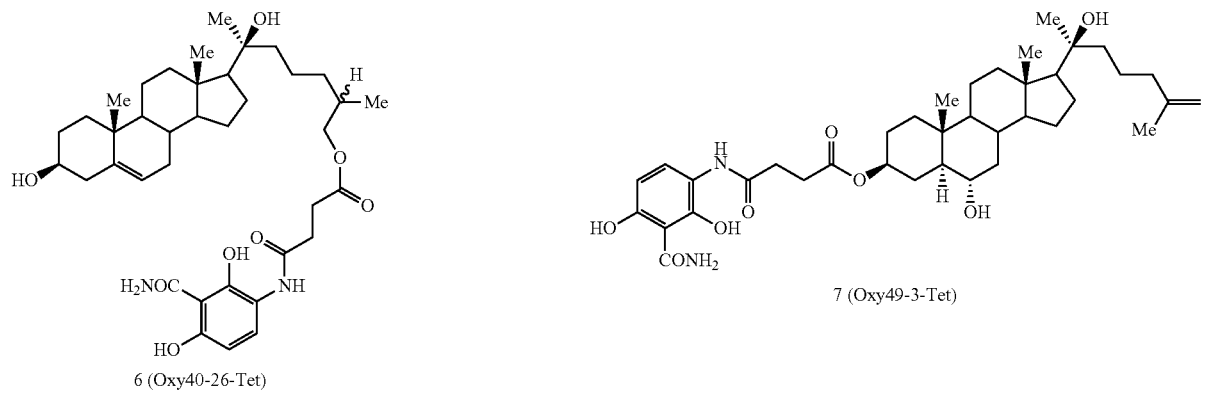
6 (Oxy40-26-Tet)
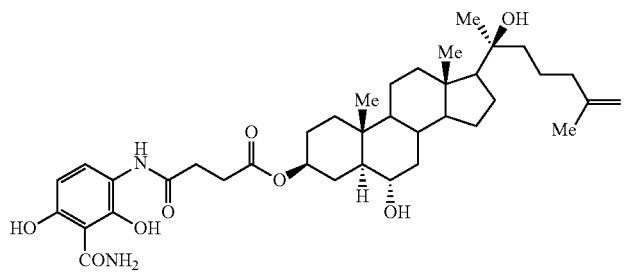
7 (Oxy49-3-Tet)

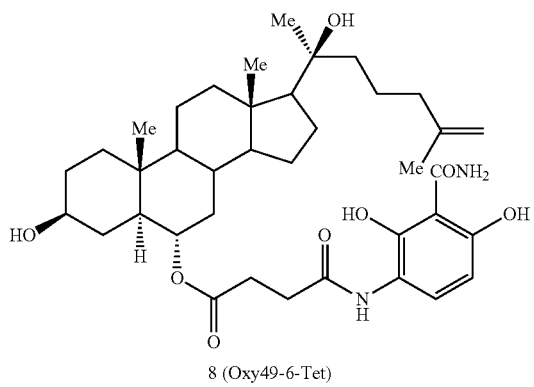

8 (Oxy49-6-Tet)

These oxysterols and oxysterol-bone targeting agent (BTA) conjugates can be a part of a pharmaceutical composition that can be used as a therapeutic agent for the treatment of osteoporosis.

Oxysterols form a family of oxygenated derivatives of cholesterol that are present in the circulation, and in human and animal tissues. Oxysterols have been found to be present in atherosclerotic lesions and play a role in various physiologic processes, such as cellular differentiation, inflammation, apoptosis, and steroid production. Some naturally occurring oxysterols can have osteogenic properties (Kha). A naturally occurring oxysterol, 20(S)-hydroxycholesterol ("20S") (W.-K. Kim, *J. Bone Miner. Res.* 2007, 22, 1711-9), is both osteogenic and anti-adipogenic when applied to multipotent mesenchymal cells capable of differentiating into osteoblasts and adipocytes. Structural modifications of 20S can be made to synthesize more potent analogues of 20S including Oxy34 and Oxy49, which can induce the osteogenic and inhibit the adipogenic differentiation of bone marrow stromal cells (MSC) through activation of Hedgehog (Hh) signaling (J. S. Johnson). Oxy34 and Oxy49 can stimulate spine fusion in vivo in a rat model of posterolateral spine fusion (J. S. Johnson). Oxysterols can make more feasible clinical options for physicians treating, for example, long bone fractures, spine disorders, and osteoporosis.

The compounds of embodiments of the present invention are useful as pharmaceutical compositions prepared with a therapeutically effective amount of a compound of the invention, as defined herein, and a pharmaceutically acceptable carrier or diluent.

The compounds of the invention can be formulated as pharmaceutical compositions and administered to a subject in need of treatment, for example a mammal, such as a human patient, in a variety of forms adapted to the chosen route of administration, for example, orally, nasally, intraperitoneally, or parenterally, by intravenous, intramuscular, topical or subcutaneous routes, or by injection into tissue.

Thus, compounds of the invention may be systemically administered, e.g., orally, in combination with a pharmaceutically acceptable vehicle such as an inert diluent or an assimilable edible carrier, or by inhalation or insufflation. They may be enclosed in hard or soft shell gelatin capsules, may be compressed into tablets, or may be incorporated directly with the food of the patient's diet. For oral therapeutic administration, the compounds may be combined with one or more excipients and used in the form of ingestible tablets, buccal tablets, troches, capsules, elixirs, suspensions, syrups, wafers, and the like. The compounds may be combined with an inert powdered carrier and inhaled by the subject or insufflated. Such compositions and preparations should contain at least 0.1% of a compound of an embodiment of the present invention. The percentage of the compositions and preparations may, of course, be varied and may conveniently be between about 2% to about 60% of the weight of a given unit dosage form. The amount of compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the compounds may be incorporated into sustained-release preparations and devices. For example, the compounds may be incorporated into time release capsules, time release tablets, time release pills, and time release polymers or nanoparticles.

The compounds may also be administered intravenously or intraperitoneally or subcutaneously by infusion or injection. Solutions of the compounds can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the compounds which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the compounds in the required amount in the appropriate solvent with various of the other ingredients enumerated above, as required, followed by filter sterilization. In the case of sterile powders for the preparation of sterile injectable solutions, the preferred methods of preparation are vacuum drying and freeze drying techniques, which yield a powder of the active ingredient plus any additional desired ingredient present in the previously sterile-filtered solutions.

For topical administration, the compounds may be applied in pure form. However, it may be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Other solid carriers include nontoxic polymeric nanoparticles or microparticles. Useful liquid carriers include water, alcohols or glycols or water/alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508), all of which are hereby incorporated by reference.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949, which is hereby incorporated by reference.

For example, the concentration of the compounds in a liquid composition, such as a lotion, can be from about 0.1-25% by weight, or from about 0.5-10% by weight. The concentration in a semi-solid or solid composition such as a gel or a powder can be about 0.1-5% by weight, or about 0.5-2.5% by weight.

The amount of the compounds required for use in treatment will vary not only with the particular salt selected but also with the route of administration, the nature of the condition being treated and the age and condition of the patient and will be ultimately at the discretion of the attendant physician or clinician.

Effective dosages and routes of administration of agents of the invention are conventional. The exact amount (effective dose) of the agent will vary from subject to subject, depending on, for example, the species, age, weight and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g., The Pharmacological Basis of Therapeutics, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. A therapeutic dose can also be selected by analogy to dosages for comparable therapeutic agents.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose will be in the range of from about 0.001 to about 100 mg/kg, e.g., from about 0.01 to about 100 mg/kg of body weight per day, such as above about 0.1 mg per kilogram, or in a range of from about 1 to about 10 mg per kilogram body weight of the recipient per day. For example, a suitable dose may be about 1 mg/kg, 10 mg/kg, or 50 mg/kg of body weight per day.

The compounds are conveniently administered in unit dosage form; for example, containing 0.05 to 10000 mg, 0.5 to 10000 mg, 5 to 1000 mg, or about 100 mg of active ingredient per unit dosage form.

The compounds can be administered to achieve peak plasma concentrations of, for example, from about 0.5 to about 75 µM, from about 1 to 50 µM, from about 2 to about 30 µM, or from about 5 to about 25 µM. Exemplary desirable plasma concentrations include at least or no more than 0.25, 0.5, 1, 5, 10, 25, 50, 75, 100, or 200 µM. For example, plasma levels may be from about 1 to 100 micromolar or from about 10 to about 25 micromolar. This may be achieved, for example, by the intravenous injection of a 0.05 to 5% solution of the compounds, optionally in saline, or orally administered as a bolus containing about 1-100 mg of the compounds. Desirable blood levels may be maintained by continuous infusion to provide about 0.00005-5 mg per kg body weight per hour, for example at least or no more than 0.00005, 0.0005, 0.005, 0.05, 0.5, or 5 mg/kg/hr. Alternatively, such levels can be obtained by intermittent infusions containing about 0.0002-20 mg per kg body weight, for example, at least or no more than 0.0002, 0.002, 0.02, 0.2, 2, 20, or 50 mg of the compounds per kg of body weight.

The compounds may conveniently be presented in a single dose or as divided doses administered at appropriate intervals, for example, as one dose per day or as two, three, four or more sub-doses per day. The sub-dose itself may be further divided, e.g., into a number of discrete loosely spaced administrations; such as multiple inhalations from an insufflator.

An aspect of the invention is a bioactive or pharmaceutical composition comprising a compound set forth herein or a pharmaceutically acceptable salt or solvate thereof and a pharmaceutically acceptable carrier. The terms "bioactive" composition or "pharmaceutical" composition are used interchangeably herein. Both terms refer to compositions that can be administered to a subject, used to coat or be present in a medical device that is introduced into a subject, or the like. These bioactive or pharmaceutical compositions are sometimes referred to herein as "pharmaceutical compositions or bioactive compositions of the invention." Sometimes the phrase "administration of a compound" is used herein in the context of administration of this compound to a subject (e.g., contacting the subject with the compound). It is to be understood that the compound for such a use can generally be in the form of a pharmaceutical composition or bioactive composition comprising the compound.

Another aspect of the invention is a method for inducing (stimulating, enhancing) a Hedgehog (Hh) pathway mediated response, in a cell or tissue, e.g., in a subject, comprising contacting the cell or tissue with an effective amount (e.g., a therapeutically effective amount) of a compound, wherein the Hedgehog (Hh) pathway mediated response is the stimulation of osteoblastic differentiation, osteomorphogenesis, and/or osteoproliferation. The Hh mediated response can be useful in regenerative medicine.

Another aspect of the invention is a method for treating a subject having a bone disorder, osteopenia, osteoporosis, or a bone fracture, comprising administering to the subject an effective amount of a bioactive composition or pharmaceutical composition comprising a compound. The subject can be administered the bioactive composition or pharmaceutical composition at a therapeutically effective dose in an effective dosage form at a selected interval to, e.g., increase bone mass, ameliorate symptoms of osteoporosis, or reduce, eliminate, prevent or treat other conditions which would benefit from an increase in osteomorphogenesis and/or osteoproliferation. The subject can be administered the bioactive composition or pharmaceutical composition at a therapeutically effective dose in an effective dosage form at a selected interval to ameliorate the symptoms of osteoporosis. In one embodiment, the subject is treated to induce bone formation by harvesting mammalian mesenchymal stem cells (e.g., from the subject or from a suitable mammal, or from a tissue or cell bank), treating the mammalian mesenchymal cells with a compound to induce osteoblastic differentiation of the cells, and administering the differentiated cells to the subject.

In any of the methods of the invention, the compound can be administered to a cell, tissue or organ by local administration. For example, the compound can be applied locally with a cream or the like, or it can be injected or otherwise introduced directly into a cell, tissue or organ, or it can be introduced with a suitable medical device (e.g., an implant). Alternatively, the compound can be administered systemically, e.g., orally, intravenously (though IV), or via injection such as intraperitoneal (ip) injection or subcutaneous (subcu) injection.

Another aspect of the invention is a kit for carrying out one or more of the methods described herein. The kit can comprise an effective amount (e.g., a therapeutically effective amount) of a compound, optionally in a container.

Another aspect of the invention is an implant for use in the body of a subject (e.g., an animal such as a human) comprising a substrate having a surface. The surface or insides of the implant comprises a bioactive composition or pharmaceutical composition comprising the compound in an amount sufficient to induce bone formation in the surrounding bone tissue.

Optionally, a bioactive composition, method, kit or medical device of the invention can comprise one or more other suitable therapeutic agents, such as, e.g., parathyroid hormone, sodium fluoride, insulin-like growth factor I (ILGF-I), insulin-like growth factor II (ILGF-II), transforming growth factor beta (TGF-β), a cytochrome P450 inhibitor, an osteogenic prostanoid, BMP 2, BMP 4, BMP 7, BMP 14, and/or an anti-resorptive agent such as, e.g., bisphosphonate.

In addition to the compounds set forth herein, other embodiments of the invention encompass any and all individual stereoisomers at any of the stereocenters shown in the Formulas, including diastereomers, racemates, enantiomers, and other isomers of the compounds. In embodiments of the invention, all polymorphs and solvates of the compound, such as hydrates and those formed with organic solvents, are included. A "solvate" is a complex or aggregate formed by one or more molecules of a solute, e.g., a compound or a pharmaceutically-acceptable salt thereof, and one or more molecules of a solvent. Such solvates can be crystalline solids having a substantially fixed molar ratio of solute and solvent. Suitable solvents will be known by those of ordinary skill in the art, e.g., water, ethanol or dimethylsulfoxide. Such isomers, polymorphs, and solvates may be prepared by methods known in the art, such as by regiospecific and/or enantioselective synthesis and resolution.

The ability to prepare salts depends on the acidity or basicity of a compound. Suitable salts of the compound include, but are not limited to, acid addition salts, such as those made with hydrochloric, hydrobromic, hydroiodic, perchloric, sulfuric, nitric, phosphoric, acetic, propionic, glycolic, lactic pyruvic, malonic, succinic, maleic, fumaric, malic, tartaric, citric, benzoic, carbonic cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid; salts made with saccharin; alkali metal salts, such as sodium and potassium salts; alkaline earth metal salts, such as calcium and magnesium salts; and salts formed with organic or inorganic ligands, such as quaternary ammonium salts.

Additional suitable salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mutate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide, and valerate salts of the compounds.

It is to be understood that references to compounds herein include pharmaceutically acceptable salts or solvates thereof.

In any of the methods, compositions or kits of the invention, particularly for use in treating a subject, a composition of the invention may optionally be in combination with one or more other suitable therapeutic agents. Any therapeutic agent that is suitable for treatment of a particular condition can be used. Suitable such agents or drugs will be evident to one skilled in the art. For example, for the treatment of bone disorders, a conventional therapeutic drug can be used in combination with a composition of the invention. Some such agents include, e.g., parathyroid hormone, sodium fluoride, insulin-like growth factor I (ILGF-I), insulin-like growth factor II (ILGF-II), transforming growth factor beta (TGF-$\beta$), a cytochrome P450 inhibitor, an osteogenic prostanoid, BMP 2, BMP 4, BMP 7, BMP 14, and/or bisphosphonates or other inhibitors of bone resorption.

A composition or compound of the invention can be formulated as a pharmaceutical composition, which comprises a composition of the invention and pharmaceutically acceptable carrier. By a "pharmaceutically acceptable carrier" is meant a material that is not biologically or otherwise undesirable, i.e., the material may be administered to a subject without causing any undesirable biological effects or interacting in a deleterious manner with any of the other components of the pharmaceutical composition in which it is contained. The carrier is naturally selected to minimize any degradation of the active ingredient and to minimize any adverse side effects in the subject, as would be well known to one of skill in the art. For a discussion of pharmaceutically acceptable carriers and other components of pharmaceutical compositions, see, e.g., Remington's Pharmaceutical Sciences, 18$^{th}$ ed., Mack Publishing Company, 1990. Some suitable pharmaceutical carriers will be evident to a skilled worker and include, e.g., water (including sterile and/or deionized water), suitable buffers (such as PBS), physiological saline, cell culture medium (such as DMEM), artificial cerebral spinal fluid, dimethylsulfoxide (DMSO), or the like.

One of skill in the art will appreciate that a particular formulation of the invention will depend, at least in part, upon the particular agent or combination of agents that is employed and the chosen route of administration. Accordingly, there is a wide variation of suitable formulations of compositions of the present invention. Some representative formulations are discussed below. Others will be evident to a skilled worker. A compound can be administered locally or directly to a cell, tissue or organ in need of treatment, or it can be administered systemically.

Formulations or compositions suitable for oral administration can consist of liquid solutions, such as an effective amount of compound dissolved in diluents, such as water, saline, or fruit juice; capsules, sachets or tablets, each containing a predetermined amount of the active ingredient, as solid, granules or freeze-dried cells; solutions or suspensions in an aqueous liquid; and oil-in-water emulsions or water-in-oil emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Suitable formulations for oral delivery can also be incorporated into synthetic and natural polymeric microspheres, or other means to protect the agents of the present invention from degradation within the gastrointestinal tract.

Formulations suitable for parenteral administration (e.g., intravenous) include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (i.e., lyophilized) condition requiring only the addition of the sterile liquid carrier, for example, water, for injections, immediately prior to use. Extemporaneous injection solutions and suspensions can be prepared from sterile powders, granules, and tablets of the kind previously described.

A compound, alone or in combination with other therapeutic agents, can be made into aerosol formulations to be administered via inhalation. These aerosol formulations can be placed into pressurized acceptable propellants, such as dichlorodifluoromethane, propane, nitrogen, and the like.

Suitable formulations for topical administration include lozenges comprising the active ingredient in a flavor, usually sucrose and acacia or tragacanth; pastilles comprising the active ingredient in an inert base, such as gelatin and glycerin, or sucrose and acacia; mouthwashes comprising the active ingredient in a suitable liquid carrier; or creams, emulsions, suspensions, solutions, gels, creams, pastes, foams, lubricants, sprays, suppositories, or the like.

Other suitable formulations include, e.g., hydrogels and polymers suitable for timed release of a compound, or nanoparticles for small dose delivery of a compound. Such formulations are well-known to those of skill in the art.

A person skilled in the art will appreciate that a suitable or appropriate formulation can be selected, adapted or developed based upon the particular application at hand. In addition, the pharmaceutical compositions of the present invention may be prepared for administration by a variety of different routes, whether systemic, local or both. Such examples include, but are not limited to, administrations performed intraarticularly, intracranially, intradermally, intrahepatically, intramuscularly, intraocularly, intraperitoneally, intrathecally, intravenously, subcutaneously, transdermally, or directly into a bone region atherosclerotic site, such as by direct injection, introduction with a catheter or other medical devise, topical application, direct application, and/or by implanting a device into in an artery or other appropriate tissue site.

A compound may be formulated to be contained within, or adapted to release by a surgical or medical device or implant. In certain aspects, an implant may be coated or otherwise treated with a compound. For example, hydrogels, or other polymers, such as biacompatible and/or biodegradable polymers, may be used to coat an implant with the compositions of the present invention (i.e., the composition may be adapted for use with a medical device by using a hydrogel or other polymer). Polymers and copolymers for coating medical devices with an agent are well-known in the art. Examples of medical devises and implants include, but are not limited to, sutures and prostheses such as prosthetic joints, and can be in the shape, e.g., of a pin, screw, plate or prosthetic joint.

An "effective amount" of a compound, as used herein, refers to an amount that can bring about at least a detectable effect. A "therapeutically effective amount," as used herein, refers to an amount that can bring about at least a detectable therapeutic response in a subject being treated (e.g., the amelioration of one or more symptoms) over a reasonable period of time.

In embodiments of the invention, a compound can stimulate or inhibit a therapeutic response, as measured by any of a variety of conventional assays, by about 1%, 5%, 10%, 20%, 30%, 40%, 50% 150%, 200%, or more of that in an untreated control sample. Intermediate values in these ranges are also included.

Dosages for a compound can be in unit dosage form, such as a tablet or capsule. The term "unit dosage form," as used herein, refers to physically discrete units suitable as unitary dosages for animal (e.g., human) subjects, each unit containing a predetermined quantity of an agent of the invention, alone or in combination with other therapeutic agents, calculated in an amount sufficient to produce the desired effect in association with a pharmaceutically acceptable diluent, carrier, or vehicle.

One skilled in the art can routinely determine the appropriate dose, schedule, and method of administration for the exact formulation of the composition being used, in order to achieve the desired effective amount or effective concentration of the agent in the individual patient. One skilled in the art also can readily determine and use an appropriate indicator of the "effective concentration" of the compounds by a direct or indirect analysis of appropriate patient samples (e.g., blood and/or tissues), in addition to analyzing the appropriate clinical symptoms of the disease, disorder, or condition.

The exact dose of a compound or composition thereof administered to an animal, such as a human, in the context of the present invention will vary from subject to subject, depending on the species, age, weight, and general condition of the subject, the severity or mechanism of any disorder being treated, the particular agent or vehicle used, its mode of administration, other medications the patient is taking, and other factors normally considered by an attending physician, when determining an individual regimen and dose level appropriate for a particular patient, and the like. The dose used to achieve a desired concentration in vivo will be determined by the potency of the form of the compound, the pharmacodynamics associated with the compound in the host, with or without additional agents, the severity of the disease state of infected individuals, as well as, in the case of systemic administration, the body weight and age of the individual. The size of the dose may also be determined by the existence of any adverse side effects that may accompany the particular agent, or composition thereof, employed. It is generally desirable, whenever possible, to keep adverse side effects to a minimum.

For example, a dose can be administered in the range of from about 5 ng (nanograms) to about 1000 mg (milligrams), or from about 100 ng to about 600 mg, or from about 1 mg to about 500 mg, or from about 20 mg to about 400 mg. For example, the dose can be selected to achieve a dose to body weight ratio of from about 0.0001 mg/kg to about 1500 mg/kg, or from about 1 mg/kg to about 1000 mg/kg, or from about 5 mg/kg to about 150 mg/kg, or from about 20 mg/kg to about 100 mg/kg. For example, a dosage unit can be in the range of from about 1 ng to about 5000 mg, or from about 5 ng to about 1000 mg, or from about 100 ng to about 600 mg, or from about 1 mg to about 500 mg, or from about 20 mg to about 400 mg, or from about 40 mg to about 200 mg of a compound or a composition comprising a compound. In one embodiment of the invention, amounts of a compound as above (e.g., a few grams) are administered locally, such as in a spine fusion procedure as part of a scaffold.

A dose can be administered once per day, twice per day, four times per day, or more than four times per day as required to elicit a desired therapeutic effect. For example, a dose administration regimen can be selected to achieve a blood serum concentration of a compound of the present invention in the range of from about 0.01 to about 1000 nM, or from about 0.1 to about 750 nM, or from about 1 to about 500 nM, or from about 20 to about 500 nM, or from about 100 to about 500 nM, or from about 200 to about 400 nM. For example, a dose administration regime can be selected to achieve an average blood serum concentration with a half maximum dose of a compound of the present invention in the range of from about 1 µg/L (microgram per liter) to about 2000 µg/L, or from about 2 µg/L to about 1000 µg/L, or from about 5 µg/L to about 500 µg/L, or from about 10 µg/L to about 400 µg/L, or from about 20 µg/L to about 200 µg/L, or from about 40 µg/L to about 100 µg/L.

Certain embodiments of the invention may also include treatment with an additional agent which acts independently or synergistically with a compound to improve the therapeutic results. When given in combined therapy, the agent other than the compound can be given at the same time as the compound, or the dosing can be staggered as desired. The two (or more) drugs also can be combined in a composition. Doses of each can be less when used in combination than when either is used alone. Suitable doses can be determined by a skilled worker, using standard dosage parameters.

As used herein, the singular forms "a," "an" and "the" include plural referents unless the context clearly dictates otherwise.

A "subject," as used herein, includes any animal that exhibits a symptom of a condition that can be treated with a compound. Suitable subjects (patients) include laboratory animals (such as mouse, rat, rabbit, or guinea pig), farm animals, and domestic animals or pets (such as a cat, dog, or horse). Non-human primates and humans, including human patients, are included. Typical subjects include animals that exhibit aberrant amounts (lower amounts than a "normal" or "healthy" subject) of one or more physiological activities that are stimulated by Hedgehog signaling. The aberrant activities may be regulated by any of a variety of mechanisms, including activation of a Hedgehog activity. The aberrant activities can result in a pathological condition.

One embodiment of the invention is a kit useful for any of the methods disclosed herein, either in vitro or in vivo. Such a kit comprises a compound or a bioactive or pharmaceutical composition thereof, and can comprise one or more other oxysterols, e.g., which result in an increase in a Hh pathway-mediated activity, or other suitable therapeutic agents. Optionally, the kits comprise instructions for performing the method. Optional elements of a kit of the invention include suitable buffers, pharmaceutically acceptable carriers, or the like, containers, or packaging materials. The reagents of the kit may be in containers in which the reagents are stable, e.g., in lyophilized form or stabilized liquids. The reagents may also be in single use form, e.g., in single dosage form. A skilled worker will recognize components of kits suitable for carrying out any of the methods of the invention.

A variety of conditions can be treated with a compound, used alone or in combination with other therapeutic agents.

A compound can result in an increase in Hedgehog pathway activity.

One effect of a compound can be to target pluripotent cells to induce their lineage specific differentiation into various cell types, e.g., osteoblasts. For example, mesenchymal stem cells treated with a compound can show induced expression of markers of osteoblast differentiation. Without wishing to be bound by any particular mechanism, it is suggested that this lineage specific differentiation is due to the induction of Hedgehog signaling in these cells. However, methods of treatment discussed herein are included in the present invention, regardless of the mechanism by which the compound functions. A compound can be useful for treating conditions which would benefit from stimulation of bone formation, osteoblastic differentiation, osteomorphogenesis and/or osteoproliferation. Among these conditions or treatments are, e.g., osteoinductive therapy for stimulation of localized bone formation in spine fusion or osteoporosis, bone fracture repair or healing, dental procedures for which increased bone formation in the jaw is of clinical benefit, repair of craniofacial bone defects induced by trauma or congenital defects such as cleft palate/lip, and a number of other musculoskeletal disorders in which native bone growth is inadequate, which will be evident to skilled workers. Treatment can be administered to treat open fractures and fractures at high risk of non-union, and in subjects with spinal disorders, including subjects in need of spine fusion (e.g., anterior lumbar interbody fusion, posterior lumbar spinal fusion, and cervical spine fusion) or subjects having degenerative disc disease or arthritis affecting the lumbar and cervical spine. Furthermore, a compound can be used to treat osteoporosis, particularly in the aging and post-menopausal population, resulting from increased bone resorption by osteoclasts in parallel with decreased bone formation by osteoblasts.

More particularly, the following types of bone-related treatments can be carried out:

1. A compound can be used as an osteogenic agent delivered locally in the body in order to stimulate localized bone formation, using a scaffold that is composed of a compatible molecule such as but not limited to collagen I, which absorbs the compound and then is placed inside the body. For example, the scaffold containing the compound and which can be placed in between transverse processes or in the intervertebral disc where the fusion of two or more vertebrae is indicated, for example in spine fusion, pseudo-arthrosis, and non-union fusions. In other embodiments, the scaffold containing the compound is placed in a fractured bone in order to simulate bone formation and healing of the fracture; is placed in a bone defect such as calvarial or maxillofacial bone defects where bone regeneration by the compound is indicated; or is placed in the jaw bone in order to stimulate bone formation as a means of regenerating bone prior to dental procedures such as dental implants.

2. A compound can be used as an osteogenic agent in vitro. For example, it can be administered to osteoprogenitor cells, for example mesenchymal stem cells, in order to stimulate their osteogenic differentiation prior to the application of such cells in orthopedic and other procedures as indicated in 1) above in order to stimulate localized bone formation.

3. A compound can be used in vitro in order to stimulate the Hedgehog signaling pathway in osteoprogenitor cells, thereby leading to the osteogenic differentiation of the cells in vitro or in vivo.

In the foregoing and in the following examples, all temperatures are set forth in uncorrected degrees Celsius; and, unless otherwise indicated, all parts and percentages are by weight.

The osteogenic oxysterols described above are useful for direct, localized administration to target cells, tissues, or organs of interest.

EXAMPLES

Oxy149 (3a), Oxy153 (4a), Oxy154 (3b), and Oxy155 (4b) are BTA-conjugated analogs of compound Oxy133, which induce osteogenic differentiation of osteoprogenitor bone marrow stromal cells, M2-10B4. Osteogenic differentiation was assessed by the induction of alkaline phosphatase (ALP) enzymatic activity, as well as induced expression of osteogenic differentiation marker genes ALP, bone sialoprotein (BSP), and osterix (OSX).

Figure 4:
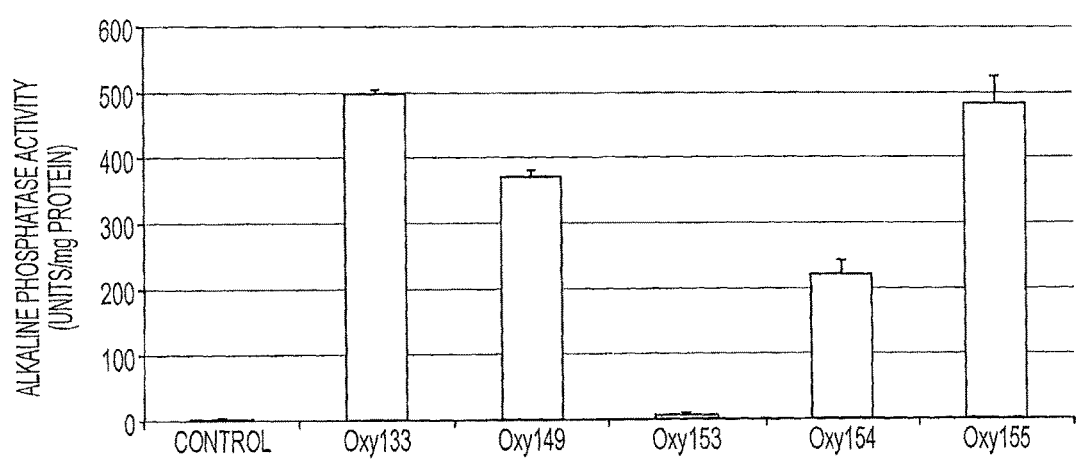
FIG. 4 shows the alkaline phosphatase (ALP) enzymatic activity of in vitro bone marrow stromal cells, M2-10B4, in contact with oxysterols.
Figure 5:
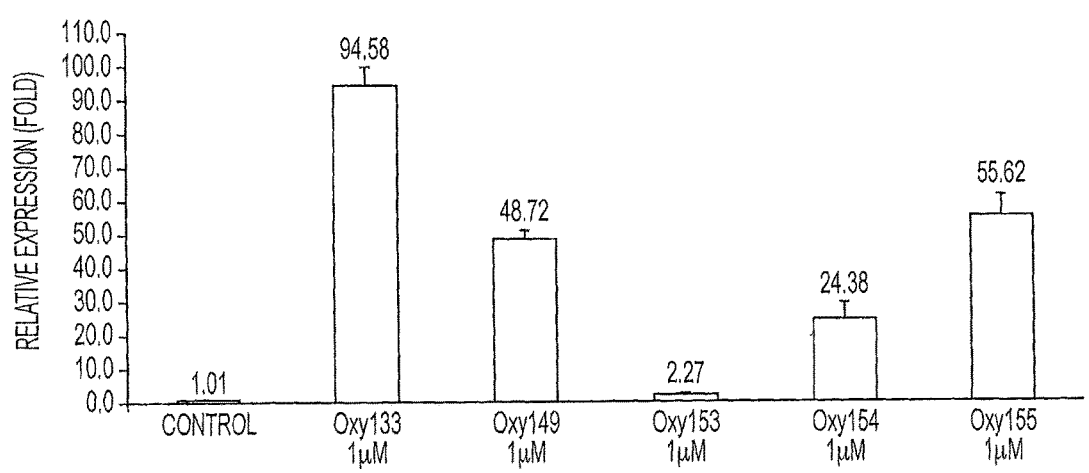
FIG. 5 shows the expression of ALP gene by M2-10B4 cells in vitro 4 days after initial contact with oxysterols.

The ALP activity of the bone marrow stromal cells, M2-10B4, in contact with each of these oxysterols at a concentration of 1 µM in vitro is shown in FIG. 4. The gene expression of ALP in M2-10B4 cells in vitro 4 days after initial contact with each oxysterol at a concentration of 1 µM in comparison with a control in which no oxysterol was contacted with the cells (control had a relative expression of 1.01) is shown in FIG. 5.

A summary of the EC50 of these oxysterols based on activation of ALP in M2-10B4 cells is presented in Table 1.

TABLE 1

| Oxysterol | EC50 |
|---|---|
| Oxy149 | 0.40 µM |
| Oxy153 | 1.40 µM |
| Oxy 154 | 0.63 µM |
| Oxy155 | 0.33 µM |

Figure 7:
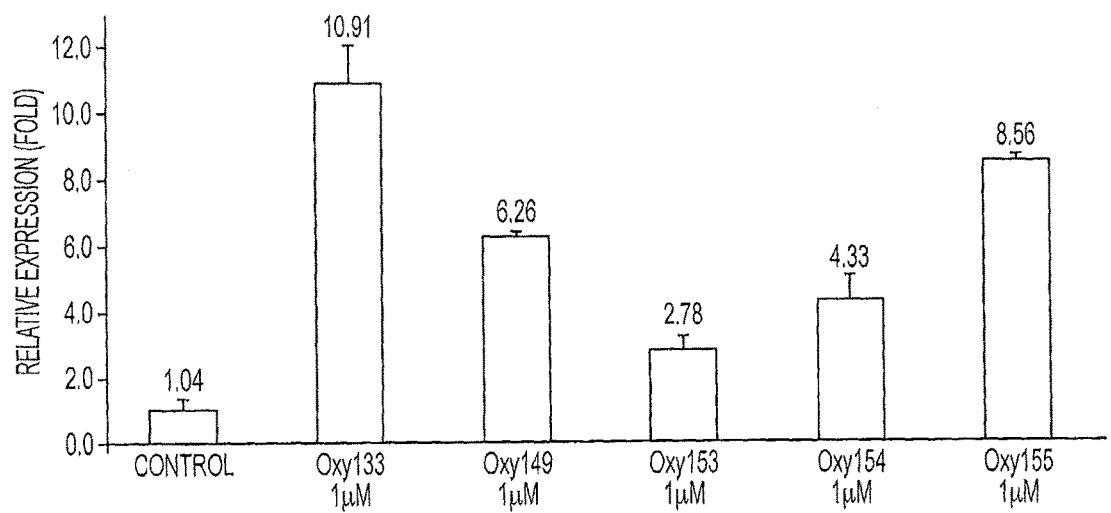
FIG. 7 shows the expression of osterix (OSX) gene of M2-10B4 cells in vitro 4 days after initial contact with oxysterols.

The gene expression of BSP in M2-10B4 cells in vitro 4 days after initial contact with each oxysterol at a concentration of 1 µM is shown in FIG. 6. The gene expression of OSX in M2-10B4 cells in vitro 4 days after initial contact with each oxysterol at a concentration of 1 µM is shown in FIG. 7.

Figure 8:
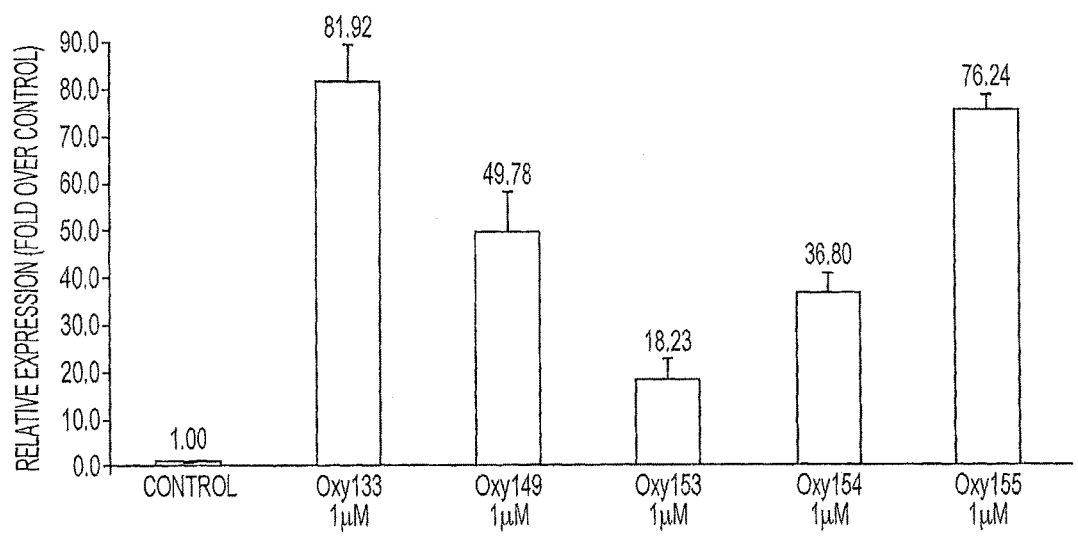
FIG. 8 shows the expression of Patched1 (Ptch) gene of M2-10B4 cells in vitro 4 days after initial contact with oxysterols.
Figure 9:
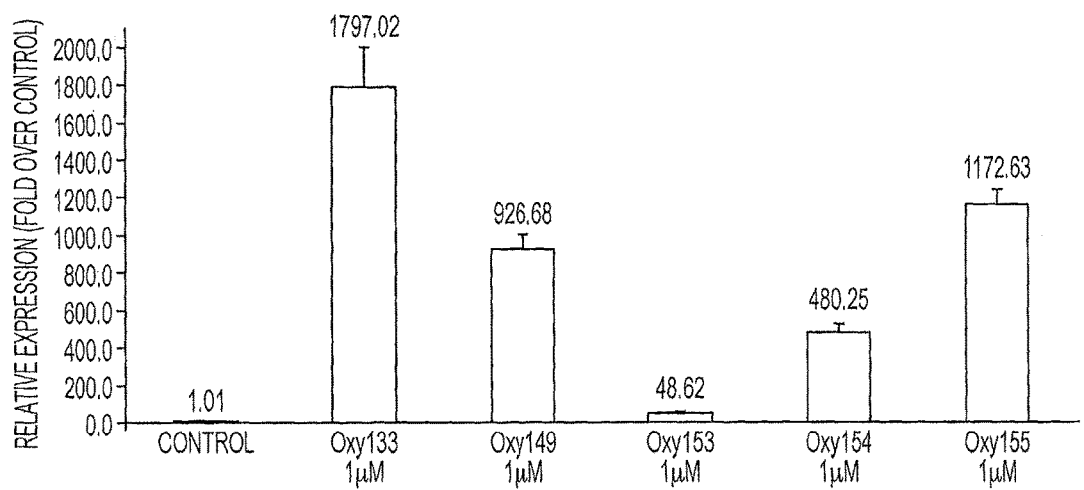
FIG. 9 shows the expression of Hedgehog (Hh) interacting protein (HIP) gene of M2-10B4 cells in vitro 4 days after initial contact with oxysterols.

Oxy149, Oxy153, Oxy154, and Oxy155 activate Hedgehog (Hh) signaling in M2-10B4 cells as determined by the induced expression of Hh target genes Patched1 (Ptch) and Hh interacting protein (HIP). In addition, these oxysterols induce osteogenic differentiation by activating Hh signaling as assessed by the inhibitory effect of Hh pathway inhibitor cyclopamine (Cyp) on oxysterol-induced osteogenic differentiation. The expression of Ptch gene in M2-10B4 cells in vitro 4 days after initial contact with each oxysterol at a concentration of 1 µM is shown in FIG. 8. The expression of HIP gene in M2-10B4 cells in vitro 4 days after initial contact with each oxysterol at a concentration of 1 µM is shown in FIG. 9.

The Hh pathway inhibitor cyclopamine can inhibit oxysterol-induced alkaline phosphatase activity. The effect of contacting cyclopamine (Cyc; 5 µM) with M2-10B4 bone marrow stromal cells in vitro, with and without contact with each oxysterol is shown in Table 2.

TABLE 2

| Treatment | ALP Activity (units/mg protein ± SD) |
|---|---|
| Control | 1 ± 1 |
| Oxy133 (1 µM) | 714 ± 5 |
| Oxy133 + Cyc | 31 ± 7 |
| Oxy149 (1 µM) | 358 ± 51 |
| Oxy149 + Cyc | 26 ± 3 |
| Oxy153 (5 µM) | 154 ± 36 |
| Oxy153 + Cyc | 19 ± 7 |
| Oxy154 (1 µM) | 390 ± 68 |
| Oxy154 + Cyc | 18 ± 2 |
| Oxy155 (1 µM) | 582 ± 8 |
| Oxy155 + Cyc | 39 ± 2 |
| Cyc | 1 ± 1 |

The BTA-conjugated analogues of Oxy133, that is, Oxy149, Oxy153, Oxy154, and Oxy155, can bind hydroxyapatite (HAP) bone mineral in vitro. An in vitro HAP binding assay was conducted as follows. A 1 mM solution of each analyte was made in 100% dimethylsulfoxide (DMSO). A further dilution was then made to form a 20 μM solution of each analyte in 50 mM Tris-HCl Buffer at pH 7.5 with 20% DMSO. Estradiol was used as a negative control and showed no binding to HAP at the concentration of 20 μM. The HAP concentration used was 50 mg/mL.

For each analyte, samples were prepared in triplicate. The control samples (1 mL of 20 μM analyte) were transferred into a microcentrifuge tube. To a second set of samples (1 mL of 20 μM analyte) in a microcentrifuge tube was added 50 mg of HAP. The samples were vortexed, gently mixed with inversion for 10 minutes at room temperature, and then centrifuged at 4,400 rpm for 2 minutes to sediment the HAP contained in the samples. The supernatant was transferred to another set of microcentrifuge tubes.

An electronic spectral scan (ultraviolet-visible) from 220-520 nm was obtained for each analyte using a Bio-Rad Smart-Spec 3000. The blank was 50 mM Tris-HCl Buffer, pH 7.5, 20% DMSO. The wavelength of maximum absorbance ($\lambda_{max}$) was determined, and the extinction coefficient ($\epsilon$) was calculated using the Beer-Lambert Law.

Figure 10:
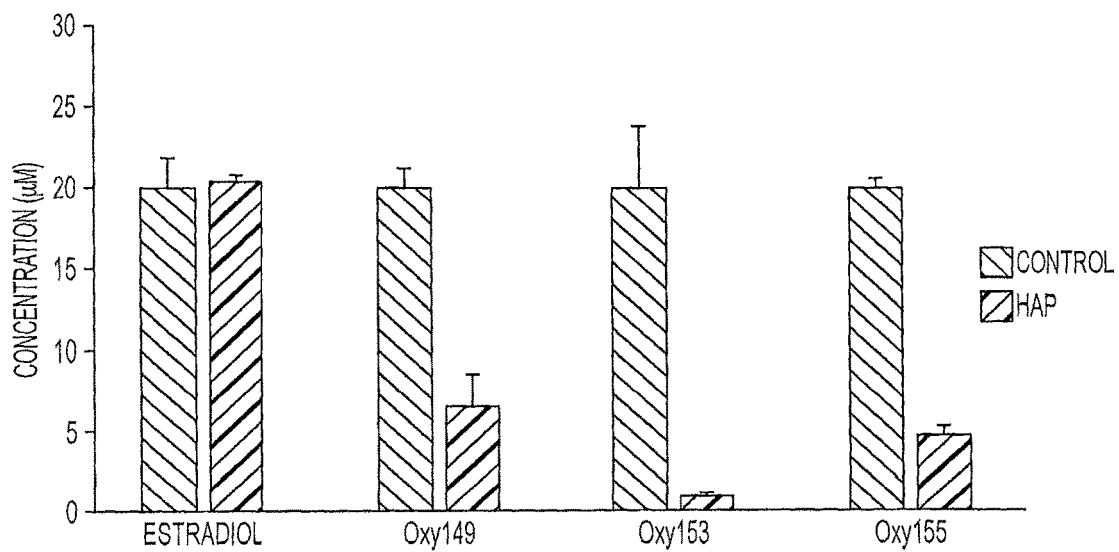
FIG. 10 shows the concentration of analytes without and with contact with hydroxyapatite (HAP).

The absorbance of the samples incubated with HAP was measured at $\lambda_{max}$ and the molar concentration of the analyte was then determined using the Beer-Lambert Law and the previously calculated $\epsilon$. The concentration of the analytes 17β-estradiol, Oxy149, Oxy153, and Oxy155 without and with contact with HAP is shown in FIG. 10.

The fraction of analyte absorbed to HAP for each sample was subsequently calculated using the following formula for % binding, $$(H_o-H)/H_o*100=\% \text{ binding}$$

with $H_o$ being the mean concentration of control samples and H being the mean calculated concentration of samples treated with HAP. The percent binding of 17β-estradiol, Oxy149, Oxy153, and Oxy155 to HAP is summarized in Table 3.

TABLE 3

| Compound | % Binding to Hydroxyapatite |
|---|---|
| 17β-estradiol | −1.95% |
| Oxy149 | 67.44% |
| Oxy153 | 95.78% |
| Oxy155 | 76.68% |

All documents, references, and information, including, but not limited to, journal articles, patent applications, and patents, that are mentioned, cited, or referred to in this application are hereby incorporated by reference in their entirety as if each had been individually incorporated. Such documents include, but are not limited to, U.S. Provisional Application for Patent bearing Ser. No. 61/643,746 (filed May 7, 2012), International Application bearing Serial number PCT/US2013/032693 (filed Mar. 15, 2013), U.S. Provisional Application for Patent bearing Ser. No. 61/643,776 (filed May 7, 2012), and International Application bearing Serial number PCT/US2013/032650 (filed Mar. 15, 2013). Such documents also include, but are not limited to, Patent Cooperation Treaty (PCT) international applications published as WO/2008/115469, WO/2008/082520, WO/2007/098281, WO/2007/028101, WO/2006/110490, WO/2005/020928, and WO/2004/019884.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

The invention claimed is:

1. A compound of the formula

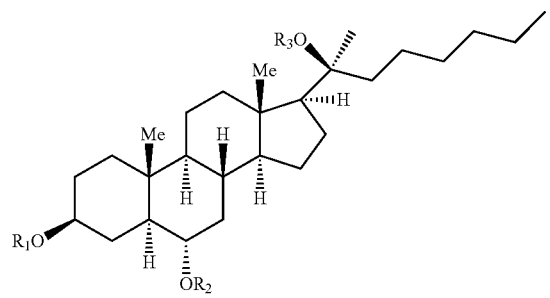

wherein $R_1$, $R_2$, and $R_3$ are independently selected from the group consisting of hydrogen,

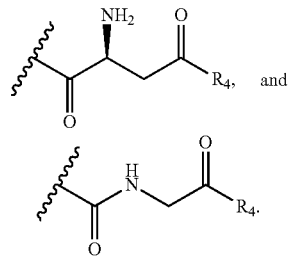

$R_4$ is

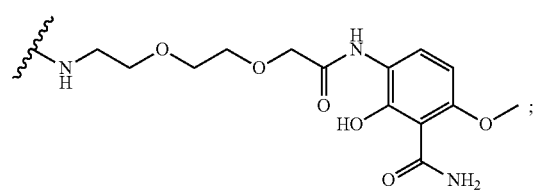 [SMILES: *NCCOCCOCC(=O)Nc1ccc(OC)c(C(N)=O)c1O]

and
wherein at least one of $R_1$, $R_2$, and $R_3$ is not hydrogen.

2. The compound of claim 1, wherein $R_3$ is hydrogen.

3. The compound of claim 1, wherein $R_2$ is hydrogen and $R_3$ is hydrogen.

4. The compound of claim 1, wherein $R_1$ is hydrogen and $R_3$ is hydrogen.

5. The compound of claim 1, wherein $R_3$ is hydrogen and $R_1$ is not hydrogen and $R_2$ is not hydrogen.

6. The compound of claim 1, wherein $R_3$ is hydrogen and $R_1$ and $R_2$ are each

| 49 | 50 |
|---|---|
| 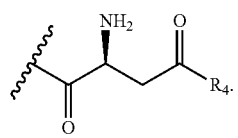 | 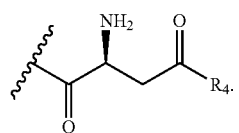 |
| 7. The compound of claim 1, wherein $R_3$ is hydrogen and $R_1$ and $R_2$ are each | 9. The compound of claim 1, wherein $R_1$, $R_2$, and $R_3$ are each |
| 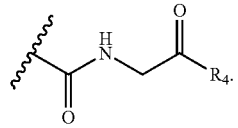 | 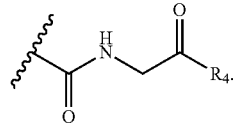 |
| 8. The compound of claim 1, wherein $R_1$, $R_2$, and $R_3$ are each | 10. The compound of claim 1, selected from the group consisting of |
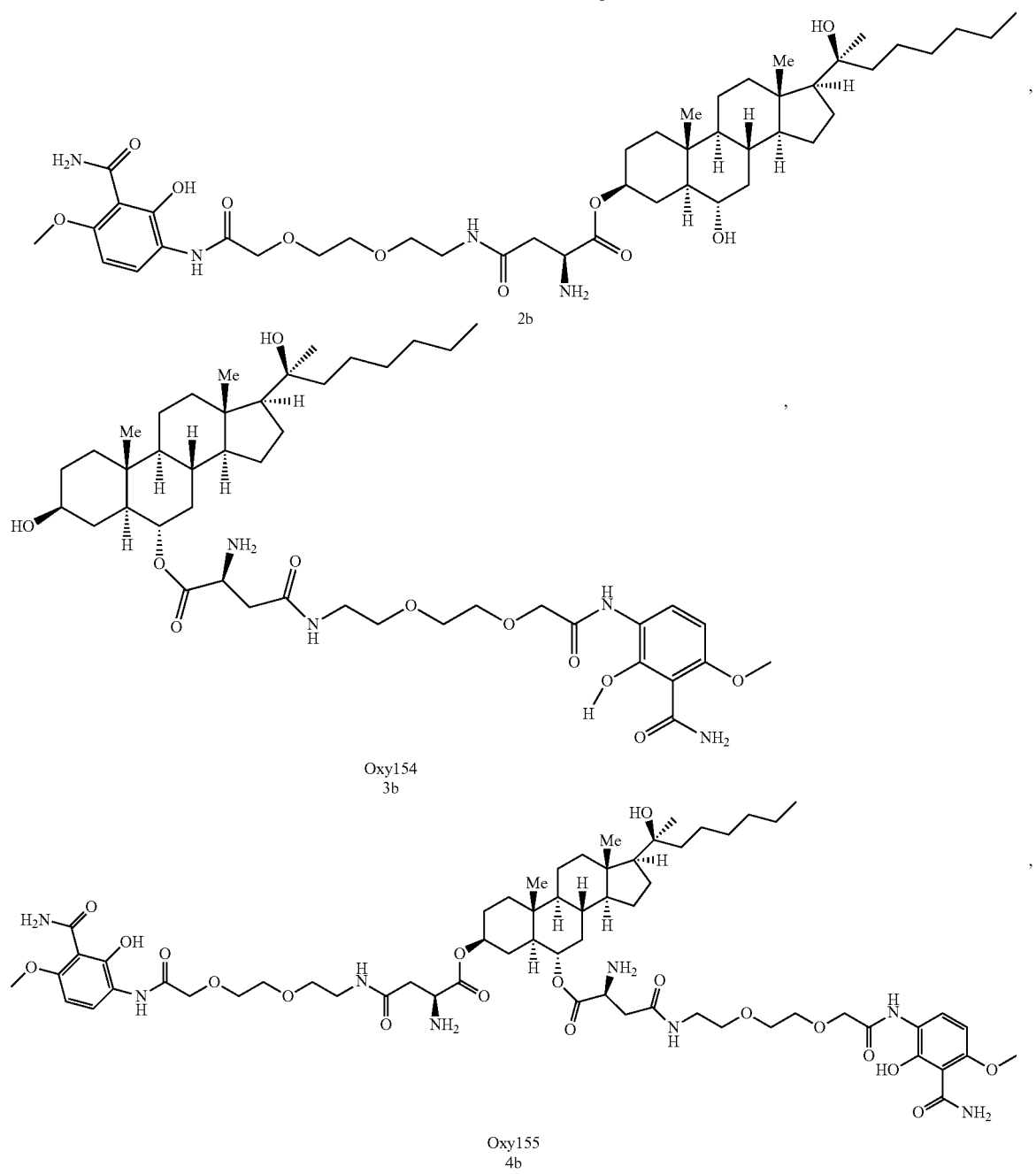

-continued
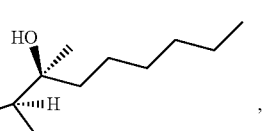
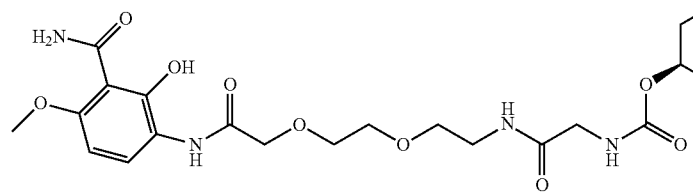
2c
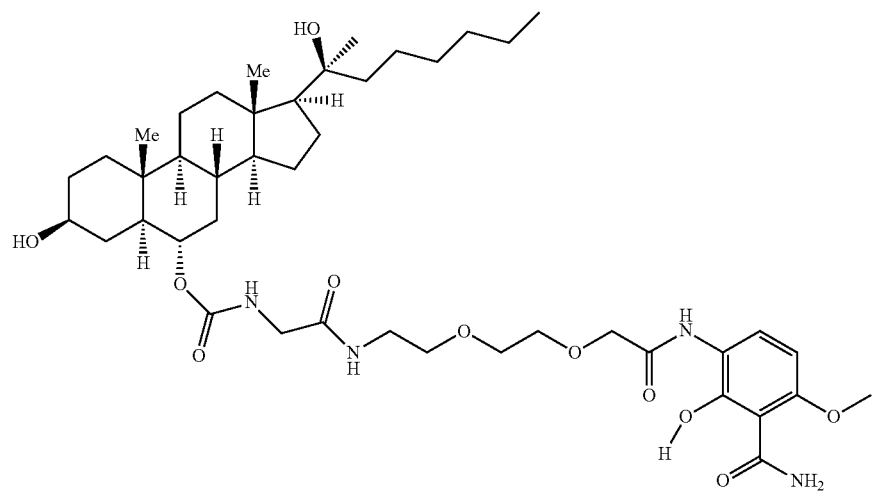
3c
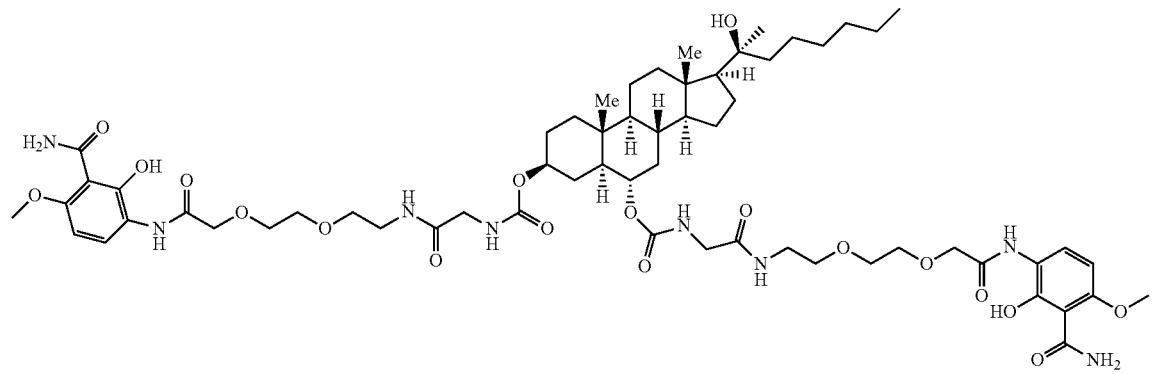
4c

-continued
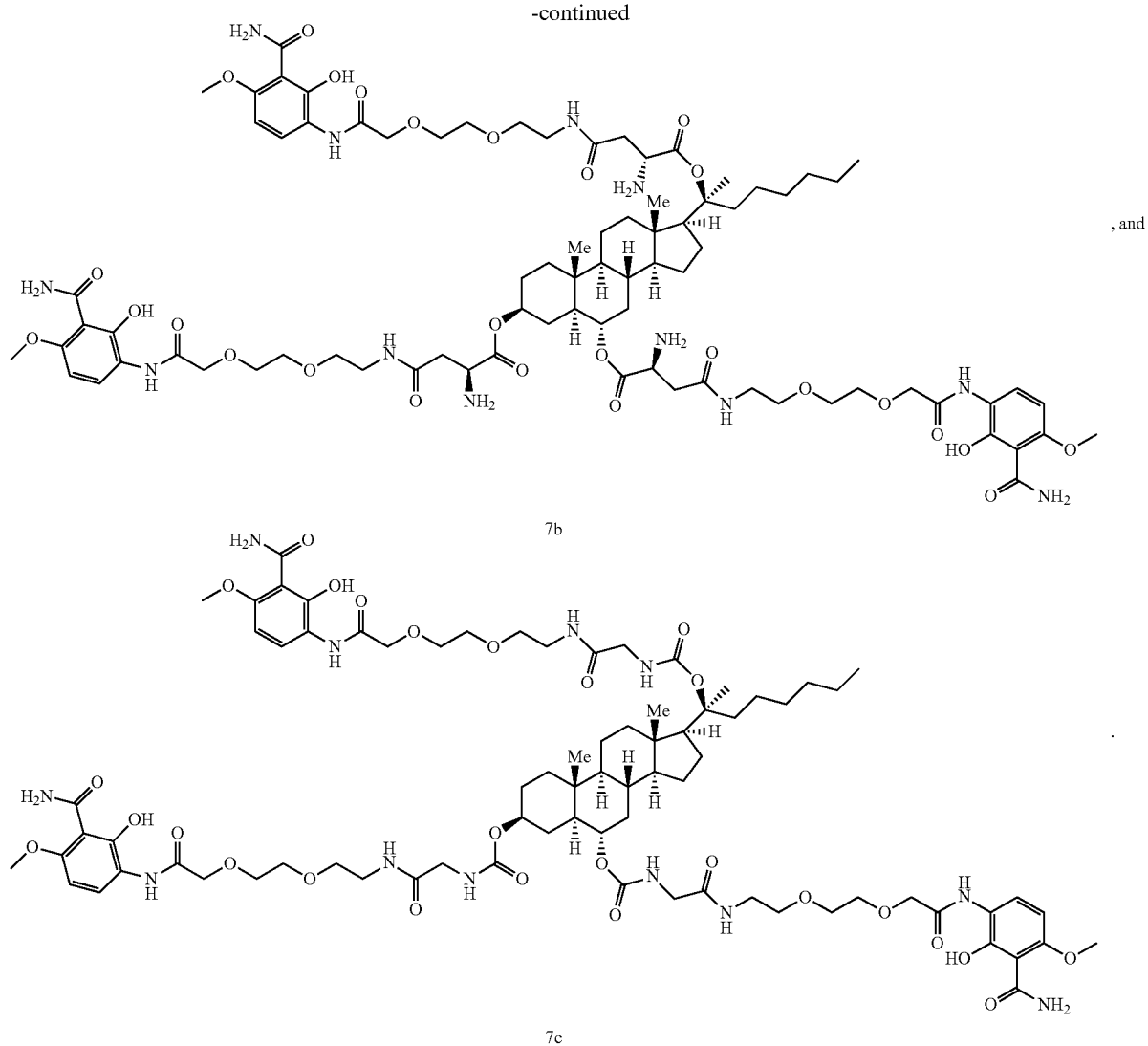
7b
7c
11. A pharmaceutical composition comprising a compound of claim 1 and a pharmaceutically acceptable carrier or diluent.
12. A compound having the structure
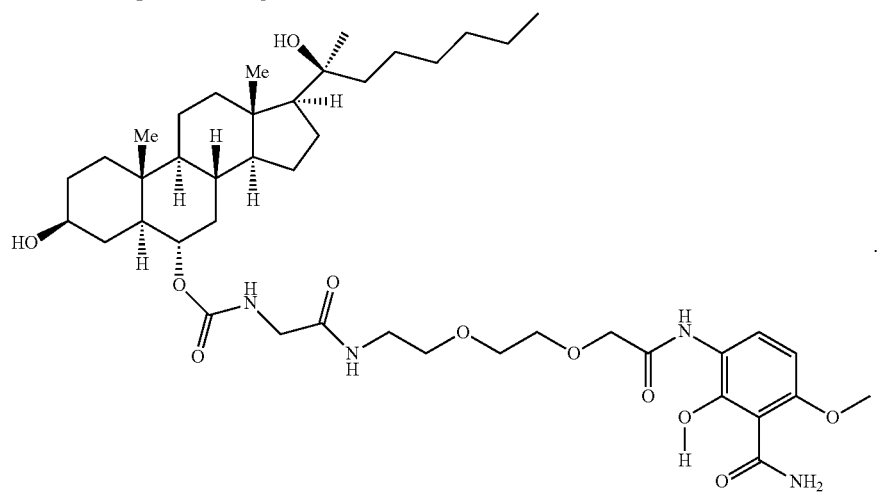
* * * * *